(12) United States Patent
Hochheimer et al.

(10) Patent No.: US 9,404,080 B2
(45) Date of Patent: Aug. 2, 2016

(54) HUMAN TASTE CELLS CAPABLE OF CONTINUOUS PROLIFERATION

(71) Applicant: B.R.A.I.N. BIOTECHNOLOGY RESEARCH AND INFORMATION NETWORK AG, Zwingenberg (DE)

(72) Inventors: Andreas Hochheimer, Darmstadt (DE); Michael Krohn, Lorsch (DE)

(73) Assignee: B.R.A.I.N. BIOTECHNOLOGY RESEARCH AND INFORMATION NETWORK AG, Zwingenberg (DE)

( * ) Notice: Subject to any disclaimer, the term of this patent is extended or adjusted under 35 U.S.C. 154(b) by 51 days.

(21) Appl. No.: 14/396,858

(22) PCT Filed: Apr. 25, 2013

(86) PCT No.: PCT/EP2013/058662
§ 371 (c)(1),
(2) Date: Oct. 24, 2014

(87) PCT Pub. No.: WO2013/160415
PCT Pub. Date: Oct. 31, 2013

(65) Prior Publication Data
US 2015/0140594 A1    May 21, 2015

(30) Foreign Application Priority Data
Apr. 25, 2012   (EP) .................... 12165564

(51) Int. Cl.
*C12N 5/071* (2010.01)
*C12N 5/00* (2006.01)
*G01N 33/50* (2006.01)
*C12N 5/0793* (2010.01)

(52) U.S. Cl.
CPC .............. *C12N 5/0632* (2013.01); *C12N 5/062* (2013.01); *G01N 33/5041* (2013.01); *C12N 2503/02* (2013.01); *G01N 2500/10* (2013.01)

(58) Field of Classification Search
None
See application file for complete search history.

(56) References Cited

FOREIGN PATENT DOCUMENTS

| EP | 1621611 A1 | 2/2006 |
|---|---|---|
| WO | 2006044594 A2 | 4/2006 |

OTHER PUBLICATIONS

Hochheimer et al., Endogenous gustatotry responses and gene expression profile of stably proliferating human taste cells isolated from fungiform papillae; Senses, vol. 39, pp. 359-377, 2014.*
Mistretta C et al: "Development of fungiform papillae: Patterned lingual gustatory organs" Archives of Histology and Cytology, Dec. 2006, vol. 69, No. 4, pp. 199-208, XP009162896.
Ozdener H et al: "Characterization and long-term maintenance of rat taste cells in culture", Chemical Senses, IRL Press, Oxford, GB, Mar. 1, 2006, vol. 31, No. 3, pp. 279-290, XP002481585.
Ozdener Mehmet Hakan et al.,"Characterization of human fungiform papillae cells in culture," Chemical Senses, Oxford University Press, Sep. 1, 2011, vol. 36, No. 7, pp. 601-612, XP009162861.

* cited by examiner

*Primary Examiner* — Addison D Ault
(74) *Attorney, Agent, or Firm* — Gorman IP Law, APC

(57) ABSTRACT

The present invention relates to proliferating human taste cells, wherein the cells are the cells deposited under the DSMZ deposit accession number DSM ACC3169 or taste cells derived thereof. The present invention further relates to the proliferating human taste cells of the invention for use in research. Further, the present invention relates to in vitro methods for analyzing the signalling response of taste cells to a molecule involved in taste signalling, in vitro methods of identifying agents capable of eliciting a taste response in taste cells as well as in vitro methods of identifying modulators of taste signalling.

15 Claims, 13 Drawing Sheets

| Cell line | Cp *large hTERT* | Cp *large T* | Cp *PPIA* |
|---|---|---|---|
| BR-HTC18 | 22.70 | no product | 24.03 |
| BR-HTC28 | 24.90 | 25.40 | 24.70 |

| Cell line | Cp hTASR38 | Cp TOP1 |
|---|---|---|
| BR-HTC8 | no product | 24,56 |
| BR-HTC38 | 19,92 | 23,77 |

Figure 3:
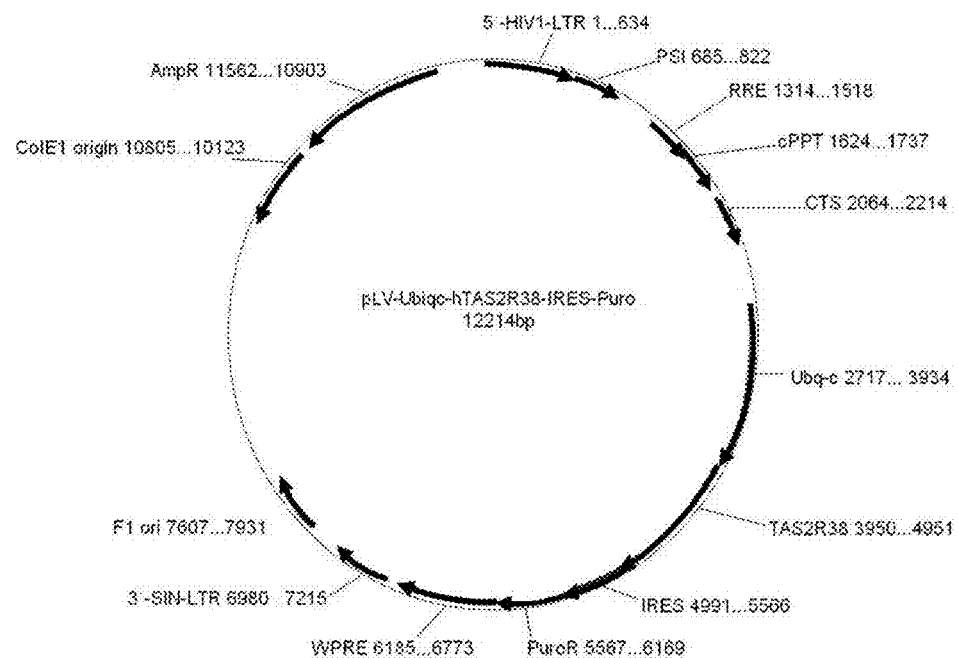

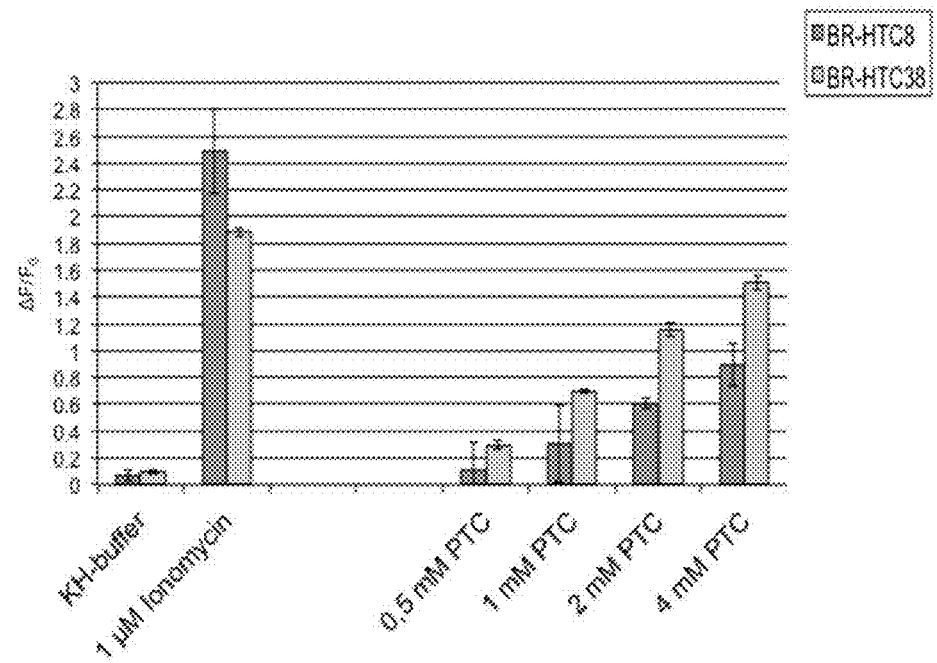
Figure 3 C
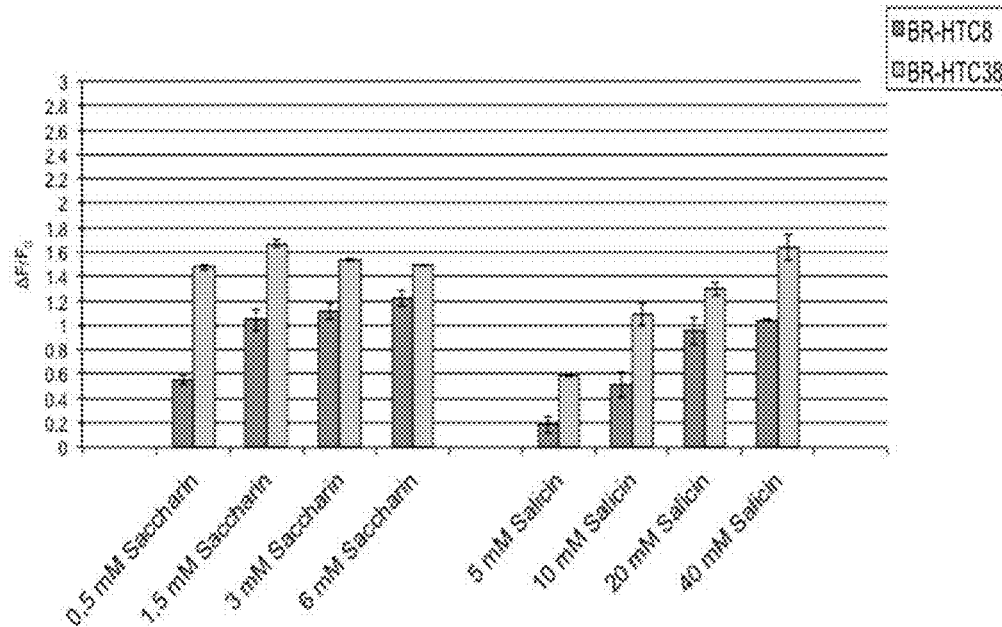

BR-HTC8
Combinatorial addition of salicin alone (black squares) and salicin plus four different concentrations of saccharin (white symbols).

SEQUENCE LISTING

<160> NUMBER OF SEQ ID NOS: 286

<210> SEQ ID NO 1
<211> LENGTH: 21
<212> TYPE: DNA
<213> ORGANISM: Artificial sequence
<220> FEATURE:
<223> OTHER INFORMATION: shRNA against the taste receptor TAS2R16

<400> SEQUENCE: 1
gcttgagtcc ttgacaatta t                                          21

<210> SEQ ID NO 2
<211> LENGTH: 21
<212> TYPE: DNA
<213> ORGANISM: Artificial sequence
<220> FEATURE:
<223> OTHER INFORMATION: shRNA against the taste receptor TAS2R16

<400> SEQUENCE: 2
gctttcatct taatgcattc c                                          21

<210> SEQ ID NO 3
<211> LENGTH: 21
<212> TYPE: DNA
<213> ORGANISM: Artificial sequence

```
<220> FEATURE:
<223> OTHER INFORMATION: shRNA against the taste receptor TAS2R44

<400> SEQUENCE: 3
gtggtagtgg ttctatttgt t                                           21

<210> SEQ ID NO 4
<211> LENGTH: 21
<212> TYPE: DNA
<213> ORGANISM: Artificial sequence
<220> FEATURE:
<223> OTHER INFORMATION: shRNA against the taste receptor TAS2R44

<400> SEQUENCE: 4
ggtttgctct gggtattatt a                                           21

<210> SEQ ID NO 5
<211> LENGTH: 21
<212> TYPE: DNA
<213> ORGANISM: Artificial sequence
<220> FEATURE:
<223> OTHER INFORMATION: TRPV1, forward Primer

<400> SEQUENCE: 5
tccagcagat gggcatctat g                                           21

<210> SEQ ID NO 6
<211> LENGTH: 21
<212> TYPE: DNA
<213> ORGANISM: Artificial sequence
<220> FEATURE:
<223> OTHER INFORMATION: TRPV1, reverse primer

<400> SEQUENCE: 6
aggacaagtg ggacagattc g                                           21

<210> SEQ ID NO 7
<211> LENGTH: 20
<212> TYPE: DNA
<213> ORGANISM: Artificial sequence
<220> FEATURE:
<223> OTHER INFORMATION: TRPML3, forward primer

<400> SEQUENCE: 7
gcagacagtt cgtcatcaag                                             20

<210> SEQ ID NO 8
<211> LENGTH: 20
<212> TYPE: DNA
<213> ORGANISM: Artificial sequence
<220> FEATURE:
<223> OTHER INFORMATION: TRPML3, reverse primer

<400> SEQUENCE: 8
ctcctgctga agctgaagtc                                             20

<210> SEQ ID NO 9
<211> LENGTH: 21
<212> TYPE: DNA
<213> ORGANISM: Artificial sequence
<220> FEATURE:
<223> OTHER INFORMATION: Gustducin, forward primer

<400> SEQUENCE: 9
gctgcactta gtgcctatga c                                           21
```

```
<210> SEQ ID NO 10
<211> LENGTH: 21
<212> TYPE: DNA
<213> ORGANISM: Artificial sequence
<220> FEATURE:
<223> OTHER INFORMATION: Gustducin, reverse primer

<400> SEQUENCE: 10
gcccagtgta ttctggaaag c                                              21

<210> SEQ ID NO 11
<211> LENGTH: 21
<212> TYPE: DNA
<213> ORGANISM: Artificial sequence
<220> FEATURE:
<223> OTHER INFORMATION: TRPM5, forward primer

<400> SEQUENCE: 11
acgagattga tgaagcccgt g                                              21

<210> SEQ ID NO 12
<211> LENGTH: 21
<212> TYPE: DNA
<213> ORGANISM: Artificial sequence
<220> FEATURE:
<223> OTHER INFORMATION: TRPM5, reverse primer

<400> SEQUENCE: 12
catgagcagc acattggtga c                                              21

<210> SEQ ID NO 13
<211> LENGTH: 20
<212> TYPE: DNA
<213> ORGANISM: Artificial sequence
<220> FEATURE:
<223> OTHER INFORMATION: Oct-4, forward primer

<400> SEQUENCE: 13
ctgggttgat cctcggacct                                                20

<210> SEQ ID NO 14
<211> LENGTH: 19
<212> TYPE: DNA
<213> ORGANISM: Artificial sequence
<220> FEATURE:
<223> OTHER INFORMATION: Oct-4, reverse primer

<400> SEQUENCE: 14
ccatcggagt tgctctcca                                                 19

<210> SEQ ID NO 15
<211> LENGTH: 21
<212> TYPE: DNA
<213> ORGANISM: Artificial sequence
<220> FEATURE:
<223> OTHER INFORMATION: T1R1, forward primer

<400> SEQUENCE: 15
cggagtcttc tcctgacttc a                                              21

<210> SEQ ID NO 16
<211> LENGTH: 22
<212> TYPE: DNA
<213> ORGANISM: Artificial sequence
<220> FEATURE:
<223> OTHER INFORMATION: T1R1, reverse primer
```

```
<400> SEQUENCE: 16
ccgtggagtt gtttatctcc tc                                             22

<210> SEQ ID NO 17
<211> LENGTH: 19
<212> TYPE: DNA
<213> ORGANISM: Artificial sequence
<220> FEATURE:
<223> OTHER INFORMATION: T1R2, forward primer

<400> SEQUENCE: 17
cgtcgtggtc gtgttctcg                                                 19

<210> SEQ ID NO 18
<211> LENGTH: 21
<212> TYPE: DNA
<213> ORGANISM: Artificial sequence
<220> FEATURE:
<223> OTHER INFORMATION: T1R2, reverse primer

<400> SEQUENCE: 18
cactcgcgga actcactgaa g                                              21

<210> SEQ ID NO 19
<211> LENGTH: 20
<212> TYPE: DNA
<213> ORGANISM: Artificial sequence
<220> FEATURE:
<223> OTHER INFORMATION: T1R3, forward primer

<400> SEQUENCE: 19
ccgcctactg caactacacg                                                20

<210> SEQ ID NO 20
<211> LENGTH: 20
<212> TYPE: DNA
<213> ORGANISM: Artificial sequence
<220> FEATURE:
<223> OTHER INFORMATION: T1R3, reverse primer

<400> SEQUENCE: 20
ctagcaccgt agctgacctg                                                20

<210> SEQ ID NO 21
<211> LENGTH: 20
<212> TYPE: DNA
<213> ORGANISM: Artificial sequence
<220> FEATURE:
<223> OTHER INFORMATION: PLCb2, forward primer

<400> SEQUENCE: 21
gactcccggc ttaactccct                                                20

<210> SEQ ID NO 22
<211> LENGTH: 19
<212> TYPE: DNA
<213> ORGANISM: Artificial sequence
<220> FEATURE:
<223> OTHER INFORMATION: PLCb2, reverse primer

<400> SEQUENCE: 22
cggctgtcag gtaggtgtt                                                 19

<210> SEQ ID NO 23
```

```
<211> LENGTH: 21
<212> TYPE: DNA
<213> ORGANISM: Artificial sequence
<220> FEATURE:
<223> OTHER INFORMATION: Keratin 5, forward primer

<400> SEQUENCE: 23
atgtctcgcc agtcaagtgt g                                          21

<210> SEQ ID NO 24
<211> LENGTH: 19
<212> TYPE: DNA
<213> ORGANISM: Artificial sequence
<220> FEATURE:
<223> OTHER INFORMATION: Keratin 5, reverse primer

<400> SEQUENCE: 24
ctgcctcctc tagtgctga                                             19

<210> SEQ ID NO 25
<211> LENGTH: 20
<212> TYPE: DNA
<213> ORGANISM: Artificial sequence
<220> FEATURE:
<223> OTHER INFORMATION: Keratin 8, forward primer

<400> SEQUENCE: 25
ggaggcatca ccgcagttac                                            20

<210> SEQ ID NO 26
<211> LENGTH: 23
<212> TYPE: DNA
<213> ORGANISM: Artificial sequence
<220> FEATURE:
<223> OTHER INFORMATION: Keratin 8, reverse primer

<400> SEQUENCE: 26
ggttggcaat atcctcgtac tgt                                        23

<210> SEQ ID NO 27
<211> LENGTH: 21
<212> TYPE: DNA
<213> ORGANISM: Artificial sequence
<220> FEATURE:
<223> OTHER INFORMATION: NCAM, forward primer

<400> SEQUENCE: 27
acatcacctg ctacttcctg a                                          21

<210> SEQ ID NO 28
<211> LENGTH: 23
<212> TYPE: DNA
<213> ORGANISM: Artificial sequence
<220> FEATURE:
<223> OTHER INFORMATION: NCAM, reverse primer

<400> SEQUENCE: 28
cttggactca tctttcgaga agg                                        23

<210> SEQ ID NO 29
<211> LENGTH: 20
<212> TYPE: DNA
<213> ORGANISM: Artificial sequence
<220> FEATURE:
<223> OTHER INFORMATION: IP3R3, forward primer

<400> SEQUENCE: 29
```

```
gactgcctct tcaaggtgtg                                              20

<210> SEQ ID NO 30
<211> LENGTH: 21
<212> TYPE: DNA
<213> ORGANISM: Artificial sequence
<220> FEATURE:
<223> OTHER INFORMATION: IP3R3, reverse primer

<400> SEQUENCE: 30
acactgccat acttcacgac a                                            21

<210> SEQ ID NO 31
<211> LENGTH: 19
<212> TYPE: DNA
<213> ORGANISM: Artificial sequence
<220> FEATURE:
<223> OTHER INFORMATION: Keratin 19, forward primer

<400> SEQUENCE: 31
aacggcgagc tagaggtga                                               19

<210> SEQ ID NO 32
<211> LENGTH: 21
<212> TYPE: DNA
<213> ORGANISM: Artificial sequence
<220> FEATURE:
<223> OTHER INFORMATION: Keratin 19, reverse primer

<400> SEQUENCE: 32
ttccgtctca aacttggttc g                                            21

<210> SEQ ID NO 33
<211> LENGTH: 19
<212> TYPE: DNA
<213> ORGANISM: Artificial sequence
<220> FEATURE:
<223> OTHER INFORMATION: Sox 2, forward primer

<400> SEQUENCE: 33
tggacagtta cgcgcacat                                               19

<210> SEQ ID NO 34
<211> LENGTH: 21
<212> TYPE: DNA
<213> ORGANISM: Artificial sequence
<220> FEATURE:
<223> OTHER INFORMATION: Sox 2, reverse primer

<400> SEQUENCE: 34
cgagtaggac atgctgtagg t                                            21

<210> SEQ ID NO 35
<211> LENGTH: 20
<212> TYPE: DNA
<213> ORGANISM: Artificial sequence
<220> FEATURE:
<223> OTHER INFORMATION: TP63, forward primer

<400> SEQUENCE: 35
gagccgtgag ttcaacgagg                                              20

<210> SEQ ID NO 36
<211> LENGTH: 21
<212> TYPE: DNA
```

```
<213> ORGANISM: Artificial sequence
<220> FEATURE:
<223> OTHER INFORMATION: TP63, reverse primer

<400> SEQUENCE: 36
cttgcccatc tctggtttcc a                                              21

<210> SEQ ID NO 37
<211> LENGTH: 22
<212> TYPE: DNA
<213> ORGANISM: Artificial sequence
<220> FEATURE:
<223> OTHER INFORMATION: SHH, forward primer

<400> SEQUENCE: 37
actccgagcg atttaaggaa ct                                             22

<210> SEQ ID NO 38
<211> LENGTH: 21
<212> TYPE: DNA
<213> ORGANISM: Artificial sequence
<220> FEATURE:
<223> OTHER INFORMATION: SHH, reverse primer

<400> SEQUENCE: 38
cagacgtggt gatgtccact g                                              21

<210> SEQ ID NO 39
<211> LENGTH: 19
<212> TYPE: DNA
<213> ORGANISM: Artificial sequence
<220> FEATURE:
<223> OTHER INFORMATION: Ptc 1, forward primer

<400> SEQUENCE: 39
gaccgggact atctgcacc                                                 19

<210> SEQ ID NO 40
<211> LENGTH: 21
<212> TYPE: DNA
<213> ORGANISM: Artificial sequence
<220> FEATURE:
<223> OTHER INFORMATION: Ptc 1, reverse primer

<400> SEQUENCE: 40
gaggcccaca accaagaact t                                              21

<210> SEQ ID NO 41
<211> LENGTH: 21
<212> TYPE: DNA
<213> ORGANISM: Artificial sequence
<220> FEATURE:
<223> OTHER INFORMATION: Glast, forward primer

<400> SEQUENCE: 41
atccttggat ttaccctccg a                                              21

<210> SEQ ID NO 42
<211> LENGTH: 20
<212> TYPE: DNA
<213> ORGANISM: Artificial sequence
<220> FEATURE:
<223> OTHER INFORMATION: Glast, reverse primer

<400> SEQUENCE: 42
cgccattcct gtgacaagac                                                20
```

```
<210> SEQ ID NO 43
<211> LENGTH: 46
<212> TYPE: DNA
<213> ORGANISM: Artificial sequence
<220> FEATURE:
<223> OTHER INFORMATION: NTPD, forward primer

<400> SEQUENCE: 43
caactatctg ctgggcaaat tcaggcaggt ctggattgag ttatac          46

<210> SEQ ID NO 44
<211> LENGTH: 23
<212> TYPE: DNA
<213> ORGANISM: Artificial sequence
<220> FEATURE:
<223> OTHER INFORMATION: NTPD, reverse primer

<400> SEQUENCE: 44
caactatctg ctgggcaaat tca                                    23

<210> SEQ ID NO 45
<211> LENGTH: 23
<212> TYPE: DNA
<213> ORGANISM: Artificial sequence
<220> FEATURE:
<223> OTHER INFORMATION: Trf2, forward primer

<400> SEQUENCE: 45
aaggaagatt gctttggaag gag                                    23

<210> SEQ ID NO 46
<211> LENGTH: 19
<212> TYPE: DNA
<213> ORGANISM: Artificial sequence
<220> FEATURE:
<223> OTHER INFORMATION: Trf2, reverse primer

<400> SEQUENCE: 46
gcagactacg ggctaagcg                                         19

<210> SEQ ID NO 47
<211> LENGTH: 20
<212> TYPE: DNA
<213> ORGANISM: Artificial sequence
<220> FEATURE:
<223> OTHER INFORMATION: Trf3, forward primer

<400> SEQUENCE: 47
caccctggtg atactgactc                                        20

<210> SEQ ID NO 48
<211> LENGTH: 20
<212> TYPE: DNA
<213> ORGANISM: Artificial sequence
<220> FEATURE:
<223> OTHER INFORMATION: Trf3, reverse primer

<400> SEQUENCE: 48
tacaggccag gtttacagtg                                        20

<210> SEQ ID NO 49
<211> LENGTH: 21
<212> TYPE: DNA
<213> ORGANISM: Artificial sequence
<220> FEATURE:
```

<223> OTHER INFORMATION: Tbp, forward primer

<400> SEQUENCE: 49
ccactcacag actctcacaa c                                              21

<210> SEQ ID NO 50
<211> LENGTH: 21
<212> TYPE: DNA
<213> ORGANISM: Artificial sequence
<220> FEATURE:
<223> OTHER INFORMATION: Tbp, reverse primer

<400> SEQUENCE: 50
ctgcggtaca atcccagaac t                                              21

<210> SEQ ID NO 51
<211> LENGTH: 21
<212> TYPE: DNA
<213> ORGANISM: Artificial sequence
<220> FEATURE:
<223> OTHER INFORMATION: mGlu1, forward primer

<400> SEQUENCE: 51
ccagcgatct ttttggaggt g                                              21

<210> SEQ ID NO 52
<211> LENGTH: 19
<212> TYPE: DNA
<213> ORGANISM: Artificial sequence
<220> FEATURE:
<223> OTHER INFORMATION: mGlu1, reverse primer

<400> SEQUENCE: 52
cctctcgggc actttctcg                                                 19

<210> SEQ ID NO 53
<211> LENGTH: 23
<212> TYPE: DNA
<213> ORGANISM: Artificial sequence
<220> FEATURE:
<223> OTHER INFORMATION: mGlu4, forward primer

<400> SEQUENCE: 53
aaggaagatt gctttggaag gag                                            23

<210> SEQ ID NO 54
<211> LENGTH: 19
<212> TYPE: DNA
<213> ORGANISM: Artificial sequence
<220> FEATURE:
<223> OTHER INFORMATION: mGlu4, reverse primer

<400> SEQUENCE: 54
gcagactacg ggctaagcg                                                 19

<210> SEQ ID NO 55
<211> LENGTH: 20
<212> TYPE: DNA
<213> ORGANISM: Artificial sequence
<220> FEATURE:
<223> OTHER INFORMATION: beta actin, forward primer

<400> SEQUENCE: 55
gtggggcgcc ccaggcacca                                                20

<210> SEQ ID NO 56
<211> LENGTH: 20
<212> TYPE: DNA
<213> ORGANISM: Artificial sequence
<220> FEATURE:
<223> OTHER INFORMATION: beta actin, reverse primer

<400> SEQUENCE: 56
gtggggcgcc ccaggcacca                                        20

<210> SEQ ID NO 57
<211> LENGTH: 20
<212> TYPE: DNA
<213> ORGANISM: Artificial sequence
<220> FEATURE:
<223> OTHER INFORMATION: PKD2L1, forward primer

<400> SEQUENCE: 57
ccaccttcac caagtttgac                                        20

<210> SEQ ID NO 58
<211> LENGTH: 20
<212> TYPE: DNA
<213> ORGANISM: Artificial sequence
<220> FEATURE:
<223> OTHER INFORMATION: PKD2L1, reverse primer

<400> SEQUENCE: 58
gcatcaatct gggacactac                                        20

<210> SEQ ID NO 59
<211> LENGTH: 21
<212> TYPE: DNA
<213> ORGANISM: Artificial sequence
<220> FEATURE:
<223> OTHER INFORMATION: Keratin 14, forward primer

<400> SEQUENCE: 59
catgagtgtg gaagccgaca t                                      21

<210> SEQ ID NO 60
<211> LENGTH: 21
<212> TYPE: DNA
<213> ORGANISM: Artificial sequence
<220> FEATURE:
<223> OTHER INFORMATION: Keratin 14, reverse primer

<400> SEQUENCE: 60
gcctctcagg gcattcatct c                                      21

<210> SEQ ID NO 61
<211> LENGTH: 19
<212> TYPE: DNA
<213> ORGANISM: Artificial sequence
<220> FEATURE:
<223> OTHER INFORMATION: Mash1, forward primer

<400> SEQUENCE: 61
cgcggccaac aagaagatg                                         19

<210> SEQ ID NO 62
<211> LENGTH: 20
<212> TYPE: DNA
<213> ORGANISM: Artificial sequence
<220> FEATURE:
<223> OTHER INFORMATION: Mash1, reverse primer

```
<400> SEQUENCE: 62
cgacgagtag gatgagaccg                                              20

<210> SEQ ID NO 63
<211> LENGTH: 19
<212> TYPE: DNA
<213> ORGANISM: Artificial sequence
<220> FEATURE:
<223> OTHER INFORMATION: SCNN1A, forward primer

<400> SEQUENCE: 63
tcgagttcca ccgctccta                                               19

<210> SEQ ID NO 64
<211> LENGTH: 21
<212> TYPE: DNA
<213> ORGANISM: Artificial sequence
<220> FEATURE:
<223> OTHER INFORMATION: SCNN1A, reverse primer

<400> SEQUENCE: 64
gccagtacat catgccaaag g                                            21

<210> SEQ ID NO 65
<211> LENGTH: 21
<212> TYPE: DNA
<213> ORGANISM: Artificial sequence
<220> FEATURE:
<223> OTHER INFORMATION: SCNN1B, forward primer

<400> SEQUENCE: 65
caggacctac ttgagctggg a                                            21

<210> SEQ ID NO 66
<211> LENGTH: 21
<212> TYPE: DNA
<213> ORGANISM: Artificial sequence
<220> FEATURE:
<223> OTHER INFORMATION: SCNN1B, reverse primer

<400> SEQUENCE: 66
ccaggattct ctccaggaca g                                            21

<210> SEQ ID NO 67
<211> LENGTH: 22
<212> TYPE: DNA
<213> ORGANISM: Artificial sequence
<220> FEATURE:
<223> OTHER INFORMATION: SCNN1G, forward primer

<400> SEQUENCE: 67
ccgaccatta aagagctgat gc                                           22

<210> SEQ ID NO 68
<211> LENGTH: 21
<212> TYPE: DNA
<213> ORGANISM: Artificial sequence
<220> FEATURE:
<223> OTHER INFORMATION: SCNN1G, reverse primer

<400> SEQUENCE: 68
agtcagtgtg aacccgatcc a                                            21

<210> SEQ ID NO 69
<211> LENGTH: 21
```

```
<212> TYPE: DNA
<213> ORGANISM: Artificial sequence
<220> FEATURE:
<223> OTHER INFORMATION: SCNN1D, forward primer

<400> SEQUENCE: 69
ggcatcaggg tcatggttca c                                         21

<210> SEQ ID NO 70
<211> LENGTH: 20
<212> TYPE: DNA
<213> ORGANISM: Artificial sequence
<220> FEATURE:
<223> OTHER INFORMATION: SCNN1D, reverse primer

<400> SEQUENCE: 70
gtggaggtag tagccacagg                                           20

<210> SEQ ID NO 71
<211> LENGTH: 21
<212> TYPE: DNA
<213> ORGANISM: Artificial sequence
<220> FEATURE:
<223> OTHER INFORMATION: SNAP 25, forward primer

<400> SEQUENCE: 71
cttcatccgc agggtaacaa a                                         21

<210> SEQ ID NO 72
<211> LENGTH: 21
<212> TYPE: DNA
<213> ORGANISM: Artificial sequence
<220> FEATURE:
<223> OTHER INFORMATION: SNAP 25, reverse primer

<400> SEQUENCE: 72
tctcattgcc catatccagg g                                         21

<210> SEQ ID NO 73
<211> LENGTH: 23
<212> TYPE: DNA
<213> ORGANISM: Artificial sequence
<220> FEATURE:
<223> OTHER INFORMATION: PC 1/3, forward primer

<400> SEQUENCE: 73
tttgggtcag attggttcac ttg                                       23

<210> SEQ ID NO 74
<211> LENGTH: 22
<212> TYPE: DNA
<213> ORGANISM: Artificial sequence
<220> FEATURE:
<223> OTHER INFORMATION: PC 1/3, reverse primer

<400> SEQUENCE: 74
gcccatatca cacgatcatc at                                        22

<210> SEQ ID NO 75
<211> LENGTH: 21
<212> TYPE: DNA
<213> ORGANISM: Artificial sequence
<220> FEATURE:
<223> OTHER INFORMATION: ESPN, forward primer

<400> SEQUENCE: 75
```
cagagtgcag gacaaagaca a                                         21

<210> SEQ ID NO 76
<211> LENGTH: 21
<212> TYPE: DNA
<213> ORGANISM: Artificial sequence
<220> FEATURE:
<223> OTHER INFORMATION: ESPN, reverse primer

<400> SEQUENCE: 76
cagagtgcag gacaaagaca a                                         21

<210> SEQ ID NO 77
<211> LENGTH: 19
<212> TYPE: DNA
<213> ORGANISM: Artificial sequence
<220> FEATURE:
<223> OTHER INFORMATION: GOAT, forward primer

<400> SEQUENCE: 77
gctggcagac cttgtgtca                                            19

<210> SEQ ID NO 78
<211> LENGTH: 23
<212> TYPE: DNA
<213> ORGANISM: Artificial sequence
<220> FEATURE:
<223> OTHER INFORMATION: GOAT, reverse primer

<400> SEQUENCE: 78
caagtagctg aaatagggca gtg                                       23

<210> SEQ ID NO 79
<211> LENGTH: 20
<212> TYPE: DNA
<213> ORGANISM: Artificial sequence
<220> FEATURE:
<223> OTHER INFORMATION: Oct-11, forward primer

<400> SEQUENCE: 79
ttcccggcca cttacagtct                                           20

<210> SEQ ID NO 80
<211> LENGTH: 22
<212> TYPE: DNA
<213> ORGANISM: Artificial sequence
<220> FEATURE:
<223> OTHER INFORMATION: Oct-11, reverse primer

<400> SEQUENCE: 80
caggtggggt tctaaagagg at                                        22

<210> SEQ ID NO 81
<211> LENGTH: 21
<212> TYPE: DNA
<213> ORGANISM: Artificial sequence
<220> FEATURE:
<223> OTHER INFORMATION: PLCD4, forward primer

<400> SEQUENCE: 81
tcagaatgac ggcatgacag t                                         21

<210> SEQ ID NO 82
<211> LENGTH: 20
<212> TYPE: DNA
<213> ORGANISM: Artificial sequence

```
<220> FEATURE:
<223> OTHER INFORMATION: PLCD4, reverse primer

<400> SEQUENCE: 82
ccctcgcatc catatctggg                                                   20

<210> SEQ ID NO 83
<211> LENGTH: 20
<212> TYPE: DNA
<213> ORGANISM: Artificial sequence
<220> FEATURE:
<223> OTHER INFORMATION: CXCL14, forward primer

<400> SEQUENCE: 83
cgtgtggacg ggtccaaatg                                                   20

<210> SEQ ID NO 84
<211> LENGTH: 20
<212> TYPE: DNA
<213> ORGANISM: Artificial sequence
<220> FEATURE:
<223> OTHER INFORMATION: CXCL14, reverse primer

<400> SEQUENCE: 84
tcgtagaccc tgcgcttctc                                                   20

<210> SEQ ID NO 85
<211> LENGTH: 19
<212> TYPE: DNA
<213> ORGANISM: Artificial sequence
<220> FEATURE:
<223> OTHER INFORMATION: ADRA1A, forward primer

<400> SEQUENCE: 85
ctccagcctg tcgcacaag                                                    19

<210> SEQ ID NO 86
<211> LENGTH: 21
<212> TYPE: DNA
<213> ORGANISM: Artificial sequence
<220> FEATURE:
<223> OTHER INFORMATION: ADRA1A, reverse primer

<400> SEQUENCE: 86
tgtagtcggc caattcgtag g                                                 21

<210> SEQ ID NO 87
<211> LENGTH: 21
<212> TYPE: DNA
<213> ORGANISM: Artificial sequence
<220> FEATURE:
<223> OTHER INFORMATION: ADRB1, forward primer

<400> SEQUENCE: 87
atcgagaccc tgtgtgtcat t                                                 21

<210> SEQ ID NO 88
<211> LENGTH: 22
<212> TYPE: DNA
<213> ORGANISM: Artificial sequence
<220> FEATURE:
<223> OTHER INFORMATION: ADRB1, reverse primer

<400> SEQUENCE: 88
gtagaaggag actacggacg ag                                                22
```

<210> SEQ ID NO 89
<211> LENGTH: 20
<212> TYPE: DNA
<213> ORGANISM: Artificial sequence
<220> FEATURE:
<223> OTHER INFORMATION: ADORA2B, forward primer

<400> SEQUENCE: 89
tgcactgact tctacggctg     20

<210> SEQ ID NO 90
<211> LENGTH: 19
<212> TYPE: DNA
<213> ORGANISM: Artificial sequence
<220> FEATURE:
<223> OTHER INFORMATION: ADORA2B, reverse primer

<400> SEQUENCE: 90
ggtccccgtg accaaactt     19

<210> SEQ ID NO 91
<211> LENGTH: 20
<212> TYPE: DNA
<213> ORGANISM: Artificial sequence
<220> FEATURE:
<223> OTHER INFORMATION: SYN 2, forward primer

<400> SEQUENCE: 91
ctgtcccaag cggtaaagca     20

<210> SEQ ID NO 92
<211> LENGTH: 21
<212> TYPE: DNA
<213> ORGANISM: Artificial sequence
<220> FEATURE:
<223> OTHER INFORMATION: SYN 2, reverse primer

<400> SEQUENCE: 92
ttctgcctgt tccaccttga t     21

<210> SEQ ID NO 93
<211> LENGTH: 19
<212> TYPE: DNA
<213> ORGANISM: Artificial sequence
<220> FEATURE:
<223> OTHER INFORMATION: SYT 1, forward primer

<400> SEQUENCE: 93
taggacccaa ctgagcagg     19

<210> SEQ ID NO 94
<211> LENGTH: 21
<212> TYPE: DNA
<213> ORGANISM: Artificial sequence
<220> FEATURE:
<223> OTHER INFORMATION: SYT 1, reverse primer

<400> SEQUENCE: 94
gggaagtcgg tctcactttt g     21

<210> SEQ ID NO 95
<211> LENGTH: 20
<212> TYPE: DNA
<213> ORGANISM: Artificial sequence
<220> FEATURE:
<223> OTHER INFORMATION: NRCAM, forward primer

```
<400> SEQUENCE: 95
tgaccctcgg gagaatattg                                              20

<210> SEQ ID NO 96
<211> LENGTH: 20
<212> TYPE: DNA
<213> ORGANISM: Artificial sequence
<220> FEATURE:
<223> OTHER INFORMATION: NRCAM, reverse primer

<400> SEQUENCE: 96
tggtccacaa tggtgatctg                                              20

<210> SEQ ID NO 97
<211> LENGTH: 21
<212> TYPE: DNA
<213> ORGANISM: Artificial sequence
<220> FEATURE:
<223> OTHER INFORMATION: OXTR, forward primer

<400> SEQUENCE: 97
ctgctacggc cttatcagct t                                            21

<210> SEQ ID NO 98
<211> LENGTH: 19
<212> TYPE: DNA
<213> ORGANISM: Artificial sequence
<220> FEATURE:
<223> OTHER INFORMATION: OXTR, reverse primer

<400> SEQUENCE: 98
cgctccacat ctgcacgaa                                               19

<210> SEQ ID NO 99
<211> LENGTH: 21
<212> TYPE: DNA
<213> ORGANISM: Artificial sequence
<220> FEATURE:
<223> OTHER INFORMATION: GPR 120, forward primer

<400> SEQUENCE: 99
cgatttgcac actgatttgg c                                            21

<210> SEQ ID NO 100
<211> LENGTH: 21
<212> TYPE: DNA
<213> ORGANISM: Artificial sequence
<220> FEATURE:
<223> OTHER INFORMATION: GPR 120, reverse primer

<400> SEQUENCE: 100
tgcacagtgt catgttgtag a                                            21

<210> SEQ ID NO 101
<211> LENGTH: 20
<212> TYPE: DNA
<213> ORGANISM: Artificial sequence
<220> FEATURE:
<223> OTHER INFORMATION: GPR 40, forward primer

<400> SEQUENCE: 101
gggtctggtc tttgggttgg                                              20

<210> SEQ ID NO 102
```

```
<211> LENGTH: 19
<212> TYPE: DNA
<213> ORGANISM: Artificial sequence
<220> FEATURE:
<223> OTHER INFORMATION: GPR 40, reverse primer

<400> SEQUENCE: 102
cagcccacgt agcagaagg                                                    19

<210> SEQ ID NO 103
<211> LENGTH: 22
<212> TYPE: DNA
<213> ORGANISM: Artificial sequence
<220> FEATURE:
<223> OTHER INFORMATION: CD36, forward primer

<400> SEQUENCE: 103
aagccaggta ttgcagttct tt                                                22

<210> SEQ ID NO 104
<211> LENGTH: 22
<212> TYPE: DNA
<213> ORGANISM: Artificial sequence
<220> FEATURE:
<223> OTHER INFORMATION: CD36, reverse primer

<400> SEQUENCE: 104
gcatttgctg atgtctagca ca                                                22

<210> SEQ ID NO 105
<211> LENGTH: 18
<212> TYPE: DNA
<213> ORGANISM: Artificial sequence
<220> FEATURE:
<223> OTHER INFORMATION: KCNC2, forward primer

<400> SEQUENCE: 105
acccctactc gtccagag                                                     18

<210> SEQ ID NO 106
<211> LENGTH: 22
<212> TYPE: DNA
<213> ORGANISM: Artificial sequence
<220> FEATURE:
<223> OTHER INFORMATION: KCNC2, reverse primer

<400> SEQUENCE: 106
acaacacttg tgccattgat ga                                                22

<210> SEQ ID NO 107
<211> LENGTH: 19
<212> TYPE: DNA
<213> ORGANISM: Artificial sequence
<220> FEATURE:
<223> OTHER INFORMATION: KCNQ1, forward primer

<400> SEQUENCE: 107
ggagccacac tctgctgtc                                                    19

<210> SEQ ID NO 108
<211> LENGTH: 23
<212> TYPE: DNA
<213> ORGANISM: Artificial sequence
<220> FEATURE:
<223> OTHER INFORMATION: KCNQ1, reverse primer

<400> SEQUENCE: 108
```
cttacagaac tgtcatagcc gtc                                           23

<210> SEQ ID NO 109
<211> LENGTH: 20
<212> TYPE: DNA
<213> ORGANISM: Artificial sequence
<220> FEATURE:
<223> OTHER INFORMATION: KCNH2, forward primer

<400> SEQUENCE: 109
caacctgggc gaccagatag                                               20

<210> SEQ ID NO 110
<211> LENGTH: 20
<212> TYPE: DNA
<213> ORGANISM: Artificial sequence
<220> FEATURE:
<223> OTHER INFORMATION: KCNH2, reverse primer

<400> SEQUENCE: 110
ggtgttggga gagacgttgc                                               20

<210> SEQ ID NO 111
<211> LENGTH: 19
<212> TYPE: DNA
<213> ORGANISM: Artificial sequence
<220> FEATURE:
<223> OTHER INFORMATION: GNG13, forward primer

<400> SEQUENCE: 111
ggagtgggac gtgccacag                                                19

<210> SEQ ID NO 112
<211> LENGTH: 20
<212> TYPE: DNA
<213> ORGANISM: Artificial sequence
<220> FEATURE:
<223> OTHER INFORMATION: GNG13, reverse primer

<400> SEQUENCE: 112
tggtgcattt gcccttttcc                                               20

<210> SEQ ID NO 113
<211> LENGTH: 19
<212> TYPE: DNA
<213> ORGANISM: Artificial sequence
<220> FEATURE:
<223> OTHER INFORMATION: GNB3, forward primer

<400> SEQUENCE: 113
aagtgcctcg caagatggg                                                19

<210> SEQ ID NO 114
<211> LENGTH: 23
<212> TYPE: DNA
<213> ORGANISM: Artificial sequence
<220> FEATURE:
<223> OTHER INFORMATION: GNB3, reverse primer

<400> SEQUENCE: 114
gcaggagaga taacctgtgt gag                                           23

<210> SEQ ID NO 115
<211> LENGTH: 20
<212> TYPE: DNA

```
<213> ORGANISM: Artificial sequence
<220> FEATURE:
<223> OTHER INFORMATION: GNA13, forward primer

<400> SEQUENCE: 115
cagcaacgca agtccaagga                                                      20

<210> SEQ ID NO 116
<211> LENGTH: 21
<212> TYPE: DNA
<213> ORGANISM: Artificial sequence
<220> FEATURE:
<223> OTHER INFORMATION: GNA13, reverse primer

<400> SEQUENCE: 116
ccagcaccct catacctttg a                                                    21

<210> SEQ ID NO 117
<211> LENGTH: 21
<212> TYPE: DNA
<213> ORGANISM: Artificial sequence
<220> FEATURE:
<223> OTHER INFORMATION: GNA11, forward primer

<400> SEQUENCE: 117
ggcttcacca agctcgtcta c                                                    21

<210> SEQ ID NO 118
<211> LENGTH: 20
<212> TYPE: DNA
<213> ORGANISM: Artificial sequence
<220> FEATURE:
<223> OTHER INFORMATION: GNA11, reverse primer

<400> SEQUENCE: 118
cactgacgta ctgatgctcg                                                      20

<210> SEQ ID NO 119
<211> LENGTH: 20
<212> TYPE: DNA
<213> ORGANISM: Artificial sequence
<220> FEATURE:
<223> OTHER INFORMATION: GNA14, forward primer

<400> SEQUENCE: 119
gagcgatgga cacgctaagg                                                      20

<210> SEQ ID NO 120
<211> LENGTH: 21
<212> TYPE: DNA
<213> ORGANISM: Artificial sequence
<220> FEATURE:
<223> OTHER INFORMATION: GNA14, reverse primer

<400> SEQUENCE: 120
tcctgtcgta acactcctgg a                                                    21

<210> SEQ ID NO 121
<211> LENGTH: 19
<212> TYPE: DNA
<213> ORGANISM: Artificial sequence
<220> FEATURE:
<223> OTHER INFORMATION: GNA12, forward primer

<400> SEQUENCE: 121
ccgcgagttc gaccagaag                                                       19
```

<210> SEQ ID NO 122
<211> LENGTH: 21
<212> TYPE: DNA
<213> ORGANISM: Artificial sequence
<220> FEATURE:
<223> OTHER INFORMATION: GNA12, reverse primer

<400> SEQUENCE: 122
tgatgccaga atccctccag a                                          21

<210> SEQ ID NO 123
<211> LENGTH: 23
<212> TYPE: DNA
<213> ORGANISM: Artificial sequence
<220> FEATURE:
<223> OTHER INFORMATION: GNB1, forward primer

<400> SEQUENCE: 123
atgcaactct ctctcagatc aca                                        23

<210> SEQ ID NO 124
<211> LENGTH: 19
<212> TYPE: DNA
<213> ORGANISM: Artificial sequence
<220> FEATURE:
<223> OTHER INFORMATION: GNB1, reverse primer

<400> SEQUENCE: 124
cgaggcactg acgagaagc                                             19

<210> SEQ ID NO 125
<211> LENGTH: 22
<212> TYPE: DNA
<213> ORGANISM: Artificial sequence
<220> FEATURE:
<223> OTHER INFORMATION: GNAL, forward primer

<400> SEQUENCE: 125
cacgtcaatg ggtttaatcc cg                                         22

<210> SEQ ID NO 126
<211> LENGTH: 23
<212> TYPE: DNA
<213> ORGANISM: Artificial sequence
<220> FEATURE:
<223> OTHER INFORMATION: GNAL, reverse primer

<400> SEQUENCE: 126
caaagtcagt gatagggact atg                                        23

<210> SEQ ID NO 127
<211> LENGTH: 21
<212> TYPE: DNA
<213> ORGANISM: Artificial sequence
<220> FEATURE:
<223> OTHER INFORMATION: GNA15, forward primer

<400> SEQUENCE: 127
gctcgattca gccgtgtact a                                          21

<210> SEQ ID NO 128
<211> LENGTH: 23
<212> TYPE: DNA
<213> ORGANISM: Artificial sequence
<220> FEATURE:

<223> OTHER INFORMATION: GNA15, reverse primer

<400> SEQUENCE: 128
ccatttctta cgctctgact tct       23

<210> SEQ ID NO 129
<211> LENGTH: 23
<212> TYPE: DNA
<213> ORGANISM: Artificial sequence
<220> FEATURE:
<223> OTHER INFORMATION: GNAQ, forward primer

<400> SEQUENCE: 129
tgggtcagga tactctgatg aag       23

<210> SEQ ID NO 130
<211> LENGTH: 21
<212> TYPE: DNA
<213> ORGANISM: Artificial sequence
<220> FEATURE:
<223> OTHER INFORMATION: GNAQ, reverse primer

<400> SEQUENCE: 130
tgtgcatgag ccttattgtg c       21

<210> SEQ ID NO 131
<211> LENGTH: 20
<212> TYPE: DNA
<213> ORGANISM: Artificial sequence
<220> FEATURE:
<223> OTHER INFORMATION: PANX1, forward primer

<400> SEQUENCE: 131
ccacggagta cgtgttctcg       20

<210> SEQ ID NO 132
<211> LENGTH: 20
<212> TYPE: DNA
<213> ORGANISM: Artificial sequence
<220> FEATURE:
<223> OTHER INFORMATION: PANX1, reverse primer

<400> SEQUENCE: 132
ccgcccagca atatgaatcc       20

<210> SEQ ID NO 133
<211> LENGTH: 22
<212> TYPE: DNA
<213> ORGANISM: Artificial sequence
<220> FEATURE:
<223> OTHER INFORMATION: ROMK, forward primer

<400> SEQUENCE: 133
atctggacaa cggtacttga cc       22

<210> SEQ ID NO 134
<211> LENGTH: 21
<212> TYPE: DNA
<213> ORGANISM: Artificial sequence
<220> FEATURE:
<223> OTHER INFORMATION: ROMK, reverse primer

<400> SEQUENCE: 134
tgcataccac aggagaccaa a       21

```
<210> SEQ ID NO 135
<211> LENGTH: 20
<212> TYPE: DNA
<213> ORGANISM: Artificial sequence
<220> FEATURE:
<223> OTHER INFORMATION: LEPR, forward primer

<400> SEQUENCE: 135
cttggtccag cccaccattg                                               20

<210> SEQ ID NO 136
<211> LENGTH: 19
<212> TYPE: DNA
<213> ORGANISM: Artificial sequence
<220> FEATURE:
<223> OTHER INFORMATION: LEPR, reverse primer

<400> SEQUENCE: 136
attcctgggc catccagtc                                                19

<210> SEQ ID NO 137
<211> LENGTH: 21
<212> TYPE: DNA
<213> ORGANISM: Artificial sequence
<220> FEATURE:
<223> OTHER INFORMATION: P2RY12, forward primer

<400> SEQUENCE: 137
cactgctcta cactgtcctg t                                             21

<210> SEQ ID NO 138
<211> LENGTH: 21
<212> TYPE: DNA
<213> ORGANISM: Artificial sequence
<220> FEATURE:
<223> OTHER INFORMATION: P2RY12, reverse primer

<400> SEQUENCE: 138
agtggtcctg ttcccagttt g                                             21

<210> SEQ ID NO 139
<211> LENGTH: 20
<212> TYPE: DNA
<213> ORGANISM: Artificial sequence
<220> FEATURE:
<223> OTHER INFORMATION: P2RX7, forward primer

<400> SEQUENCE: 139
acaccgcaga ctacaccttc                                               20

<210> SEQ ID NO 140
<211> LENGTH: 19
<212> TYPE: DNA
<213> ORGANISM: Artificial sequence
<220> FEATURE:
<223> OTHER INFORMATION: P2RX7, reverse primer

<400> SEQUENCE: 140
ggtgggatac tcgggacac                                                19

<210> SEQ ID NO 141
<211> LENGTH: 21
<212> TYPE: DNA
<213> ORGANISM: Artificial sequence
<220> FEATURE:
<223> OTHER INFORMATION: KCNA1, forward primer
```

<400> SEQUENCE: 141
catcgtggaa acgctgtgta t    21

<210> SEQ ID NO 142
<211> LENGTH: 21
<212> TYPE: DNA
<213> ORGANISM: Artificial sequence
<220> FEATURE:
<223> OTHER INFORMATION: KCNA1, reverse primer

<400> SEQUENCE: 142
aacccttacc aagcggatga c    21

<210> SEQ ID NO 143
<211> LENGTH: 20
<212> TYPE: DNA
<213> ORGANISM: Artificial sequence
<220> FEATURE:
<223> OTHER INFORMATION: KCNA2, forward primer

<400> SEQUENCE: 143
tagtggggtg accttccaca    20

<210> SEQ ID NO 144
<211> LENGTH: 19
<212> TYPE: DNA
<213> ORGANISM: Artificial sequence
<220> FEATURE:
<223> OTHER INFORMATION: KCNA2, reverse primer

<400> SEQUENCE: 144
ctgggacagg caaagaacc    19

<210> SEQ ID NO 145
<211> LENGTH: 20
<212> TYPE: DNA
<213> ORGANISM: Artificial sequence
<220> FEATURE:
<223> OTHER INFORMATION: KCNA3, forward primer

<400> SEQUENCE: 145
ttttctccag cgcggtctac    20

<210> SEQ ID NO 146
<211> LENGTH: 20
<212> TYPE: DNA
<213> ORGANISM: Artificial sequence
<220> FEATURE:
<223> OTHER INFORMATION: KCNA3, reverse primer

<400> SEQUENCE: 146
cgcgtccaca tcaacatctc    20

<210> SEQ ID NO 147
<211> LENGTH: 20
<212> TYPE: DNA
<213> ORGANISM: Artificial sequence
<220> FEATURE:
<223> OTHER INFORMATION: KCNA5, forward primer

<400> SEQUENCE: 147
cgcgtccaca tcaacatctc    20

<210> SEQ ID NO 148
<211> LENGTH: 21

```
<212> TYPE: DNA
<213> ORGANISM: Artificial sequence
<220> FEATURE:
<223> OTHER INFORMATION: KCNA5, reverse primer

<400> SEQUENCE: 148
ggtagaagcg tatctcgtcc g                                              21

<210> SEQ ID NO 149
<211> LENGTH: 23
<212> TYPE: DNA
<213> ORGANISM: Artificial sequence
<220> FEATURE:
<223> OTHER INFORMATION: KCNA6, forward primer

<400> SEQUENCE: 149
aggatgaaga cgattcctac aca                                            23

<210> SEQ ID NO 150
<211> LENGTH: 21
<212> TYPE: DNA
<213> ORGANISM: Artificial sequence
<220> FEATURE:
<223> OTHER INFORMATION: KCNA6, reverse primer

<400> SEQUENCE: 150
aggggaagat agccaccaag t                                              21

<210> SEQ ID NO 151
<211> LENGTH: 23
<212> TYPE: DNA
<213> ORGANISM: Artificial sequence
<220> FEATURE:
<223> OTHER INFORMATION: KCNB1, forward primer

<400> SEQUENCE: 151
ccattctgcc atactatgtc acc                                            23

<210> SEQ ID NO 152
<211> LENGTH: 21
<212> TYPE: DNA
<213> ORGANISM: Artificial sequence
<220> FEATURE:
<223> OTHER INFORMATION: KCNB1, reverse primer

<400> SEQUENCE: 152
agcaagccca actcattgta g                                              21

<210> SEQ ID NO 153
<211> LENGTH: 22
<212> TYPE: DNA
<213> ORGANISM: Artificial sequence
<220> FEATURE:
<223> OTHER INFORMATION: KCNB2, forward primer

<400> SEQUENCE: 153
gccaagaact tgattactgg gg                                             22

<210> SEQ ID NO 154
<211> LENGTH: 20
<212> TYPE: DNA
<213> ORGANISM: Artificial sequence
<220> FEATURE:
<223> OTHER INFORMATION: KCNB2, reverse primer

<400> SEQUENCE: 154
```

-continued ctctcgcata gtctctgcct                                          20

<210> SEQ ID NO 155
<211> LENGTH: 21
<212> TYPE: DNA
<213> ORGANISM: Artificial sequence
<220> FEATURE:
<223> OTHER INFORMATION: KCNC1, forward primer

<400> SEQUENCE: 155
gccccaacaa ggtagagttc a                                        21

<210> SEQ ID NO 156
<211> LENGTH: 21
<212> TYPE: DNA
<213> ORGANISM: Artificial sequence
<220> FEATURE:
<223> OTHER INFORMATION: KCNC1, reverse primer

<400> SEQUENCE: 156
tggcgggtca gcttaaagat g                                        21

<210> SEQ ID NO 157
<211> LENGTH: 20
<212> TYPE: DNA
<213> ORGANISM: Artificial sequence
<220> FEATURE:
<223> OTHER INFORMATION: CREB1, forward primer

<400> SEQUENCE: 157
ccactgtaac ggtgccaact                                          20

<210> SEQ ID NO 158
<211> LENGTH: 23
<212> TYPE: DNA
<213> ORGANISM: Artificial sequence
<220> FEATURE:
<223> OTHER INFORMATION: CREB1, reverse primer

<400> SEQUENCE: 158
gctgcattgg tcatggttaa tgt                                      23

<210> SEQ ID NO 159
<211> LENGTH: 22
<212> TYPE: DNA
<213> ORGANISM: Artificial sequence
<220> FEATURE:
<223> OTHER INFORMATION: PDE1A, forward primer

<400> SEQUENCE: 159
ttggcttcta cctttacacg ga                                       22

<210> SEQ ID NO 160
<211> LENGTH: 22
<212> TYPE: DNA
<213> ORGANISM: Artificial sequence
<220> FEATURE:
<223> OTHER INFORMATION: PDE1A, reverse primer

<400> SEQUENCE: 160
agggcaaata catcgaaaga cc                                       22

<210> SEQ ID NO 161
<211> LENGTH: 21
<212> TYPE: DNA
<213> ORGANISM: Artificial sequence

```
<220> FEATURE:
<223> OTHER INFORMATION: SCN2A, forward primer

<400> SEQUENCE: 161
tctaagcgtg tttgcgctaa t                                              21

<210> SEQ ID NO 162
<211> LENGTH: 23
<212> TYPE: DNA
<213> ORGANISM: Artificial sequence
<220> FEATURE:
<223> OTHER INFORMATION: SCN2A, reverse primer

<400> SEQUENCE: 162
accattccca tccaatgaat tgt                                            23

<210> SEQ ID NO 163
<211> LENGTH: 21
<212> TYPE: DNA
<213> ORGANISM: Artificial sequence
<220> FEATURE:
<223> OTHER INFORMATION: SCN3A, forward primer

<400> SEQUENCE: 163
ctgagcgtgt ttgctctcat t                                              21

<210> SEQ ID NO 164
<211> LENGTH: 23
<212> TYPE: DNA
<213> ORGANISM: Artificial sequence
<220> FEATURE:
<223> OTHER INFORMATION: SCN3A, reverse primer

<400> SEQUENCE: 164
gagtaaaggg tcttttgcc cat                                             23

<210> SEQ ID NO 165
<211> LENGTH: 22
<212> TYPE: DNA
<213> ORGANISM: Artificial sequence
<220> FEATURE:
<223> OTHER INFORMATION: SCN9A, forward primer

<400> SEQUENCE: 165
attcgtggct ccttgttttc tg                                             22

<210> SEQ ID NO 166
<211> LENGTH: 22
<212> TYPE: DNA
<213> ORGANISM: Artificial sequence
<220> FEATURE:
<223> OTHER INFORMATION: SCN9A, reverse primer

<400> SEQUENCE: 166
ctactggctt ggctgatgtt ac                                             22

<210> SEQ ID NO 167
<211> LENGTH: 22
<212> TYPE: DNA
<213> ORGANISM: Artificial sequence
<220> FEATURE:
<223> OTHER INFORMATION: ACCN1, forward primer

<400> SEQUENCE: 167
ggaaacgaca tttgaagcag ga                                             22
```

```
<210> SEQ ID NO 168
<211> LENGTH: 19
<212> TYPE: DNA
<213> ORGANISM: Artificial sequence
<220> FEATURE:
<223> OTHER INFORMATION: ACCN1, reverse primer

<400> SEQUENCE: 168
ctgaggatcg gcactcacc                                                  19

<210> SEQ ID NO 169
<211> LENGTH: 21
<212> TYPE: DNA
<213> ORGANISM: Artificial sequence
<220> FEATURE:
<223> OTHER INFORMATION: ACCN2, forward primer

<400> SEQUENCE: 169
acatgcgtga gttctacgac c                                               21

<210> SEQ ID NO 170
<211> LENGTH: 22
<212> TYPE: DNA
<213> ORGANISM: Artificial sequence
<220> FEATURE:
<223> OTHER INFORMATION: ACCN2, reverse primer

<400> SEQUENCE: 170
ttgaacgtgt agcactttcc at                                              22

<210> SEQ ID NO 171
<211> LENGTH: 20
<212> TYPE: DNA
<213> ORGANISM: Artificial sequence
<220> FEATURE:
<223> OTHER INFORMATION: ACCN3, forward primer

<400> SEQUENCE: 171
gagaaagcca ccggctcatc                                                 20

<210> SEQ ID NO 172
<211> LENGTH: 20
<212> TYPE: DNA
<213> ORGANISM: Artificial sequence
<220> FEATURE:
<223> OTHER INFORMATION: ACCN3, reverse primer

<400> SEQUENCE: 172
aagttctcag gcccacaagg                                                 20

<210> SEQ ID NO 173
<211> LENGTH: 19
<212> TYPE: DNA
<213> ORGANISM: Artificial sequence
<220> FEATURE:
<223> OTHER INFORMATION: HTR1A, forward primer

<400> SEQUENCE: 173
acctgcgacc tgttcatcg                                                  19

<210> SEQ ID NO 174
<211> LENGTH: 21
<212> TYPE: DNA
<213> ORGANISM: Artificial sequence
<220> FEATURE:
<223> OTHER INFORMATION: HTR1A, reverse primer
```

<400> SEQUENCE: 174
aggaagccaa taagccaagt g                                               21

<210> SEQ ID NO 175
<211> LENGTH: 22
<212> TYPE: DNA
<213> ORGANISM: Artificial sequence
<220> FEATURE:
<223> OTHER INFORMATION: HTR1B, forward primer

<400> SEQUENCE: 175
aactacctga tgcgcctctc tg                                              22

<210> SEQ ID NO 176
<211> LENGTH: 21
<212> TYPE: DNA
<213> ORGANISM: Artificial sequence
<220> FEATURE:
<223> OTHER INFORMATION: HTR1B, reverse primer

<400> SEQUENCE: 176
acaagtgatg tccgacgaca g                                               21

<210> SEQ ID NO 177
<211> LENGTH: 21
<212> TYPE: DNA
<213> ORGANISM: Artificial sequence
<220> FEATURE:
<223> OTHER INFORMATION: HTR1D, forward primer

<400> SEQUENCE: 177
ctccaacaga tccctgaatg c                                               21

<210> SEQ ID NO 178
<211> LENGTH: 21
<212> TYPE: DNA
<213> ORGANISM: Artificial sequence
<220> FEATURE:
<223> OTHER INFORMATION: HTR1D, reverse primer

<400> SEQUENCE: 178
cctggtgagt aagatggtgg t                                               21

<210> SEQ ID NO 179
<211> LENGTH: 20
<212> TYPE: DNA
<213> ORGANISM: Artificial sequence
<220> FEATURE:
<223> OTHER INFORMATION: HTR1E, forward primer

<400> SEQUENCE: 179
ctgggctcaa cgtactccag                                                 20

<210> SEQ ID NO 180
<211> LENGTH: 20
<212> TYPE: DNA
<213> ORGANISM: Artificial sequence
<220> FEATURE:
<223> OTHER INFORMATION: HTR1E, reverse primer

<400> SEQUENCE: 180
gccacagcat ttcttctgag                                                 20

<210> SEQ ID NO 181

-continued

```
<211> LENGTH: 23
<212> TYPE: DNA
<213> ORGANISM: Artificial sequence
<220> FEATURE:
<223> OTHER INFORMATION: HTR2A, forward primer

<400> SEQUENCE: 181
ctttgtgcag tctggattta cct                                              23

<210> SEQ ID NO 182
<211> LENGTH: 23
<212> TYPE: DNA
<213> ORGANISM: Artificial sequence
<220> FEATURE:
<223> OTHER INFORMATION: HTR2A, reverse primer

<400> SEQUENCE: 182
actgatatgg tccaaacagc aat                                              23

<210> SEQ ID NO 183
<211> LENGTH: 23
<212> TYPE: DNA
<213> ORGANISM: Artificial sequence
<220> FEATURE:
<223> OTHER INFORMATION: HTR2B, forward primer

<400> SEQUENCE: 183
cttgacgttc tcttttcaac cgc                                              23

<210> SEQ ID NO 184
<211> LENGTH: 23
<212> TYPE: DNA
<213> ORGANISM: Artificial sequence
<220> FEATURE:
<223> OTHER INFORMATION: HTR2B, reverse primer

<400> SEQUENCE: 184
tcttaatgtc cctagccatt gct                                              23

<210> SEQ ID NO 185
<211> LENGTH: 23
<212> TYPE: DNA
<213> ORGANISM: Artificial sequence
<220> FEATURE:
<223> OTHER INFORMATION: HTR2C, forward primer

<400> SEQUENCE: 185
tcttaatgtc cctagccatt gct                                              23

<210> SEQ ID NO 186
<211> LENGTH: 20
<212> TYPE: DNA
<213> ORGANISM: Artificial sequence
<220> FEATURE:
<223> OTHER INFORMATION: HTR2C, reverse primer

<400> SEQUENCE: 186
ccagcgatat agcgcagagg                                                  20

<210> SEQ ID NO 187
<211> LENGTH: 21
<212> TYPE: DNA
<213> ORGANISM: Artificial sequence
<220> FEATURE:
<223> OTHER INFORMATION: HTR3A, forward primer

<400> SEQUENCE: 187
```
gaagccaacc accgtatcca t                                              21

<210> SEQ ID NO 188
<211> LENGTH: 22
<212> TYPE: DNA
<213> ORGANISM: Artificial sequence
<220> FEATURE:
<223> OTHER INFORMATION: HTR3A, reverse primer

<400> SEQUENCE: 188
ccacatccac gaactcattg at                                             22

<210> SEQ ID NO 189
<211> LENGTH: 21
<212> TYPE: DNA
<213> ORGANISM: Artificial sequence
<220> FEATURE:
<223> OTHER INFORMATION: HTR3B, forward primer

<400> SEQUENCE: 189
ggtctctgcg tgcagtttag a                                              21

<210> SEQ ID NO 190
<211> LENGTH: 23
<212> TYPE: DNA
<213> ORGANISM: Artificial sequence
<220> FEATURE:
<223> OTHER INFORMATION: HTR3B, reverse primer

<400> SEQUENCE: 190
aggacacaga tagaagttcc cac                                            23

<210> SEQ ID NO 191
<211> LENGTH: 22
<212> TYPE: DNA
<213> ORGANISM: Artificial sequence
<220> FEATURE:
<223> OTHER INFORMATION: HTR3C, forward primer

<400> SEQUENCE: 191
ttccggtctc actgcctata tc                                             22

<210> SEQ ID NO 192
<211> LENGTH: 23
<212> TYPE: DNA
<213> ORGANISM: Artificial sequence
<220> FEATURE:
<223> OTHER INFORMATION: HTR3C, reverse primer

<400> SEQUENCE: 192
aaggtgaagg tacagttctg ttg                                            23

<210> SEQ ID NO 193
<211> LENGTH: 22
<212> TYPE: DNA
<213> ORGANISM: Artificial sequence
<220> FEATURE:
<223> OTHER INFORMATION: HTR3D, forward primer

<400> SEQUENCE: 193
ccctacgtgg taaactttct gg                                             22

<210> SEQ ID NO 194
<211> LENGTH: 21
<212> TYPE: DNA

```
<213> ORGANISM: Artificial sequence
<220> FEATURE:
<223> OTHER INFORMATION: HTR3D, reverse primer

<400> SEQUENCE: 194
tgtgatgaag tgctagtggc t                                              21

<210> SEQ ID NO 195
<211> LENGTH: 19
<212> TYPE: DNA
<213> ORGANISM: Artificial sequence
<220> FEATURE:
<223> OTHER INFORMATION: HTR3E, forward primer

<400> SEQUENCE: 195
agacgcatcc cggaacatc                                                 19

<210> SEQ ID NO 196
<211> LENGTH: 21
<212> TYPE: DNA
<213> ORGANISM: Artificial sequence
<220> FEATURE:
<223> OTHER INFORMATION: HTR3E, reverse primer

<400> SEQUENCE: 196
ggcacgagaa ggtttatgac a                                              21

<210> SEQ ID NO 197
<211> LENGTH: 19
<212> TYPE: DNA
<213> ORGANISM: Artificial sequence
<220> FEATURE:
<223> OTHER INFORMATION: HTR4, forward primer

<400> SEQUENCE: 197
tgccctttgg tgcaattga                                                 19

<210> SEQ ID NO 198
<211> LENGTH: 22
<212> TYPE: DNA
<213> ORGANISM: Artificial sequence
<220> FEATURE:
<223> OTHER INFORMATION: HTR4, reverse primer

<400> SEQUENCE: 198
cagaggggtc atcttgttcc ta                                             22

<210> SEQ ID NO 199
<211> LENGTH: 19
<212> TYPE: DNA
<213> ORGANISM: Artificial sequence
<220> FEATURE:
<223> OTHER INFORMATION: HTR5A, forward primer

<400> SEQUENCE: 199
taagccgcga gccttccta                                                 19

<210> SEQ ID NO 200
<211> LENGTH: 21
<212> TYPE: DNA
<213> ORGANISM: Artificial sequence
<220> FEATURE:
<223> OTHER INFORMATION: HTR5A, reverse primer

<400> SEQUENCE: 200
gggtgagacg ctattggtct t                                              21
```

<210> SEQ ID NO 201
<211> LENGTH: 19
<212> TYPE: DNA
<213> ORGANISM: Artificial sequence
<220> FEATURE:
<223> OTHER INFORMATION: HTR6, forward primer

<400> SEQUENCE: 201
caggcgtcta gccacgaag                                                    19

<210> SEQ ID NO 202
<211> LENGTH: 22
<212> TYPE: DNA
<213> ORGANISM: Artificial sequence
<220> FEATURE:
<223> OTHER INFORMATION: HTR6, reverse primer

<400> SEQUENCE: 202
ccatgtgagg acatcgaaga gg                                                22

<210> SEQ ID NO 203
<211> LENGTH: 21
<212> TYPE: DNA
<213> ORGANISM: Artificial sequence
<220> FEATURE:
<223> OTHER INFORMATION: HTR7, forward primer

<400> SEQUENCE: 203
cacctccgct ctttccttct g                                                 21

<210> SEQ ID NO 204
<211> LENGTH: 21
<212> TYPE: DNA
<213> ORGANISM: Artificial sequence
<220> FEATURE:
<223> OTHER INFORMATION: HTR7, reverse primer

<400> SEQUENCE: 204
cgtagttgat ctgttcccca c                                                 21

<210> SEQ ID NO 205
<211> LENGTH: 19
<212> TYPE: DNA
<213> ORGANISM: Artificial sequence
<220> FEATURE:
<223> OTHER INFORMATION: TRPM8, forward primer

<400> SEQUENCE: 205
gcaagtgtgg ctatgccca                                                    19

<210> SEQ ID NO 206
<211> LENGTH: 19
<212> TYPE: DNA
<213> ORGANISM: Artificial sequence
<220> FEATURE:
<223> OTHER INFORMATION: TRPM8, reverse primer

<400> SEQUENCE: 206
ccaaaggcgt cggtcggaa                                                    19

<210> SEQ ID NO 207
<211> LENGTH: 22
<212> TYPE: DNA
<213> ORGANISM: Artificial sequence
<220> FEATURE:

<223> OTHER INFORMATION: TRPA1, forward primer

<400> SEQUENCE: 207
tgtgacgata tggacaccatt ct                                              22

<210> SEQ ID NO 208
<211> LENGTH: 23
<212> TYPE: DNA
<213> ORGANISM: Artificial sequence
<220> FEATURE:
<223> OTHER INFORMATION: TRPA1, reverse primer

<400> SEQUENCE: 208
ttgaagtttc ggagatttgg gtt                                              23

<210> SEQ ID NO 209
<211> LENGTH: 21
<212> TYPE: DNA
<213> ORGANISM: Artificial sequence
<220> FEATURE:
<223> OTHER INFORMATION: CD73, forward primer

<400> SEQUENCE: 209
gcctgggagc ttacgatttt g                                                21

<210> SEQ ID NO 210
<211> LENGTH: 20
<212> TYPE: DNA
<213> ORGANISM: Artificial sequence
<220> FEATURE:
<223> OTHER INFORMATION: CD73, reverse primer

<400> SEQUENCE: 210
ggtgaaccag atagtgccct                                                  20

<210> SEQ ID NO 211
<211> LENGTH: 23
<212> TYPE: DNA
<213> ORGANISM: Artificial sequence
<220> FEATURE:
<223> OTHER INFORMATION: ACPP, forward primer

<400> SEQUENCE: 211
ccccataaag gaatcctcat ggc                                              23

<210> SEQ ID NO 212
<211> LENGTH: 21
<212> TYPE: DNA
<213> ORGANISM: Artificial sequence
<220> FEATURE:
<223> OTHER INFORMATION: ACPP, reverse primer

<400> SEQUENCE: 212
tcaaagtccg gtcaacgtct g                                                21

<210> SEQ ID NO 213
<211> LENGTH: 20
<212> TYPE: DNA
<213> ORGANISM: Artificial sequence
<220> FEATURE:
<223> OTHER INFORMATION: P2RX2, forward primer

<400> SEQUENCE: 213
ctgcctcgtc aggctacaac                                                  20

-continued

```
<210> SEQ ID NO 214
<211> LENGTH: 21
<212> TYPE: DNA
<213> ORGANISM: Artificial sequence
<220> FEATURE:
<223> OTHER INFORMATION: P2RX2, reverse primer

<400> SEQUENCE: 214
gtgggaatca ggctgaactt c                                              21

<210> SEQ ID NO 215
<211> LENGTH: 19
<212> TYPE: DNA
<213> ORGANISM: Artificial sequence
<220> FEATURE:
<223> OTHER INFORMATION: P2RX3, forward primer

<400> SEQUENCE: 215
atgcgccttg accaagacg                                                 19

<210> SEQ ID NO 216
<211> LENGTH: 20
<212> TYPE: DNA
<213> ORGANISM: Artificial sequence
<220> FEATURE:
<223> OTHER INFORMATION: P2RX3, reverse primer

<400> SEQUENCE: 216
ggccagagcc aaattgaaca                                                20

<210> SEQ ID NO 217
<211> LENGTH: 21
<212> TYPE: DNA
<213> ORGANISM: Artificial sequence
<220> FEATURE:
<223> OTHER INFORMATION: FAM38A, forward primer

<400> SEQUENCE: 217
atgttgctct cacccctgac c                                              21

<210> SEQ ID NO 218
<211> LENGTH: 22
<212> TYPE: DNA
<213> ORGANISM: Artificial sequence
<220> FEATURE:
<223> OTHER INFORMATION: FAM38A, reverse primer

<400> SEQUENCE: 218
ccagcacaca catagatcca gt                                             22

<210> SEQ ID NO 219
<211> LENGTH: 20
<212> TYPE: DNA
<213> ORGANISM: Artificial sequence
<220> FEATURE:
<223> OTHER INFORMATION: FAM38B, forward primer

<400> SEQUENCE: 219
cacgttggtg agccttgaag                                                20

<210> SEQ ID NO 220
<211> LENGTH: 21
<212> TYPE: DNA
<213> ORGANISM: Artificial sequence
<220> FEATURE:
<223> OTHER INFORMATION: FAM38B, reverse primer
```

<400> SEQUENCE: 220
tcaaactccg ggttactctg t                                              21

<210> SEQ ID NO 221
<211> LENGTH: 20
<212> TYPE: DNA
<213> ORGANISM: Artificial sequence
<220> FEATURE:
<223> OTHER INFORMATION: HTR1F, forward primer

<400> SEQUENCE: 221
tgtctgggct ggcactgatg                                                20

<210> SEQ ID NO 222
<211> LENGTH: 20
<212> TYPE: DNA
<213> ORGANISM: Artificial sequence
<220> FEATURE:
<223> OTHER INFORMATION: HTR1F, reverse primer

<400> SEQUENCE: 222
acaatgctga agggcatcac                                                20

<210> SEQ ID NO 223
<211> LENGTH: 21
<212> TYPE: DNA
<213> ORGANISM: Artificial sequence
<220> FEATURE:
<223> OTHER INFORMATION: Tbp, forward primer

<400> SEQUENCE: 223
ccactcacag actctcacaa c                                              21

<210> SEQ ID NO 224
<211> LENGTH: 21
<212> TYPE: DNA
<213> ORGANISM: Artificial sequence
<220> FEATURE:
<223> OTHER INFORMATION: Tbp, reverse primer

<400> SEQUENCE: 224
ctgcggtaca atcccagaac t                                              21

<210> SEQ ID NO 225
<211> LENGTH: 23
<212> TYPE: DNA
<213> ORGANISM: Artificial sequence
<220> FEATURE:
<223> OTHER INFORMATION: T2R1, forward primer

<400> SEQUENCE: 225
atcatgtgtt ctgcgaattg tgc                                            23

<210> SEQ ID NO 226
<211> LENGTH: 23
<212> TYPE: DNA
<213> ORGANISM: Artificial sequence
<220> FEATURE:
<223> OTHER INFORMATION: T2R1, reverse primer

<400> SEQUENCE: 226
accataaacc ctgcatattt gct                                            23

<210> SEQ ID NO 227
<211> LENGTH: 21

```
<212> TYPE: DNA
<213> ORGANISM: Artificial sequence
<220> FEATURE:
<223> OTHER INFORMATION: T2R2, forward primer

<400> SEQUENCE: 227
cagcctatgg tttgccactt g                                      21

<210> SEQ ID NO 228
<211> LENGTH: 20
<212> TYPE: DNA
<213> ORGANISM: Artificial sequence
<220> FEATURE:
<223> OTHER INFORMATION: T2R2, reverse primer

<400> SEQUENCE: 228
ctgagggcat cctcttccac                                        20

<210> SEQ ID NO 229
<211> LENGTH: 22
<212> TYPE: DNA
<213> ORGANISM: Artificial sequence
<220> FEATURE:
<223> OTHER INFORMATION: T2R3, forward primer

<400> SEQUENCE: 229
tatcctgtgg tagtaccgca tc                                     22

<210> SEQ ID NO 230
<211> LENGTH: 21
<212> TYPE: DNA
<213> ORGANISM: Artificial sequence
<220> FEATURE:
<223> OTHER INFORMATION: T2R3, reverse primer

<400> SEQUENCE: 230
gggacacaat taagggaggc a                                      21

<210> SEQ ID NO 231
<211> LENGTH: 23
<212> TYPE: DNA
<213> ORGANISM: Artificial sequence
<220> FEATURE:
<223> OTHER INFORMATION: T2R4, forward primer

<400> SEQUENCE: 231
ttcctgaact tgtgactacg aga                                    23

<210> SEQ ID NO 232
<211> LENGTH: 23
<212> TYPE: DNA
<213> ORGANISM: Artificial sequence
<220> FEATURE:
<223> OTHER INFORMATION: T2R4, reverse primer

<400> SEQUENCE: 232
cctcaaggag tgtattagca agg                                    23

<210> SEQ ID NO 233
<211> LENGTH: 21
<212> TYPE: DNA
<213> ORGANISM: Artificial sequence
<220> FEATURE:
<223> OTHER INFORMATION: T2R5, forward primer

<400> SEQUENCE: 233
```

```
gccgttggct tcgctatctt a                                             21
```

<210> SEQ ID NO 234
<211> LENGTH: 22
<212> TYPE: DNA
<213> ORGANISM: Artificial sequence
<220> FEATURE:
<223> OTHER INFORMATION: T2R5, reverse primer

<400> SEQUENCE: 234

```
agactcaggt tataggccct ct                                            22
```

<210> SEQ ID NO 235
<211> LENGTH: 22
<212> TYPE: DNA
<213> ORGANISM: Artificial sequence
<220> FEATURE:
<223> OTHER INFORMATION: T2R7, forward primer

<400> SEQUENCE: 235

```
tgaagtggag aattgacagg gt                                            22
```

<210> SEQ ID NO 236
<211> LENGTH: 23
<212> TYPE: DNA
<213> ORGANISM: Artificial sequence
<220> FEATURE:
<223> OTHER INFORMATION: T2R7, reverse primer

<400> SEQUENCE: 236

```
tgccaggttg agaaataact tgg                                           23
```

<210> SEQ ID NO 237
<211> LENGTH: 22
<212> TYPE: DNA
<213> ORGANISM: Artificial sequence
<220> FEATURE:
<223> OTHER INFORMATION: T2R8, forward primer

<400> SEQUENCE: 237

```
cttgttggtc agccttatag ca                                            22
```

<210> SEQ ID NO 238
<211> LENGTH: 22
<212> TYPE: DNA
<213> ORGANISM: Artificial sequence
<220> FEATURE:
<223> OTHER INFORMATION: T2R8, reverse primer

<400> SEQUENCE: 238

```
actgccggta gcatagagtt tt                                            22
```

<210> SEQ ID NO 239
<211> LENGTH: 21
<212> TYPE: DNA
<213> ORGANISM: Artificial sequence
<220> FEATURE:
<223> OTHER INFORMATION: T2R9, forward primer

<400> SEQUENCE: 239

```
caaggtcatg cttgcgattc t                                             21
```

<210> SEQ ID NO 240
<211> LENGTH: 23
<212> TYPE: DNA
<213> ORGANISM: Artificial sequence

```
<220> FEATURE:
<223> OTHER INFORMATION: T2R9, reverse primer

<400> SEQUENCE: 240
cttggtgtgt ctaactaggg aga                                            23

<210> SEQ ID NO 241
<211> LENGTH: 22
<212> TYPE: DNA
<213> ORGANISM: Artificial sequence
<220> FEATURE:
<223> OTHER INFORMATION: T2R10, forward primer

<400> SEQUENCE: 241
ctacgtgtag tggaaggcat ct                                             22

<210> SEQ ID NO 242
<211> LENGTH: 22
<212> TYPE: DNA
<213> ORGANISM: Artificial sequence
<220> FEATURE:
<223> OTHER INFORMATION: T2R10, reverse primer

<400> SEQUENCE: 242
tcaattaggt taccggaggc at                                             22

<210> SEQ ID NO 243
<211> LENGTH: 21
<212> TYPE: DNA
<213> ORGANISM: Artificial sequence
<220> FEATURE:
<223> OTHER INFORMATION: T2R13, forward primer

<400> SEQUENCE: 243
ttggcaatct ccagaattgg g                                              21

<210> SEQ ID NO 244
<211> LENGTH: 23
<212> TYPE: DNA
<213> ORGANISM: Artificial sequence
<220> FEATURE:
<223> OTHER INFORMATION: T2R13, reverse primer

<400> SEQUENCE: 244
gggctagaga aactcgctat ttt                                            23

<210> SEQ ID NO 245
<211> LENGTH: 22
<212> TYPE: DNA
<213> ORGANISM: Artificial sequence
<220> FEATURE:
<223> OTHER INFORMATION: T2R14, forward primer

<400> SEQUENCE: 245
atgggtggtg tcataaagag ca                                             22

<210> SEQ ID NO 246
<211> LENGTH: 22
<212> TYPE: DNA
<213> ORGANISM: Artificial sequence
<220> FEATURE:
<223> OTHER INFORMATION: T2R14, reverse primer

<400> SEQUENCE: 246
aggctaattc gagagattgc ca                                             22
```

```
<210> SEQ ID NO 247
<211> LENGTH: 20
<212> TYPE: DNA
<213> ORGANISM: Artificial sequence
<220> FEATURE:
<223> OTHER INFORMATION: T2R16, forward primer

<400> SEQUENCE: 247
tgtgcagagc agcctaattg                                             20

<210> SEQ ID NO 248
<211> LENGTH: 20
<212> TYPE: DNA
<213> ORGANISM: Artificial sequence
<220> FEATURE:
<223> OTHER INFORMATION: T2R16, reverse primer

<400> SEQUENCE: 248
tgcagtagaa cacggtaagc                                             20

<210> SEQ ID NO 249
<211> LENGTH: 20
<212> TYPE: DNA
<213> ORGANISM: Artificial sequence
<220> FEATURE:
<223> OTHER INFORMATION: TAS2R38, forward primer

<400> SEQUENCE: 249
tccctgggaa ggcacatgag                                             20

<210> SEQ ID NO 250
<211> LENGTH: 20
<212> TYPE: DNA
<213> ORGANISM: Artificial sequence
<220> FEATURE:
<223> OTHER INFORMATION: TAS2R38, reverse primer

<400> SEQUENCE: 250
cagcacagtg tccgggaatc                                             20

<210> SEQ ID NO 251
<211> LENGTH: 21
<212> TYPE: DNA
<213> ORGANISM: Artificial sequence
<220> FEATURE:
<223> OTHER INFORMATION: T2R39, forward primer

<400> SEQUENCE: 251
tcctccagac accaaagaga a                                           21

<210> SEQ ID NO 252
<211> LENGTH: 22
<212> TYPE: DNA
<213> ORGANISM: Artificial sequence
<220> FEATURE:
<223> OTHER INFORMATION: T2R39, reverse primer

<400> SEQUENCE: 252
ccacttgtgg aaactgcctt at                                          22

<210> SEQ ID NO 253
<211> LENGTH: 23
<212> TYPE: DNA
<213> ORGANISM: Artificial sequence
<220> FEATURE:
<223> OTHER INFORMATION: T2R40, forward primer
```

```
<400> SEQUENCE: 253
tgaatagctc cattcctatc ccc                                              23

<210> SEQ ID NO 254
<211> LENGTH: 20
<212> TYPE: DNA
<213> ORGANISM: Artificial sequence
<220> FEATURE:
<223> OTHER INFORMATION: T2R40, reverse primer

<400> SEQUENCE: 254
gcccctatgt gagccttcat                                                  20

<210> SEQ ID NO 255
<211> LENGTH: 23
<212> TYPE: DNA
<213> ORGANISM: Artificial sequence
<220> FEATURE:
<223> OTHER INFORMATION: T2R41, forward primer

<400> SEQUENCE: 255
cacaacttct actactctgc cca                                              23

<210> SEQ ID NO 256
<211> LENGTH: 23
<212> TYPE: DNA
<213> ORGANISM: Artificial sequence
<220> FEATURE:
<223> OTHER INFORMATION: T2R41, reverse primer

<400> SEQUENCE: 256
agcagggtta tgatgaagga gat                                              23

<210> SEQ ID NO 257
<211> LENGTH: 23
<212> TYPE: DNA
<213> ORGANISM: Artificial sequence
<220> FEATURE:
<223> OTHER INFORMATION: T2R42, forward primer

<400> SEQUENCE: 257
ttctgtcctt ggtgagacat act                                              23

<210> SEQ ID NO 258
<211> LENGTH: 22
<212> TYPE: DNA
<213> ORGANISM: Artificial sequence
<220> FEATURE:
<223> OTHER INFORMATION: T2R42, reverse primer

<400> SEQUENCE: 258
gcacgaggga aaggcattta ag                                               22

<210> SEQ ID NO 259
<211> LENGTH: 20
<212> TYPE: DNA
<213> ORGANISM: Artificial sequence
<220> FEATURE:
<223> OTHER INFORMATION: T2R43, forward primer

<400> SEQUENCE: 259
tggcttgcta ctaccctcag                                                  20

<210> SEQ ID NO 260
```

```
<211> LENGTH: 20
<212> TYPE: DNA
<213> ORGANISM: Artificial sequence
<220> FEATURE:
<223> OTHER INFORMATION: T2R43, reverse primer

<400> SEQUENCE: 260
tggagctgca tcttcttgag                                               20

<210> SEQ ID NO 261
<211> LENGTH: 20
<212> TYPE: DNA
<213> ORGANISM: Artificial sequence
<220> FEATURE:
<223> OTHER INFORMATION: TAS2R44, forward primer

<400> SEQUENCE: 261
cagatgcgac tgtaaccacg                                               20

<210> SEQ ID NO 262
<211> LENGTH: 21
<212> TYPE: DNA
<213> ORGANISM: Artificial sequence
<220> FEATURE:
<223> OTHER INFORMATION: TAS2R44, reverse primer

<400> SEQUENCE: 262
agtacctcac ttgccgcaaa a                                             21

<210> SEQ ID NO 263
<211> LENGTH: 20
<212> TYPE: DNA
<213> ORGANISM: Artificial sequence
<220> FEATURE:
<223> OTHER INFORMATION: T2R45, forward primer

<400> SEQUENCE: 263
attccaccga gtgggtgaag                                               20

<210> SEQ ID NO 264
<211> LENGTH: 20
<212> TYPE: DNA
<213> ORGANISM: Artificial sequence
<220> FEATURE:
<223> OTHER INFORMATION: T2R45, reverse primer

<400> SEQUENCE: 264
gcaccaccag aatgacactc                                               20

<210> SEQ ID NO 265
<211> LENGTH: 21
<212> TYPE: DNA
<213> ORGANISM: Artificial sequence
<220> FEATURE:
<223> OTHER INFORMATION: T2R46, forward primer

<400> SEQUENCE: 265
acaacggtaa ccatcctagc a                                             21

<210> SEQ ID NO 266
<211> LENGTH: 21
<212> TYPE: DNA
<213> ORGANISM: Artificial sequence
<220> FEATURE:
<223> OTHER INFORMATION: T2R46, reverse primer

<400> SEQUENCE: 266
```

```
tgaatgcaat agcttcgcag a                                          21

<210> SEQ ID NO 267
<211> LENGTH: 23
<212> TYPE: DNA
<213> ORGANISM: Artificial sequence
<220> FEATURE:
<223> OTHER INFORMATION: T2R47, forward primer

<400> SEQUENCE: 267
acatggatga gactgtatgg aca                                        23

<210> SEQ ID NO 268
<211> LENGTH: 23
<212> TYPE: DNA
<213> ORGANISM: Artificial sequence
<220> FEATURE:
<223> OTHER INFORMATION: T2R47, reverse primer

<400> SEQUENCE: 268
tggcacataa cagaagaaag gag                                        23

<210> SEQ ID NO 269
<211> LENGTH: 21
<212> TYPE: DNA
<213> ORGANISM: Artificial sequence
<220> FEATURE:
<223> OTHER INFORMATION: T2R48, forward primer

<400> SEQUENCE: 269
gaagatgcgg ctccatagca a                                          21

<210> SEQ ID NO 270
<211> LENGTH: 21
<212> TYPE: DNA
<213> ORGANISM: Artificial sequence
<220> FEATURE:
<223> OTHER INFORMATION: T2R48, reverse primer

<400> SEQUENCE: 270
tggcaaagca ggagtacaag t                                          21

<210> SEQ ID NO 271
<211> LENGTH: 23
<212> TYPE: DNA
<213> ORGANISM: Artificial sequence
<220> FEATURE:
<223> OTHER INFORMATION: T2R49, forward primer

<400> SEQUENCE: 271
aaggctaaga gtgtagttct ggt                                        23

<210> SEQ ID NO 272
<211> LENGTH: 21
<212> TYPE: DNA
<213> ORGANISM: Artificial sequence
<220> FEATURE:
<223> OTHER INFORMATION: T2R49, reverse primer

<400> SEQUENCE: 272
agttggaaag gtgcattgca t                                          21

<210> SEQ ID NO 273
<211> LENGTH: 20
<212> TYPE: DNA
```

```
<213> ORGANISM: Artificial sequence
<220> FEATURE:
<223> OTHER INFORMATION: T2R50, forward primer

<400> SEQUENCE: 273
tctggcggtc tccagaattg                                               20

<210> SEQ ID NO 274
<211> LENGTH: 20
<212> TYPE: DNA
<213> ORGANISM: Artificial sequence
<220> FEATURE:
<223> OTHER INFORMATION: T2R50, reverse primer

<400> SEQUENCE: 274
ctgcccacat actctcatcc                                               20

<210> SEQ ID NO 275
<211> LENGTH: 21
<212> TYPE: DNA
<213> ORGANISM: Artificial sequence
<220> FEATURE:
<223> OTHER INFORMATION: T2R60, forward primer

<400> SEQUENCE: 275
gggtgctacg gagaatgttg t                                             21

<210> SEQ ID NO 276
<211> LENGTH: 21
<212> TYPE: DNA
<213> ORGANISM: Artificial sequence
<220> FEATURE:
<223> OTHER INFORMATION: T2R60, reverse primer

<400> SEQUENCE: 276
tagaggacca taaggtggca g                                             21

<210> SEQ ID NO 277
<211> LENGTH: 22
<212> TYPE: DNA
<213> ORGANISM: Artificial sequence
<220> FEATURE:
<223> OTHER INFORMATION: TAS2R38, forward primer

<400> SEQUENCE: 277
ctgctgttcc tgagtgctat cc                                            22

<210> SEQ ID NO 278
<211> LENGTH: 20
<212> TYPE: DNA
<213> ORGANISM: Artificial sequence
<220> FEATURE:
<223> OTHER INFORMATION: TAS2R38, reverse primer

<400> SEQUENCE: 278
cagaggttgg cttggtttgc                                               20

<210> SEQ ID NO 279
<211> LENGTH: 20
<212> TYPE: DNA
<213> ORGANISM: Artificial sequence
<220> FEATURE:
<223> OTHER INFORMATION: Topoisomerase I, forward primer

<400> SEQUENCE: 279
ccagacggaa gctcggaaac                                               20
```

<210> SEQ ID NO 280
<211> LENGTH: 22
<212> TYPE: DNA
<213> ORGANISM: Artificial sequence
<220> FEATURE:
<223> OTHER INFORMATION: Topoisomerase I, reverse primer

<400> SEQUENCE: 280
gtccaggagg ctctatcttg aa                                              22

<210> SEQ ID NO 281
<211> LENGTH: 20
<212> TYPE: DNA
<213> ORGANISM: Artificial sequence
<220> FEATURE:
<223> OTHER INFORMATION: hTERT, forward primer

<400> SEQUENCE: 281
aaccttcctc agctatgccc                                                 20

<210> SEQ ID NO 282
<211> LENGTH: 20
<212> TYPE: DNA
<213> ORGANISM: Artificial sequence
<220> FEATURE:
<223> OTHER INFORMATION: hTERT, reverse primer

<400> SEQUENCE: 282
gtttgcgacg catgttcctc                                                 20

<210> SEQ ID NO 283
<211> LENGTH: 20
<212> TYPE: DNA
<213> ORGANISM: Artificial sequence
<220> FEATURE:
<223> OTHER INFORMATION: large T, forward primer

<400> SEQUENCE: 283
cactgcaggc cagatttgta                                                 20

<210> SEQ ID NO 284
<211> LENGTH: 20
<212> TYPE: DNA
<213> ORGANISM: Artificial sequence
<220> FEATURE:
<223> OTHER INFORMATION: large T, reverse primer

<400> SEQUENCE: 284
caaagcaatg ccactttgaa                                                 20

<210> SEQ ID NO 285
<211> LENGTH: 21
<212> TYPE: DNA
<213> ORGANISM: Artificial sequence
<220> FEATURE:
<223> OTHER INFORMATION: Cyclophilin A, forward primer

<400> SEQUENCE: 285
cagacaaggt cccaaagaca g                                               21

<210> SEQ ID NO 286
<211> LENGTH: 21
<212> TYPE: DNA
<213> ORGANISM: Artificial sequence
<220> FEATURE:

<223> OTHER INFORMATION: Cyclophilin A, reverse primer

<400> SEQUENCE: 286
ttgccatcca accactcagt c                              21

HUMAN TASTE CELLS CAPABLE OF CONTINUOUS PROLIFERATION

This application is the National Phase Under 35 USC §371 of PCT International Application No. PCT/EP2013/058662 filed on Apr. 25, 2013, which claims priority under 35 USC §119 of Application No. 12165564.1 filed in the European Patent Office on Apr. 25, 2012. The entire contents of each of which are incorporated by reference.

The present invention relates to proliferating human taste cells, wherein the cells are the cells deposited under the DSMZ deposit accession number DSM ACC3169 or taste cells derived thereof. The present invention further relates to the proliferating human taste cells of the invention for use in research. Further, the present invention relates to in vitro methods for analysing the signalling response of taste cells to a molecule involved in taste signalling, in vitro methods of identifying agents capable of eliciting a taste response in taste cells as well as in vitro methods of identifying modulators of taste signalling.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The sensory modality taste guides humans to identify and consume nutrients while at the same time avoiding toxins and indigestible materials. Taste is said to comprise the basic taste qualities sweet, umami, sour, salty, and bitter as well as additional qualities such as fatty, metallic, and others.

The taste receptors found for example in type II taste cells for the detection of bitter, sweet and umami taste molecules are G protein-coupled receptors (GPCRs), whereas the taste modalities salty and sour are said to be mediated by ion channels, which can reside for example in type I and type III cells but not in type II cells. Sweet, umami, and bitter compounds each activate different taste GPCRs which are expressed in distinct populations of taste receptor cells that appear to be non-overlapping.

For instance, receptor cells that express members of the group of 20 to 35 mammalian GPCRs of the T2R family sense bitter compounds. Bitter taste receptors show heterogeneous molecular receptive ranges. Some are narrowly programmed to detecting 2 to 4 bitter-tasting compounds, whereas others are promiscuously activated by numerous ligands. In situ hybridizations revealed that subsets of several T2Rs are co-expressed in a single population of rodent taste cells. In situ hybridizations using human taste buds revealed that subsets of 4 to 11 T2Rs are expressed in different bitter-responsive taste cells in partially overlapping fashion (Chaudhari, N., & Roper, S. D. The cell biology of taste. *The Journal of cell biology*, 2010, 190(3): 285-296; Kinnamon, S. C. Taste receptor signalling—from tongues to lungs. Acta physiologica, 2012, 204(2):158-68).

Sugars, synthetic sweeteners, and sweet-tasting proteins such as monellin and brazzein stimulate receptor cells expressing the T1R2/T1R3 heterodimer. However, current evidence suggests that additional receptors for sweet taste molecules may exist. Umami taste signalling is mediated by heterodimeric T1R1/T1R3 GPCRs. However, additional taste receptors may also contribute to umami detection (Chaudhari, N., & Roper, S. D. The cell biology of taste. The Journal of cell biology, 2010, 190(3): 285-296; Kinnamon, S. C. Taste receptor signalling—from tongues to lungs. Acta physiologica, 2012, 204(2):158-68; Damak et al., Detection of sweet and umami taste in the absence of taste receptor T1r3. *Science*, 2003, 301: 850-853; Maruyama et al., Umami responses in mouse taste cells indicate more than one receptor. *J Neurosci*, 2006, 26: 2227-2234; Yasumatsu et al., Umami taste in mice uses multiple receptors and transduction pathways. *J Physiol*, 2012, 590: 1155-1170).

The T1Rs belong to the dimeric Class III GPCRs, with large N-terminal extracellular domains, which forms a Venus Flytrap structure. In contrast, T2Rs resemble Class I GPCRs with binding sites in the transmembrane helices, which is consistent with the non-polar properties of many bitter ligands (Chaudhari, N., & Roper, S. D., The cell biology of taste. *The Journal of cell biology*, 2010, 190(3): 285-296; Kinnamon, S. C., Taste receptor signalling—from tongues to lungs. *Acta physiologica*, 2012, 204(2):158-68).

Studies using mammalian model organisms revealed that taste GPCRs activate heterotrimeric GTP-binding proteins after stimulation with taste molecules. For instance, bitter receptors can activate the taste-selective $G\alpha$ subunit, $\alpha$-gustducin, and the closely related $\alpha$-transducin. T1R3-containing taste receptors may also activate $G\alpha14$ ($G\alpha q$). Given their similarity to the visual system, gustducin and transducin are expected to activate a phosphodiesterase (PDE) and decrease intracellular cAMP levels. Indeed, bitter stimuli were found to decrease intracellular cAMP levels in rodents. Cyclic AMP is also decreased in rodent taste tissue in response to umami stimuli. However, many studies have shown that sugars increase cAMP levels in taste tissue and the increase is not simply a secondary consequence of $Ca^{2+}$ release from intracellular stores. Studies using $\alpha$-gustducin knock-out mice further revealed that $\alpha$-gustducin is not required for bitter taste signalling in all taste papillae and that potentially several alternative $G\alpha$ subunits can replace $\alpha$-gustducin (Chaudhari, N., & Roper, S. D. The cell biology of taste. *The Journal of cell biology*, 2010, 190(3): 285-296; Kinnamon, S. C., Taste receptor signalling—from tongues to lungs. *Acta physiologica*, 2012, 204(2):158-68).

In addition to the fact that GPCRs may have a preference for $G\alpha$ subunits, the main binding partners of the $G\alpha$ subunits appear to be $G\gamma13$ and $G\beta1$ or $G\beta3$. Ligands binding to GPCR release the $G\alpha$ subunit ($G\alpha q$, $G\alpha i$, $G\alpha s$) together with the $G\beta\gamma$ subunits, which subsequently interact with phospholipase $PLC\beta2$, an isoform that is activated by $G\beta\gamma$ rather than the more common $G\alpha q$ family subunits. Mice carrying a $PLC\beta2$ knock-out showed a severely diminished but not entirely eliminated taste sensitivity. $PLC\beta2$ activation leads to an increase of $IP_3$, which opens $IP_3R3$ ion channels located on the endoplasmic reticulum releasing $Ca^{2+}$ into the cytosol of receptor cells. Elevated intracellular $Ca^{2+}$ can in turn stimulate the taste-selective cation channel TRPM5, which can produce a depolarizing generator potential in receptor cells and lead to the opening of gap junction hemichannels, which secrete ATP. Taken together, using this $G\alpha q/G\beta\gamma/PLC\beta2$ signalling pathway, taste molecules can evoke an increased cytoplasmic $Ca^{2+}$, strong depolarization and release of the taste bud transmitters, for instance ATP. Evidence for this signalling pathway comes from immunocytochemical and molecular studies in rodents showing that these components are co-expressed in both bitter and sweet/umami responsive Type II taste cells and stimulation of isolated rodent Type II taste cells with bitter, sweet or umami taste stimuli elicits increases in intracellular $Ca^{2+}$ that do not require extracellular $Ca^{2+}$, are blocked by the PLC inhibitor U73122, and are sensitive to thapsigargin, which inhibits the $Ca^{2+}$ ATPase that refills intracellular $Ca^{2+}$ stores (Chaudhari, N., & Roper, S. D. The cell biology of taste. *The Journal of* cell biology, 2010 190(3): 285-296; Kinnamon, S. C. Taste receptor signalling—from tongues to lungs. *Acta physiologica*, 2012, 204(2):158-68).

Activation of taste receptors and the subsequent signalling events in taste cells lead to the release of taste bud transmitters, such as for instance ATP. ATP that is released from taste cells then activates ionotropic ATP receptors (P2X2/P2X3) on taste nerves as well as metabotropic (P2Y) receptors on taste cells.

The ATP signal can be terminated by ectonucleotidases within taste buds. NTPDase2 was shown to be expressed by Type I taste cells and degrades ATP to form ADP which can activate purinergic P2Y receptors or is further degraded to adenosine by other nucleotidases and phosphatases. It has been shown that adenosine can enhance sweet taste in mice through A2B G-protein coupled adenosine receptors. A2B receptor gene is expressed in a subset of taste cells, which also express sweet taste receptors and Gα14 (Chaudhari, N., & Roper, S. D. The cell biology of taste. *The Journal of cell biology*, 2010 190(3): 285-296; Kinnamon, S. C. Taste receptor signalling—from tongues to lungs. *Acta physiologica*, 2012, 204(2):158-68).

In the rodent model system, four targets were proposed for fatty taste reception: a delayed-rectifying potassium (DRK) channel sensitive to PUFAs, the FA transporter CD36/FAT as well as two G protein-coupled receptors, GPR40 and GPR120. Because FAs act as open-channel blockers on the DRK KCNA5, a modulatory role was proposed for KCNA5 (Galindo, M. et al. G Protein-Coupled Receptors in Human Fat Taste Perception, *Chem Senses*. 2012 February; 37(2): 123-39, Keller, K L et al., Common Variants in the CD36 Gene Are Associated With Oral Fat Perception, Fat Preferences, and Obesity in African Americans. *Obesity*, 2012, Jan. 12; Mattes, R. D. 2011. Accumulating evidence supports a taste component for free fatty acids in humans. *Physiology & behavior*, 104(4): 624-631).

CD36 is expressed in lingual epithelium of rodents and co-localizes α-gustducin and CD36 knockout mice revealed perceptual deficits for linoleic acid compared with wild type mice, whereas their sensitivity to stimuli of other taste qualities remained unchanged.

GPR120 was detected in gustatory tissue of mice and was found to be predominantly expressed in type II taste receptor cells of foliate and vallate papillae, whereas GPR40 is mainly found in type I taste cells of mice but not found in rat gustatory papillae. Knockout mice for both GPR40 and GPR120 exhibited diminished sensitivity toward LCFAs.

Humans perceive fatty acids by olfactory, somatosensory as well as gustatory cues in the millimolar range. To date, human CD36 was found to localize to human foliate and circumvallate papillae and GPR120 is detected in gustatory and nongustatory lingual epithelia. It was further shown in calcium imaging assays using recombinant HEK293 cells that the human GPR40 and GPR120 response to fatty acids is consistent with human sensory data (Galindo, M. et al. G Protein-Coupled Receptors in Human Fat Taste Perception, *Chem Senses*. 2012 February; 37(2):123-39, Keller, K L et al., Common Variants in the CD36 Gene Are Associated With Oral Fat Perception, Fat Preferences, and Obesity in African Americans. *Obesity*, 2012, Jan. 12; Mattes, R. D. 2011. Accumulating evidence supports a taste component for free fatty acids in humans. *Physiology & behavior*, 104(4): 624-631).

Taste is linked to mood, appetite, obesity and satiety, however, the underlying mechanism are not yet understood. Serotonin-enhancing drugs were shown to influence taste thresholds (Heath, T P et al., Human taste thresholds are modulated by serotonin and noradrenaline. *J Neurosci*, 2006, 26(49): 12664-12671) and appetite regulating neuropeptide hormones, for instance leptin, glucagon-like peptide and oxytocin, turn out to modulate gustatory processes of taste cells. Leptin acts directly on taste receptor cells and reduces sweet responses (Kawai, K., Leptin as a modulator of sweet taste sensitivities in mice. *Proceedings of the National Academy of Sciences*, 2000, 97(20): 11044-11049; Nakamura, Y. et al., Diurnal variation of human sweet taste recognition thresholds is correlated with plasma leptin levels, 2008, *Diabetes*, 57(10): 2661-2665). The anorectic peptide oxytocin leads to calcium signalling in a population of rodent taste bud cells expressing the oxytocin-receptor gene OXTR (Sinclair, M S et al., Oxytocin signalling in mouse taste buds. 2010 *PLoS One*, 5(8): e11980). Interestingly, oxytocin knock-out mice showed an overconsumption of salty and sweet solutions in preference tests (Billings, L B et al. Oxytocin null mice ingest enhanced amounts of sweet solutions during light and dark cycles and during repeated shaker stress. *Behavioural brain research*, 2006, 171(1): 134-141; Sclafani, A. et al., Oxytocin knockout mice demonstrate enhanced intake of sweet and nonsweet carbohydrate solutions. *American Journal of Physiology. Regulatory, integrative and comparative physiology*, 2007, 292(5): R1828-1833; Vollmer, R R et al. Sodium ingestion in oxytocin knockout mice. *Experimental neurology*, 2006, 202(2): 441-448).

It was also shown that satiety peptides, for instance glucagon-like peptide-1 (Shin, Y K et al. 2008. Modulation of taste sensitivity by GLP-1 signalling. *J Neurochem*, 2008, 106(1): 455-463) and ghrelin Shin, Y K et al., Ghrelin is produced in taste cells and ghrelin receptor null mice show reduced taste responsivity to salty (NaCl) and sour (citric acid) tastants. *PLoS One*, 2010, 5(9): e12729) are synthesized in taste buds and act on taste cells or nerve cells.

Elucidation of human taste reception and signal transduction mechanisms using human taste cells is required to improve the understanding of the complex sensory modality "taste" as well as to develop new technologies for industry applications in the field of taste modulation and satiety. Conventionally, mechanistic insights were derived using mammalian model organisms and recombinant cell-based technologies and applied to human taste despite all potential limitations and deficiencies, due to the lack of continuous human taste cell lines.

In the art, several model cell systems, mostly recombinant host cells, for investigating certain taste receptors were disclosed. For example in U.S. Pat. No. 8,003,384 B2 cells were engineered to express sour receptors for the screening of sour taste molecules. Expression of taste receptors for bitter (e.g. WO 2011/050955 A1, U.S. Pat. No. 8,030,468), sweet (e.g. U.S. Pat. No. 7,763,431, U.S. Pat. No. 8,119,359), salty (e.g. WO 2009/139913 A1) and umami (e.g. U.S. Pat. No. 8,119, 402), respectively, as well as non-specific (U.S. Pat. No. 8,067,539) or chimeric receptors (e.g. sweet-umami: U.S. Pat. No. 7,906,627) in host cells for the identification of novel taste compounds has been widely described. In a more artificial approach lipid membranes comprising sodium ion channels for detecting salty taste molecules (US 2011/0236313 A1) or a so-called spice matrix comprising recombinant host cells expressing ion channels of the TRP-type were disclosed (WO 2008/060576 A2) in order to generate a reactivity profile of taste compounds. Conventional, recombinant screening technologies are commonly based on e.g. non-human for instance murine cells, transformed human cells or cancer cells e.g. Human Embryonic Kidney HEK293 cells or HeLa cells, which have been stably or transiently transfected with for example one or two genes encoding taste receptors and signalling molecules. As a consequence, these cells do not possess the complex, multifactorial endogenous properties conferred by the large number of taste receptors and signalling components naturally occurring in human taste cells from lingual epithelium, which are required to respond to taste molecules the same way as human taste cells do. It is known to a person skilled in the art that these shortcomings can lead to false positives and false negative results in assays based on these cells.

Taste cells derived from mammalian tongue were also investigated and disclosed in e.g. WO 2008/153924 A2 and WO 2006/044594 A2. However, in the former application the cells were isolated but not cultured and in the latter application the mammalian taste cell cultures were derived from tongue tissue and contain a mixture of cells, including taste cells and other cell types, are slowly proliferating and have a limited life span of about three months. Also, model taste cells from enteroendocrine cells were described in WO 2008/014450 A2 expressing mainly sweet receptors. Assays performed with these cells including HUTU-80 Human Duodenum Adenocarcinoma cells and derivatives thereof can suffer from the same shortcomings as described above for recombinant screening cells due to the lack of the complex, multifactorial properties that characterize human taste cells from lingual epithelium.

To date, there is no stably proliferating human cell culture model for lingual taste cells. Moreover, there are no stably proliferating human taste cell lines available in the art that express genes encoding gustatory receptors, ion channels and signalling components or genes encoding hormone receptors including for example the leptin receptor and oxytocin receptor and that are suitable for testing the endogenous response to taste molecules as well as peptide hormones. Accordingly, there is a lack of model taste cells derived from taste bud with long-term stability and functional consistency suitable for testing endogenous response to taste molecules and analysing the respective signalling pathways. All cell-based in vitro research approaches so far had to rely on primary cell cultures of taste cells, which can be maintained for a limited time. Recently, a method for rat taste bud primary cell culture (Ruiz, C. et al., Tissue culture of rat taste buds. In A. I. Spielman, & J. G. Brand (Eds.), *Experimental cell biology of taste and olfaction: current techniques and protocols:* 1995, 79-84: CRC Press; Ruiz, C J et al., Maintenance of rat taste buds in primary culture. *Chem Senses*, 2001, 26(7): 861-873) and for the extended culture of rodent taste cells was reported (Ozdener, H et al. Characterization and long-term maintenance of rat taste cells in culture. *Chem Senses*, 2006, 31(3): 279-290). This cultivation technique was further extended to primary cultures of cells from human fungiform papillae (Ozdener, M H et al., Characterization of Human Fungiform Papillae Cells in Culture. *Chemical senses*, 2011, 36(7): 601-612) but the cells thus obtained represent a mixed culture of various taste cells and are not capable of proliferating stably for an extended amount of time and passage number.

Although primary cell cultures and cell strains can be used to study characteristic properties and gene expression patterns of functionally distinct cell types, they have a finite life span and it is believed that proliferative capability and maintenance of cell type-specific properties of differentiated cells are mutually exclusive. Spontaneous transformation or exogenous immortalization of primary cells have been previously established, however, the resulting cells often de-differentiate and lose their cell type-specific properties (Lodish, H., Berk, A., Kaiser, C. A., Krieger, M., Scott, M. P., Bretscher, A., Ploegh, H., & Matsudaira, P. 2006. *Molecular Cell Biology* (Sixth ed.). New York: W.H. Freeman and Company).

Murine primary cells can be readily immortalized through the expression of oncogenes (Hurwitz, D. R., & Chinnadurai, G., Immortalization of rat embryo fibroblasts by an adenovirus 2 mutant expressing a single functional E1a protein. *Journal of virology*, 1985, 54(2): 358-363; Rassoulzadegan, M. et al., Expression of the large T protein of polyoma virus promotes the establishment in culture of "normal" rodent fibroblast cell lines. *Proceedings of the National Academy of Sciences of the United States of America*, 1983, 80(14): 4354-4358), although they often de-differentiate and lose part of their cell type-specific characteristics in the process. Whereas continuously growing murine cell lines are rather easy to obtain through the expression of a single oncogene (Jat, P. S., & Sharp, P. A., Cell lines established by a temperature-sensitive simian virus 40 large-T-antigen gene are growth restricted at the nonpermissive temperature. *Molecular and Cellular Biology*, 1989, 9(4): 1672-1681), this immortalization usually fails in human cells (Shay, J W et al., The frequency of immortalization of human fibroblasts and mammary epithelial cells transfected with SV40 large T-antigen. *Experimental cell research*, 1993, 209(1): 45-52; Wright, W E, Reversible cellular senescence: implications for immortalization of normal human diploid fibroblasts. *Molecular and Cellular Biology*, 1989, 9(7): 3088-3092), because these factors do not cause immortalization but rather a life span extension of human cells. After a certain number of cell divisions a crisis occurs, which results in the rapid senescence and death of the cells in culture (Shay, J W et al., The frequency of immortalization of human fibroblasts and mammary epithelial cells transfected with SV40 large T-antigen. *Experimental cell research*, 1993, 209(1): 45-52) most likely due to critical attrition of telomere length, which can be overcome by expressing human telomerase (hTERT) (Henderson, S. et al., In situ analysis of changes in telomere size during replicative aging and cell transformation. *The Journal of cell biology*, 1996, 134(1): 1-12). However, the ectopic expression of hTERT alone does not necessarily induce changes associated with transformation (Jiang, X R et al., Telomerase expression in human somatic cells does not induce changes associated with a transformed phenotype. *Nature genetics*, 1999, 21(1): 111-114; Morales, C P, Absence of cancer-associated changes in human fibroblasts immortalized with telomerase. *Nature genetics*, 1999, 21(1): 115-118).

Thus, despite the fact that a lot of effort has been invested into methods to establish proliferating taste cell cultures, no method exists so far that enables the long-term cultivation of proliferating taste cells and continuous cell lines that resemble the mature phenotype of human taste cells involved in taste perception. For researchers to understand the complex sensory modality taste, it would be favourable to employ such cells that more closely resemble the mature taste cells responsible for taste perception in vivo. Accordingly, there is still a need to provide such cell cultures, for example for drug discovery.

This need is addressed by the provision of the embodiments characterised in the claims.

Accordingly, the present invention relates to human taste cells, wherein the cells are the cells deposited under the DSMZ deposit accession number DSM ACC3169 on Apr. 18, 2012 by BRAIN AG, Zwingenberg, in accordance with the requirements of the Budapest Treaty with the Leibniz-Institute Deutsche Sammlung von Mikroorangismen und Zellkulturen (DSMZ—German Collection of Microorganisms and Cell Cultures) located a Inhoffenstraβe 7B, 38124 Braunschweig, Germany and which is approved as an International Depository, or taste cells derived thereof. The deposited cells bear the internal designation BR-HTC8 of the applicant and are described for identification purposes in detail in this specification. All restrictions upon availability to the public of strain DSM ACC3169 will be irrevocably removed upon issuance of a patent.

"Taste cells", in accordance with the present invention, relate to sensory cells capable of sensing taste molecules. Taste cells reside in taste buds, which are comprised of approx. 50 to 100 polarized neuroepithelial cells and are embedded in epithelia of the oral cavity. The majority of the approximately 5,000 human taste buds are localized to the lingual epithelium but some also reside on the palate and on the epiglottis.

Electron microscopy, immunocytochemistry as well morphometric analysis revealed that discrete cell type populations reside in the mammalian taste bud. Historically, taste bud cells were termed Types I, II, and III, and presumably non-differentiated Basal/Type IV cells (Chaudhari, N., & Roper, S. D. The cell biology of taste. *The Journal of cell biology*, 2010, 190(3): 285-296; Kinnamon, S. C. Taste receptor signalling—from tongues to lungs. *Acta physiologica*, 2012, 204(2):158-68).

Type I cells are the most abundant cells in taste buds and resemble glial cells of the central nervous system and are assumed to be involved in terminating synaptic transmission and restricting the spread of transmitters. Markers expressed by type I cells include for example GLAST, NTPDase2 and ROMK. Recent data suggest that Type I cells may exhibit ionic currents implicated in salt taste transduction.

Type II cells contain receptors in the plasma membrane that bind sweet, bitter, or umami taste molecules. These taste receptors are G protein-coupled receptors, which trigger downstream signalling events. Type II cells also express voltage-gated Na and K channels known for producing action potentials, and hemichannel subunits for ATP secretion triggered by taste molecule interactions with its cognate receptor. Type II cells do not appear to be directly stimulated by sour or salty stimuli and any given Type II cell expresses taste GPCRs specific for only one taste quality, such as sweet or bitter, or umami (Chaudhari, N., & Roper, S. D., The cell biology of taste. *The Journal of cell biology*, 2010190(3): 285-296; Kinnamon, S. C., Taste receptor signalling—from tongues to lungs. *Acta physiologica*, 2012, 204(2):158-68).

In contrast to all other taste bud cells, Type III cells contain proteins, which indicate that they are associated with synapses and that they form synaptic nerve cell junctions. They express the cell surface adhesion molecule NCAM, enzymes for the synthesis of two neurotransmitters, and voltage-gated calcium channels typically associated with neurotransmitter release. Type III cells revealed depolarization-dependent $Ca^{2+}$ transients, are excitable and express voltage-gated Na and K channels to support action potentials (Chaudhari, N., & Roper, S. D. The cell biology of taste. *The Journal of cell biology*, 2010190(3): 285-296; Kinnamon, S. C. Taste receptor signalling—from tongues to lungs. *Acta physiologica*, 2012, 204(2):158-68).

Basal cells/Type IV cells are spherical cells without extensions to the taste pore and potentially constitute undifferentiated or immature taste cells. Conclusive markers for this cell population have not been identified and hence the functional significance of basal cells has still to be defined.

This historically grown nomenclature of type I, II, II and IV cells is based on studies with taste buds and taste cells isolated form mammalian model organisms, for instance rat and mouse, and describes co-expression of a rather limited number of gustatory marker genes in these cell types or the lack thereof. However, comprehensive studies using statistically relevant numbers of taste cells representing all cell types residing in particular in human taste buds in fungiform, foliate and circumvallate papillae with regard to expression patterns of a quickly expanding number of genes relevant for taste reception and signalling in combination with functional characterization of these cells will be necessary to describe the diversity of human taste cells. Stably proliferating human taste cell cultures will be one first step towards this goal.

The taste cells of the present invention are human taste cells and are most similar to Type II cells (see below) and have been deposited with the Leibniz Institute DSMZ, the German Collection of Microorganisms and Cell Cultures under DSMZ deposit accession number DSM ACC3169 on Apr. 18, 2012 by BRAIN AG, Zwingenberg. These cells are also referred to herein as BR-HTC8 cells or as "parental cells".

The human taste cells of the present invention are capable of proliferation, i.e. are proliferating cells, also referred to herein as "self-renewing cells". Accordingly, the cells of the present invention are capable of going through numerous cycles of cell division and are also referred to herein as "stably proliferating cells". Preferably, the proliferating taste cells of the present invention maintain their ability to divide for at least 10 generations, such as for example at least 11 generations, such as at least 12 generations, such as at least 13 generation, such as at least 14 generations, such as at least 15 generations, such as at least 16 generations, such as at least 17 generation, such as at least 18 generations, such as at least 19 generations, such as at least 20 generations, such as at least 21 generation, such as at least 22 generations, such as at least 23 generations, such as at least 24 generations, and more preferably at least 25 generations. More preferably, the proliferating taste cells of the present invention maintain their ability to divide for at least 26 generations, such as at least 27 generations, such as at least 28 generation, such as at least 29 generations and even more preferably at least 30 generations, such as at least 35 generations, such as at least 40 generations, such as at least at least 45 generations, such as at least 50 generations, such as at least 55 generations, such as at least 60 generations, such as at least 65 generations, such as at least 70 generations, such as at least 75 generations, such as at least 100 generations and even more preferably at least 150 generations. Most preferably, the proliferating taste cells of the present invention maintain their ability to divide for an unlimited amount of time.

The skilled person is well aware of methods of determining the amount of generations, i.e. cell divisions, that a cell has been proliferating for. For example, cell divisions can be measured by continuous cultivation of the proliferating cells. The adherent cells are, for example, cultivated in a tissue culture dish of defined size until they have formed a nearly confluent monolayer. Cells are then harvested and diluted, such as for example at least 1:2, preferably 1:3, more preferably 1:4, and most preferably 1:5. The cells are then further cultivated in a new tissue culture dish of equal size until the cells have formed again a near confluent monolayer. This process is also referred to herein as passaging. Based on the dilution ratio employed, the number of cell divisions that took place between two passages can be determined. For example, if the cells were diluted 1:2 (i.e. half of the cells are plated into one new culture dish), then one cell division needs to take place in order to double the number of cells, thereby resulting in a confluent layer. If the cells were diluted 1:3, then only one third of the cells will be plated into a new culture dish. Accordingly, it takes 1.5 generations for the cells to grow confluent. If the cells were diluted 1:4, then one quarter of the cell is plated to a new culture dish, therefore requiring two generations before the cells have grown confluent again.

The term "at least", as used herein, refers to the specifically recited amount or number but also to more than the specifically recited amount or number. For example, the term "at least 10 generations" encompasses also at least 11, at least 12, at least 13, at least 14, at least 15, at least 20, at least 30, at least 40 generations, such as at least 50, at least 60, at least 70, at least 100 generations and so on. Furthermore, this term also encompasses exactly 10, exactly 11, exactly 12, exactly 13, exactly 14, exactly 15, exactly 20, exactly 30, exactly 40, exactly 50, exactly 60, exactly 70, exactly 100 generations and so on.

Preferably, the requirement that the taste cells of the present invention maintain their ability to divide for several generations as defined above includes that the rate of cell division of these cells does not or does not substantially decrease. Accordingly, the rate of proliferation after e.g. 10 or more generations remains substantially the same or is even increased as compared to the rate of proliferation of the parental cells if grown under essentially identical conditions. The rate of proliferation is considered to have not substantially decreased as compared to the rate of proliferation of the parental cells if it is at least 70% of the rate of proliferation of the parental cells, such as e.g. at least 80% of the rate of proliferation of the parental cells, more preferably at least 90% of the rate of proliferation of the parental cells, such as e.g. at least 95% of the rate of proliferation of the parental cells. More preferably, the rate of proliferation is identical to the rate of proliferation of the parental cells, and optionally the rate of proliferation is higher than the rate of proliferation of the parental cells, such as e.g. 120% of the rate of proliferation of the parental cells, more preferably 150% of the rate of proliferation of the parental cells. The skilled person is well aware of how to determine the rate of proliferation. Non-limiting example include determination of the frequency of splitting (i.e. passaging) of the cells required or of cell numbers after a certain period of growth, such as e.g. 24 hours after splitting etc. as described for example in standard laboratory handbooks such as e.g. Lindl, T. Zell-und Gewebekultur, Spektrum, Akad. Verlag, Heidelberg 2000 or Celis, J. E., Cell biology: a laboratory handbook. Volume 3, Academic Press, San Diego 1994; J. Masters, ed., "Animal cell culture", Oxford University Press, 2000).

Further in accordance with the present invention, the cells of the present invention maintain or essentially maintain their phenotype during self-renewal, even after prolonged periods of time. The term "phenotype" of the taste cells of the invention refers to their specific marker expression profile as well as their morphological appearance. Accordingly, the phenotype of the cells after e.g. 10 or more generations remains the same or essentially the same as compared to the phenotype of the parental cells (i.e. the initial phenotype).

The cells of the present invention are characterised by a specific marker expression profile that includes the presence of at least two markers selected from the group consisting of Oct-4, Ptc1, PLCD4, gustducin, PANX1, keratin 19, keratin 5, keratin 8, GLAST, NTPD, OXTR, LEPR, HTR2B, IP3R3, ADORA2B, PDE1A, CD36, TAS2R4, TAS2R5, TAS2R10, TAS2R14, TAS2R16, TAS2R38, TAS2R39, TAS2R43, TAS2R44, TAS2R45, TAS2R47, TAS2R48, TAS2R49, GNAQ, GNA14, GNA14, GNA13, GNB3, GNB1, P2RY12, P2RX7, SCN3A, SCN9A, ENAC beta, ENAC delta, TRPV1, and TRPA1 and/or the lack of expression of at least 1 marker selected from the group consisting of NCAM, PLCb2, PKD2L1, mGLU1, mGLU4, T1R1, T1R2, TRPM8, TRPM5, P2RX2, P2RX3, GPR120, GPR40, Sox2, and keratin 14.

Database accession numbers for these markers as well as primers allowing for the detection of these markers are presented in table 1 below.

More preferably, the cells are characterised by the expression of at least 5 markers selected from the group consisting of Oct-4, Ptc1, PLCD4, gustducin, PANX1, keratin 19, keratin 5, keratin 8, GLAST, NTPD, OXTR, LEPR, HTR2B, IP3R3, ADORA2B, PDE1A, CD36, TAS2R4, TAS2R5, TAS2R10, TAS2R14, TAS2R16, TAS2R38, TAS2R39, TAS2R43, TAS2R44, TAS2R45, TAS2R47, TAS2R48, TAS2R49, GNAQ, GNA14, GNA14, GNA13, GNB3, GNB1, P2RY12, P2RX7, SCN3A, SCN9A, ENAC beta, ENAC delta, TRPV1, and TRPA1 and/or the lack of expression of at least 2 markers selected from the group consisting of NCAM, PLCb2, PKD2L1, mGLU1, mGLU4, T1R1, T1R2, TRPM8, TRPM5, P2RX2, P2RX3, GPR120, GPR40, Sox2, and keratin 14.

Even more preferably, the cells are characterised by the simultaneous expression of a group of bitter taste receptors consisting of TAS2R4, TAS2R5, TAS2R10, TAS2R14, TAS2R16, TAS2R38, TAS2R39, TAS2R43, TAS2R44, TAS2R45, TAS2R47, TAS2R48, and TAS2R49 and the lack of expression of T1R1 and/or T1R2. The simultaneous expression of these bitter taste receptors indicates that the cells resemble type II taste cells dedicated to bitter taste perception, whereas the genes encoding other taste G protein-coupled receptors including T1R1 for umami taste perception and T1R2 for sweet taste perception are not expressed. An overview over bitter taste receptors expressed or lacking expression in the cells of the present invention is provided in table 2 below.

Even more preferably, the cells are characterised by the additional expression of the oxytocin receptor OXTR and the leptin receptor LEPR.

Even more preferably, the cells are characterised by the additional expression of the fatty taste perception gene CD36.

Even more preferably, the cells are characterised by the additional expression of the pluripotency gene Oct-4.

Even more preferably, the cells are characterised by the additional expression of genes encoding ion channels implicated with salty taste perception including TRPV1, TRPML3, ENAC beta subunit (SCNN1B), and ENAC delta subunit (SCNN1D) and the lack of expression of genes involved in sour taste perception including PKD2L1.

Even more preferably, the cells are characterised by the additional expression of genes encoding signal transduction factors including PLCD4, gustducin, PANX1, GLAST, NTPD, HTR2B, IP3R3, ADORA2B, PDE1A, GNAQ, GNA14, GNA14, GNA13, GNB3, GNB1, P2RY12, P2RX7, SCN3A, and/or SCN9A.

Most preferably, the cells are characterised by the expression profile as shown in Table 1 below.

The skilled person is aware of how to determine these characteristics. For example, parental cells may be directly compared to cells after cell culture for several generations and their morphology and/or marker expression profile may be compared via methods well known in the art. Non-limiting examples of assessing the morphology of a cell include e.g. microscopic analysis, such as with an electron microscope. Moreover, the expression of specific markers can be determined on the amino acid level as well as on the nucleic acid level by methods well known in the art.

Methods for determining the expression of a specific marker on the nucleic acid level include, but are not limited to, northern blotting, PCR, RT-PCR or real time RT-PCR. Methods for the determination of the expression of a specific marker on the amino acid level include but are not limited to western blotting or polyacrylamide gel electrophoresis in conjunction with protein staining techniques such as Coomassie Brilliant blue or silver-staining. Also of use in protein quantification is the Agilent Bioanalyzer technique. These methods are well known in the art.

In accordance with the present invention, the proliferating taste cells of the present invention are considered to essentially maintain their phenotype if the degree of similarity between the parental cells of the invention and the cells after proliferation, is at least 70%, more preferably at least 80%, such as e.g. at least 90% and more preferably at least 95%. Even more preferably, the degree of similarity is at least 99%. The degree of similarity can be determined based on any (or all) of the above described characteristics. For example, a complete expression profile of the proliferating taste cells after passaging may be compared to the expression profile of the parental taste cells and the degree of similarity may be determined. More preferably, the expression profile with regard to the above described markers may be compared and, most preferably, the expression or lack of expression of all of the above recited markers is identical between the cells after proliferation and the parental cells.

In accordance with the present invention, it is preferred that the human taste cells of the invention maintain or essentially maintain their phenotype in culture for at least 10 generations.

The term "taste cells derived thereof", as used herein, encompasses both (human) taste cells derived from the parental cells (i.e. the cells deposited under the DSMZ deposit accession number DSM ACC3169) by culture expansion of these cells or by genetically engineering these cells. These cells maintain or essentially maintain their capacity of proliferation.

The term "expansion", in accordance with the present invention, refers to a multiplication of cells, thus resulting in an increase in the total number of cells. Thus, cells can be expanded to at least twice their original number, more preferably to at least 10 times their original number, such as for example at least 100 times, such as at least 1,000 times their original number and most preferably to at least 10,000 times, such as at least 100,000 times their original number. Expansion of the cells may be achieved by known methods, e.g. by culturing the cells under appropriate conditions to high density or confluence and subsequent splitting (or passaging) of the cells, wherein the cells are re-plated at a diluted concentration into an increased number of culture dishes or onto solid supports. With increasing passage number, the amount of cells obtained therefore increases due to cell division. The skilled person is aware of means and methods for splitting cells and can determine the appropriate time point and dilution for splitting cells. Preferably, cells are split between 1:2 and 1:5 every two to four days.

General cell culture conditions as well as suitable cell culture media are well known in the art (e.g. Cooper G M (2000). "Tools of Cell Biology", ISBN 0-87893-106-6; K. Turksen, ed., Humana Press, 2004, J. Masters, ed., Oxford University Press, 2000, "Animal cell culture", ISBN-10 0-19-963796-2). Suitable culture conditions and media are, for example, shown in more detail in the Examples of the invention. It is preferred in any of the cell culture conditions described herein that the medium is exchanged (i.e. refreshed) at appropriate intervals, such as e.g. every four days, more preferably every three days, such as e.g. every two days and most preferably the medium is exchanged for fresh cell culture medium every 24 hours.

Suitable cell culture media include, without being limiting, Dulbecco's MEM (e.g. FG 1445, Biochrom), Basal Iscove Medium (e.g. F0465, Biochrom), MCDB 153 Basal Medium (e.g. F8105, Biochrom AG), William's Medium E (e.g. F 1115, Biochrom) containing additives including, without being limiting, FCS Gold (e.g. A15-151, PAA Laboratories GmbH), L-glutamine (e.g. M11-004, PAA Laboratories GmbH), antibiotic/antimycotic (e.g. A5955, Sigma-Aldrich GmbH), gentamycin (e.g. A2712, Biochrom), insulin (e.g. 19278, Sigma-Aldrich GmbH) and/or additional additives known in the art.

Preferably, the cells are cultured in HTC medium. 500 ml of HTC medium consists of 400 ml Basal Iscove Medium (e.g. F0465, Biochrom), 100 ml MCDB 153 Basal Medium (e.g. F8105, Biochrom AG) containing 10% FCS Gold (e.g. A15-151, PAA Laboratories GmbH), 4 mM L-glutamine (e.g. M11-004, PAA Laboratories GmbH), 1% antibiotic/antimycotic (e.g. A5955, Sigma-Aldrich GmbH), 2.5 µg/mL gentamycin (e.g. A2712, Biochrom) and 10 µg/mL insulin (e.g. 19278, Sigma-Aldrich GmbH).

Preferably, the cells are cultured at 37° C. until the cells have formed a confluent monolayer covering the surface of the culture dish. Typically, this takes between 2 to 4 days. The cells are then detached using protease treatment, preferably TrypLE (e.g. Gibco, 12563) and are then re-plated at a diluted density of between 1:2 to 1:5 with HTC medium and cultured again until a confluent monolayer covering the surface of the culture dish has grown, and so on.

The term "genetically engineering", as used herein, refers to the process of modifying the genetic information of the cell, for example by bringing into a cell nucleic acid sequences that are not present in said cell prior to the step of genetic engineering (i.e. exogenous nucleic acid molecules), by bringing into a cell nucleic acid sequences that are present in said cell prior to the step of genetic engineering (i.e. endogenous nucleic acid molecules), thereby for example increasing the expression of the expression product encoded by said nucleic acid molecule, or by removing nucleic acid sequences that are present in the parental cell. The term "genetically engineering" is used interchangeably herein with the terms "genetic engineering" and "genetical engineering". In accordance with the present invention, the genetically engineered cells remain taste cells, i.e. the modification does not result in the complete loss of taste signalling pathways. Nonetheless, the genetical engineering is preferably carried out to modify one or more taste signalling pathways in these cells or, alternatively, to introduce immortalization and anti-senescence genes as described in more detail herein below. The above defined degree of similarity with the parental cell line applies mutatis mutandis also to the genetically engineered cells of the invention. In other words, even after genetical engineering, the degree of similarity between the phenotype of the parental cells and of the genetically modified cells is as defined herein above.

Non-limiting examples of exogenous and/or endogenous nucleic acid molecules include receptors, such as e.g. taste receptors, ion channels or downstream signalling molecules involved in taste signalling, genes encoding variants of these receptors, ion channels or downstream signalling molecules, sequences for immortalizing the cells, growth- and proliferation-promoting genes, and pluripotency genes that are either not present in the parental cell, e.g. immortalization genes of viral origin, or are not expressed in the parental cell line, such as e.g. receptors for the taste modalities sweet or umami, which are not expressed in the BR-HTC8 cells of the present invention. Nucleic acid molecules suitable for the immortalization of eukaryotic cells are well known in the art and are further described herein below. Additional examples of exogenous nucleic acid molecule include, without being limiting, molecules that inhibit the expression of a particular expression product, such as receptors, ion channels or signalling molecules. Such inhibitory molecules include for example antisense nucleic acid molecules, small interfering RNAs (siRNAs), short hairpin RNAs (shRNAs) and microRNAs (miRNAs).

The term "antisense nucleic acid molecule", as used herein, is known in the art and refers to a nucleic acid which is complementary to a target nucleic acid, i.e. a nucleic acid encoding the target protein. An antisense molecule in accordance with the invention is capable of interacting with the target nucleic acid, more specifically it is capable of hybridising with the target nucleic acid. Due to the formation of the hybrid, transcription of the target gene(s) and/or translation of the target mRNA is reduced or blocked. Standard methods relating to antisense technology have been described (see e.g., Melani et al., Cancer Res. (1991) 51:2897-2901).

As used herein, the term "small interfering RNA (siRNA)", also known as short interfering RNA or silencing RNA, refers to a class of 18 to 30, preferably 19 to 25, most preferred 21 to 23 or even more preferably 21 nucleotide-long double-stranded RNA molecules that play a variety of roles in biology. Most notably, siRNA is involved in the RNA interference (RNAi) pathway where the siRNA interferes with the expression of a specific gene. In addition to their role in the RNAi pathway, siRNAs also act in RNAi-related pathways, e.g. as an antiviral mechanism or in shaping the chromatin structure of a genome.

siRNAs naturally found in nature have a well defined structure: a short double-strand of RNA (dsRNA) with 2-nt 3' overhangs on either end. Each strand has a 5' phosphate group and a 3' hydroxyl (—OH) group. This structure is the result of processing by dicer, an enzyme that converts either long dsRNAs or small hairpin RNAs into siRNAs. siRNAs can also be exogenously (artificially) introduced into cells to bring about the specific knockdown of a gene of interest. Essentially any gene of which the sequence is known can thus be targeted based on sequence complementarity with an appropriately tailored siRNA. The double-stranded RNA molecule or a metabolic processing product thereof is capable of mediating target-specific nucleic acid modifications, particularly RNA interference and/or DNA methylation. Exogenously introduced siRNAs may be devoid of overhangs at their 3' and 5' ends, however, it is preferred that at least one RNA strand has a 5'- and/or 3'-overhang. Preferably, one end of the double-strand has a 3'-overhang from 1-5 nucleotides, more preferably from 1-3 nucleotides and most preferably 2 nucleotides. The other end may be blunt-ended or has up to 6 nucleotides 3'-overhang. In general, any RNA molecule suitable to act as siRNA is envisioned in the present invention. The most efficient silencing was so far obtained with siRNA duplexes composed of 21-nt sense and 21-nt antisense strands, paired in a manner to have 2-nt 3' overhangs on either end. The sequence of the 2-nt 3' overhang makes a small contribution to the specificity of target recognition restricted to the unpaired nucleotide adjacent to the first base pair. 2'-deoxynucleotides in the 3' overhangs are as efficient as ribonucleotides, but are often cheaper to synthesize and probably more nuclease resistant.

The term "short hairpin RNA (shRNA)", as used herein, is a sequence of RNA that makes a tight hairpin turn that can be used to typically silence gene expression via RNA interference. shRNA can for example use a vector introduced into cells, in which case preferably the U6 promoter is utilized to ensure that the shRNA is always expressed. This vector is usually passed on to daughter cells, allowing the gene silencing to be inherited. The shRNA hairpin structure is cleaved by the cellular machinery into siRNA, which is then bound to the RNA-induced silencing complex (RISC). This complex binds to and cleaves mRNAs which match the siRNA that is bound to it.

Preferably, si/shRNAs to be used in the present invention are chemically synthesized using conventional methods that, for example, appropriately protected ribonucleoside phosphoramidites and a conventional DNA/RNA synthesizer. Suppliers of RNA synthesis reagents are Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). Most conveniently, siRNAs or shRNAs are obtained from commercial RNA oligo synthesis suppliers, which sell RNA-synthesis products of different quality and costs. In general, the RNAs applicable in the present invention are conventionally synthesized and are readily provided in a quality suitable for RNAi.

The term "microRNAs (miRNA)", as used herein, relates to single-stranded RNA molecules which, as endogenous RNA molecules, regulate gene expression. Binding to a complementary mRNA transcript triggers the degradation of said mRNA transcript through a process similar to RNA interference. Accordingly, miRNA may be employed as an inhibitor of the signalling pathways in accordance with the present invention.

Non-limiting examples of nucleic acid sequences to be removed from the parental cell or that are the target of the above described silencing methods include receptors or downstream signalling molecules involved in taste signalling, such as e.g. the receptors and molecules described herein below. Genetically engineered cells modified to lack the expression of specific taste receptors or molecules may be employed e.g. as negative control cells for example in order to confirm that certain taste molecules indeed activate this particular pathway. If a signal is elucidated in the presence of the specific taste receptors or molecules but not in the control cells lacking these specific taste receptors or molecules, then it can be concluded that this pathway is involved in taste signalling mediated by the taste molecule tested.

Introduction of nucleic acid sequences is generally accomplished by transfecting the cell with the nucleic acid molecule, for example by calcium phosphate transfection, DEAE dextran mediated transfection, cationic lipid mediated transfection, electroporation, viral transduction or infection, conjugation, chemotransformation or other methods. Such methods are described in many standard laboratory manuals, such as Sambrook et al.; Molecular Cloning: A Laboratory Manual; Cold Spring Harbor Laboratory Press, 2nd edition 1989 and 3rd edition 2001. Methods for removal of nucleic acid sequences, i.e. the generation of knock-out cell types, are also well known in the art and include Meganucleases, Zinc finger nucleases and Transcription-activator-like (TAL) effector (TALE) nucleases. Such methods are described e.g. in (Klug, A. 2010. The discovery of zinc fingers and their applications in gene regulation and genome manipulation. *Annual review of biochemistry*, 79: 213-231; Miller, J C et al., A TALE nuclease architecture for efficient genome editing. *Nature biotechnology*, 2011, 29(2): 143-148; Silva, G et al., Meganucleases and other tools for targeted genome engineering: perspectives and challenges for gene therapy. *Current gene therapy*, 2011, 11(1): 11-27).

Newly introduced nucleic acid sequence(s) may be incorporated into (a) chromosome(s) of the cell or may be present as extra-chromosomal sequences; both options are explicitly encompassed by the terms "genetically engineering" and "modification of the genome" of the cells of the present invention.

In accordance with the present invention, the term "nucleic acid molecules", also referred to as nucleic acid sequences or polynucleotide herein, includes DNA, such as cDNA or genomic DNA, and RNA. It is understood that the term "RNA" as used herein comprises all forms of RNA including mRNA, ncRNA (non-coding RNA), tRNA and rRNA. The term "non-coding RNA" includes siRNA (small interfering RNA), miRNA (micro RNA), rasiRNA (repeat associated small interfering RNA), snoRNA (small nucleolar RNA), and snRNA (small nuclear RNA). Both, single-strand as well as double-strand nucleic acid sequences are encompassed by this term. Further included are nucleic acid mimicking molecules known in the art such as synthetic or semi-synthetic derivatives of DNA or RNA and mixed polymers, both sense and antisense strands. Such nucleic acid mimicking molecules or nucleic acid derivatives according to the invention include phosphorothioate nucleic acid, phosphoramidate nucleic acid, 2'-O-methoxyethyl ribonucleic acid, morpholino nucleic acid, hexitol nucleic acid (HNA) and locked nucleic acid (LNA) (see Braasch and Corey (2001) Chem Biol. 8, 1). LNA is an RNA derivative in which the ribose ring is constrained by a methylene linkage between the 2'-oxygen and the 4'-carbon. They may contain additional non-natural or derivatised nucleotide bases, as will be readily appreciated by those skilled in the art.

It is preferred in accordance with the present invention that the exogenous and/or endogenous nucleic acid molecules are introduced into the cells in expressible form, i.e. in a form that enables the expression of the respective expression product encoded by said nucleic acid molecule.

Expression of a nucleic acid molecule can for example be ensured by employing regulatory elements. Regulatory elements/sequences are well known to those skilled in the art and include, without being limiting, regulatory sequences ensuring the initiation of transcription, internal ribosomal entry sites (IRES) (Owens, Proc. Natl. Acad. Sci. USA 98 (2001), 1471-1476) and optionally regulatory elements ensuring termination of transcription and stabilisation of the transcript.

Non-limiting examples for regulatory elements ensuring the initiation of transcription comprise a translation initiation codon, enhancers such as e.g. the SV40-enhancer, insulators and/or promoters, such as for example the cytomegalovirus (CMV) promoter, SV40-promoter, RSV (Rous sarcoma virus)-promoter, the lacZ promoter, chicken beta-actin promoter, CAG-promoter (a combination of chicken beta-actin promoter and cytomegalovirus immediate-early enhancer), the gai10 promoter, human elongation factor 1α-promoter, AOX1 promoter, GAL1 promoter CaM-kinase promoter, the lac, trp or tac promoter, the lacUV5 promoter, the Autographa californica multiple nuclear polyhedrosis virus (AcMNPV) polyhedral promoter or a globin intron.

Non-limiting examples for regulatory elements ensuring transcription termination include the V40-poly-A site, the tk-poly-A site or the SV40, lacZ or AcMNPV polyhedral polyadenylation signals, which are to be included downstream of the nucleic acid sequence of the invention. Additional regulatory elements may include translational enhancers, Kozak sequences and intervening sequences flanked by donor and acceptor sites for RNA splicing, nucleotide sequences encoding secretion signals or, depending on the expression system used, signal sequences capable of directing the expressed polypeptide to a cellular compartment.

Moreover, elements such as origin of replication, drug resistance genes and regulators (as part of an inducible promoter) may also be included.

Furthermore, additional sequences such as e.g. selectable markers may be introduced together with the nucleic acid molecule of interest. The co-transfection with a selectable marker such as dhfr, gpt, G418, neomycin, hygromycin allows the identification and isolation of the transfected cells. The dhfr (dihydrofolate reductase) marker is useful to develop cell lines that carry several hundred or even several thousand copies of the gene of interest. Another useful selection marker is the enzyme glutamine synthase (GS). Using these markers, the cells are grown in selective medium and the cells with the highest resistance are selected.

Preferably, the nucleic acid molecule to be introduced as well as potential regulatory sequences and additional sequences are comprised in an expression vector. Preferably, the vector is a plasmid, cosmid, virus, bacteriophage or another vector used conventionally e.g. in genetic engineering. Non-limiting examples include prokaryotic plasmid vectors, such as the pET-series of expression vectors (Novagen), the pUC-series, pBluescript (Stratagene) or pCRTOPO (Invitrogen), lambda gt11, pJOE, the pBBR1-MCS series, pJB861, pBSMuL, pBC2, pUCPKS, pTACT1 and vectors compatible with expression in mammalian cells like E-027 pCAG Kosak-Cherry (L45a) vector system, pREP (Invitrogen), pCEP4 (Invitrogen), pMC1neo (Stratagene), pXT1 (Stratagene), pSG5 (Stratagene), EBO-pSV2neo, pBPV-1, pdBPVMMTneo, pRSVgpt, pRSVneo, pSV2-dhfr, pIZD35, Okayama-Berg cDNA expression vector pcDV1 (Pharmacia), pRc/CMV, pcDNA1, pcDNA3 (Invitrogen), pSPORT1 (GIBCO BRL), pGEMHE (Promega), pLXIN, pSIR (Clontech), pIRES-EGFP (Clontech), pEAK-10 (Edge Biosystems) pTriEx-Hygro (Novagen) and pCINeo (Promega).

The coding sequences inserted into the vector can be synthesized by standard methods. Ligation of the coding sequences to transcriptional regulatory elements can be carried out using established methods. For vector modification techniques, see Sambrook and Russel, 2001.

In accordance with the present invention, human taste cells capable of continuous proliferation are provided. Whereas continuously growing murine cell lines were found to be obtainable via the expression of a single oncogene (Jat, P. S., & Sharp, P. A., Cell lines established by a temperature-sensitive simian virus 40 large-T-antigen gene are growth restricted at the nonpermissive temperature. *Molecular and Cellular Biology,* 1989, 9(4): 1672-1681), a simple transfer of this immortalization method to human cells is not possible (Shay, J W et al., The frequency of immortalization of human fibroblasts and mammary epithelial cells transfected with SV40 large T-antigen. *Experimental cell research,* 1993, 209 (1): 45-52; Wright, W E, Reversible cellular senescence: implications for immortalization of normal human diploid fibroblasts. *Molecular and Cellular Biology,* 1989, 9(7): 3088-3092) as it was found that this factor does not cause immortalization, but solely a limited life span extension in human cells. After a limited number of cell divisions a crisis occurs in the human cells, which results in the rapid senescence and death of these cells in culture (Shay, J W et al., The frequency of immortalization of human fibroblasts and mammary epithelial cells transfected with SV40 large T-antigen. *Experimental cell research,* 1993, 209(1): 45-52). Accordingly, while it was possible to immortalize numerous different cell types, these methods were not successful in prolonging the life span of human taste cells so far.

The human taste cells of the present invention were originally isolated from taste buds of one human donor, thus representing cells from a single individual. Moreover, during the establishment of the cells of the invention, clonal expansion was employed, thus resulting in a pure cell population derived from a single cell. Accordingly, and in contrast to taste cell preparations described in the art, the present cells are a pure cell population of one particular cell type, which most closely resembles type II taste cells. To the inventors' best knowledge, no pure, stably proliferating human taste cell line exists so far in the art.

The cells of the present invention possess a number of surprising and advantageous features. The phenotype of the parental cells most closely resembles type II taste cells of adult humans, as is evident from RT-PCR analysis of gene expression as well as from endogenous responses to taste molecules measured by means of Fluo-4 calcium imaging assays and FMP fluorescent membrane potential assays. It was surprisingly found that the cells of the present invention are capable of proliferating continuously for at least 35 generations. The BR-HTC8 cells of the present invention possess a pattern of gene expression similar to that of adult mammalian taste cells including the expression of genes encoding taste receptors, ion channels, and signal transduction components known for taste molecule stimulus reception and taste signal transduction and modulation in gustatory processes, as shown in Example 4 and Table 1 below. Moreover, this gene expression profile of an adult human taste cell is maintained in the taste cells of the present invention for at least 35 generations, without the occurrence of a de-differentiation into more immature cells during culture. In addition, the human taste cells of the present invention show known signalling responses when contacted with taste molecules or hormones implicated with modulation of satiety, as shown in Examples 1 and 5 to 8 below. Finally, the human taste cells of the present invention are susceptible to genetic manipulation such as e.g. lenti- or adenoviral introduction of gene expression cassettes or RNA interference as shown in Examples 2 and 3 below.

Accordingly, the cells of the present invention—either as deposited at the DSMZ or derived therefrom, preferably genetically modified as described herein—are particularly useful in the screening and study of taste molecules, satiety hormones, and gustatory signalling molecules/transmitters and the quantitative assessment of the evoked functionally distinct signalling events. They are further useful in the screening and study of modulators of taste perception as well as the study of modulators of gene expression patterns in taste cells, taste cell proliferation, taste cell maturation and differentiation, and taste cell regeneration.

In a preferred embodiment of the cells of the invention, the cells derived from the cells deposited under the DSMZ deposit accession number DSM ACC3169 are genetically engineered BR-HTC8 cells.

The term "genetically engineered" has been defined herein above.

Preferred methods for introducing nucleic acid sequences are as defined above. Preferably, the method should be a method achieving high efficiency of nucleic acid introduction. For example, efficiencies are preferred where the nucleic acid is introduced into at least 30% of the cells, such as at least 50%, or at least 80% and most preferably into all cells. Most preferably, the nucleic acid sequences are introduced into the cells via viral transduction, using for example adenoviral vectors or retroviral vectors, such as e.g. lentiviral virus, as for example described in the appended examples. Whereas adenoviruses do not integrate into the genome, retroviral vectors offer the added advantage that they can mediate integration of the introduced nucleic acid molecule into the genomic DNA of the target cell.

Preferably, the genetically engineered cells differ from the parental cells only in the nucleic acid molecules that have been introduced or removed by the genetic engineering. In other words, apart from these altered nucleic acid molecules, the cells derived from the cells deposited under the DSMZ deposit accession number DSM ACC3169 maintain or essentially maintain the phenotype of the parental cells as defined herein above. The above defined degree of similarity and the methods for determining whether a cell maintains or essentially maintains the phenotype of the parental cells apply mutatis mutandis to the genetically engineered cells of the invention.

In accordance with the present invention, the genetically engineered cells may contain any number of alterations, i.e. removed or added nucleic acid molecules. Preferably, up to 20 alterations are comprised in the genetically engineered cells as compared to the parental cells, i.e. any number of alterations between 1 and 20. More preferably, up to 15 alterations are comprised in the genetically engineered cells, such as e.g. up to 10 alterations, up to 9 alterations, up to 8 alterations, up to 7 alterations, up to 6 alterations, up to 5 alterations, up to 4 alterations, up to 3 alterations, up to 2 alterations and most preferably 1 alteration. It is preferred in accordance with the present invention that the alteration is the addition of exogenous and/or endogenous nucleic acid molecules. Even more preferably, the alteration is the addition of exogenous nucleic acid molecules.

In a preferred embodiment, the genetical engineering comprises the introduction into the cells of at least one nucleic acid molecule selected from the group consisting of a nucleic acid molecule encoding a protein taste receptor, a nucleic acid molecule encoding a hormone receptor, a nucleic acid molecule encoding a signalling molecule, a nucleic acid molecule encoding an anti-senescence and immortalization promoting compound and a nucleic acid molecule that inhibits the expression of a particular expression product, such as receptors, ion channels or signalling molecules.

As defined herein above, said nucleic acid molecule may be an exogenous or endogenous nucleic acid molecule, i.e. one may introduce into the cell a nucleic acid sequence that is not present in the parental cell or the introduction may result in the expression or increased expression of a an expression product that is present in the parental cell but is either not expressed or whose expression is to be enhanced.

The term "taste receptors", as used herein, relates to receptors embedded in the plasma membrane of taste cells that bind taste molecules including sweet, bitter, salty, sour and umami compounds as well as fatty acids. Typically, these taste receptors are either G protein-coupled receptors with several transmembrane domains or ion channels.

The binding of taste molecules leads to the activation of taste receptors, which triggers signals and signal transduction events. Perception of basic taste qualities including sweet, bitter, salty, fatty, sour, umami as well as of somatosensory sensory qualities including pungency, temperature, touch, pressure, texture and other tactile stimuli are sensed and brought about by taste GPCRs (sweet, bitter, umami/amino acids, fatty acids) as well as ion channels (e.g. salty and sour taste, pungency, temperature) and molecules involved in transport of taste molecules such as e.g. fatty acid scavengers including CD36.

The term "hormone receptors", as used herein, relates to receptors embedded in the plasma membrane of taste cells that bind hormones. Hormones are compounds that function as chemical messengers released by a cell or a gland in one part of the body sending out messages that affect cells in other parts of the organism thus transporting a signal from one cell to another. Non-limiting examples for hormones with implication in taste and food intake regulation are oxytocin, insulin, leptin, ghrelin, serotonin (HTR), melanocortins, melantonin, GLP1, GLP2, glucagon, incretin, adiponectin, melanocortin, opiods, endocannabinoids and peptide YY (PYY).

The term "signalling molecules", as used herein, relates to signalling molecules involved in taste perception, such as for example molecules downstream of taste and/or hormone receptors e.g. intracellular second messengers such as $Ca^{2+}$, IP3, DAG, cGMP, or cAMP as well as secreted molecules such as e.g. ATP, serotonin and derivatives thereof.

The term "anti-senescence and immortalization promoting compound", as used herein, relates to factors capable of extending the life span of a cell while at the same time avoiding its senescence. Non-limiting examples of such compounds include hTERT, bmi-1, the combination of hTERT and bmi-1, oct-4, c-myc, HPVE6/E7, SV 40 temperature-sensitive large T tsA58, E2F1 or nucleic acid sequences mediating RNA interference against the p53 gene mRNA. All these compounds are well known in the art and have been described, e.g. in Lodish, H. et al. 2006. *Molecular Cell Biology* (Sixth ed.). New York: W.H. Freeman and Company.

The term "nucleic acid molecule that inhibits the expression of a particular expression product, such as receptors, ion channels or signalling molecules" is as defined herein above and includes for example antisense nucleic acid molecules, small interfering RNAs (siRNAs), short hairpin RNAs (shRNAs) and microRNAs (miRNAs). Most preferably, said nucleic acid molecule is an "shRNA", as defined herein above. Targeted inhibition of the expression of molecules involved in taste perception, such as e.g. taste receptors, ion channels hormone receptors or signalling molecules can be employed in order to elucidate signalling pathways involved in taste perception.

In a more preferred embodiment, the taste receptors, hormone receptors and/or signalling molecules are selected from the molecules shown in Table 1 below.

In an even more preferred embodiment, the taste receptors are selected from the group consisting of transient receptor potential V1 (TRPV1), transient receptor potential A1, (TRPA1), epithelial sodium channel alpha subunit (SCNN1A), epithelial sodium channel beta subunit (SCNN1B), epithelial sodium channel gamma subunit (SCNN1G), epithelial sodium channel delta subunit (SCNN1D), transient receptor potential ML3 (TRPML3), transient receptor potential M5 (TRPM5), taste receptor, type 1, member 1 (T1R1), taste receptor, type 1, member 2 (T1R2), taste receptor, type 1, member 3 (T1R3), taste receptor, type 2, member 38 (TAS2R38), taste receptor, type 2, member 44 T(AS2R44), taste receptor, type 2, member 1 (TAS2R1), taste receptor, type 2, member 2 (TAS2R2), taste receptor, type 2, member 3 (TAS2R3), taste receptor, type 2, member 4 (TAS2R4), taste receptor, type 2, member 5 (TAS2R5), taste receptor, type 2, member 7 (TAS2R7), taste receptor, type 2, member 8 (TAS2R8), taste receptor, type 2, member 9 (TAS2R9), taste receptor, type 2, member 10 (TAS2R10), taste receptor, type 2, member 13 (TAS2R13), taste receptor, type 2, member 14 (TAS2R14), taste receptor, type 2, member 16 (TAS2R16), taste receptor, type 2, member 39 (TAS2R39), taste receptor, type 2, member 40 (TAS2R40), taste receptor, type 2, member 41 (TAS2R41), taste receptor, type 2, member 42 (TAS2R42), taste receptor, type 2, member 43 (TAS2R43), taste receptor, type 2, member 45 (TAS2R45), taste receptor, type 2, member 46 (TAS2R46), taste receptor, type 2, member 47 (TAS2R47), taste receptor, type 2, member 48 (TAS2R48), taste receptor, type 2, member 49 (TAS2R49), taste receptor, type 2, member 50 (TAS2R50), taste receptor, type 2, member 60 (TAS2R60), glutamate receptor, metabotropic 1 (mGlu1), glutamate receptor, metabotropic 4 (mGlu4), polycystic kidney disease 2-like 1, (PKD2L1), G-protein coupled receptor 120 (GPR120), G-protein coupled receptor 40 (GPR40), CD36 molecule (CD36), and potassium inwardly-rectifying channel, subfamily J, member 1 (ROMK).

In another even more preferred embodiment, the hormone receptors are selected from the group consisting of oxytocin receptor (OXTR), leptin receptor (LEPR), serotonin receptors (HTRs), and melanocortin receptors (MCRs).

In a further more preferred embodiment, the signalling molecules are selected from the non-limiting group consisting of gustducin, transient receptor potential M5 (TRPM5), phosholipase C beta 2 (PLCb2), inositoltriphosphate receptor 3 (IP3R3), phospholipase C delta 4 (PLCD4), chemokine (C-X-C motif) ligand 14 (CXCL14), adrenergic, alpha-1A-, receptor (ADRA1A), adrenergic, beta-1-, receptor (ADRB1), adenosine A2b receptor (ADORA2B), potassium voltage-gated channel subfamily C member 2 (KCNC2), potassium voltage-gated channel, KQT-like subfamily, member 1 (KCNQ1), potassium voltage-gated channel, subfamily H (eag-related), member 2 (KCNH2), guanine nucleotide binding protein (G protein), gamma 13 (GNG13), guanine nucleotide binding protein (G protein), beta polypeptide 3 (GNB3), guanine nucleotide binding protein (G protein), alpha 13 (GNA13), guanine nucleotide binding protein (G protein), alpha 11 (GNA11), guanine nucleotide binding protein (G protein), alpha 14 (GNA14), guanine nucleotide binding protein (G protein), alpha 12 (GNA12), guanine nucleotide binding protein (G protein), beta polypeptide 1 (GNB1), guanine nucleotide-binding protein G(olf) subunit alpha (GNAL), guanine nucleotide binding protein (G protein), alpha 15 (GNA15), guanine nucleotide-binding protein G(q) subunit alpha (GNAQ), pannexin 1 (PANX1), purinergic receptor P2Y, G-protein coupled, 12 (P2RY12), purinergic receptor P2X, ligand-gated ion channel, 7 (P2RX7), potassium voltage-gated channel, shaker-related subfamily, member 1 (KCNA1), potassium voltage-gated channel, shaker-related subfamily, member 2 (KCNA2), potassium voltage-gated channel, shaker-related subfamily, member 3 (KCNA3), potassium voltage-gated channel, shaker-related subfamily, member 5 (KCNA5), potassium voltage-gated channel, shaker-related subfamily, member 2 (KCNA6), potassium voltage-gated channel, Shab-related subfamily, member 1 (KCNB1), potassium voltage-gated channel, Shab-related subfamily, member 1 (KCNB2), potassium voltage-gated channel subfamily C member 1 (KCNC1), phosphodiesterase 1A (PDE1A), sodium channel, voltage-gated, type II, alpha subunit (SCN2A), sodium channel, voltage-gated, type III, alpha subunit (SCN3A), sodium channel, voltage-gated, type IX, alpha subunit (SCN9A), amiloride-sensitive cation channel 1 neuronal (ACCN1), amiloride-sensitive cation channel 2 neuronal (ACCN2), and amiloride-sensitive cation channel 3 neuronal (ACCN3).

Database accession numbers for these preferred receptors and signalling molecules are provided in Table 1 below.

In another more preferred embodiment, the anti-senescence and immortalization promoting nucleic acid molecules are the SV40 temperature-sensitive large TtsA58 gene and the human hTERT gene.

As is shown in example 2, the cells of the present invention may be further altered by a retroviral transduction of the SV40 temperature-sensitive large T temperature sensitive tsA58 gene (large TtsA58) and the human telomerase reverse transcriptase (hTERT) gene. Even though the cells of the present invention are already stably proliferating, additional expression of said genes can provide further protection from senescence and other anti-proliferative effects and further improved proliferation properties due to stable genomic integration of the retroviral gene expression cassettes.

In another more preferred embodiment, the shRNA is an shRNA against the taste receptor TAS2R16 and/or an shRNA against the taste receptor TAS2R44.

As discussed herein above, introduction of an shRNA against a particular target molecule can be employed to down-regulate the expression of said target molecule. Cells with a down-regulated expression of particular signalling molecules can for example be employed as control cells to verify the involvement of a specific signalling pathway, as further discussed herein below.

Preferably, the shRNA against the taste receptor TAS2R16 is selected from the sequence GCTTGAGTCCTTGACAATTAT (SEQ ID NO:1) or the sequence GCTTTCATCTTAATGCATTCC (SEQ ID NO:2) while the shRNA against the taste receptor TAS2R44 is selected from the sequence GTGGTAGTGGTTCTATTTGTT (SEQ ID NO:3) or the sequence GGTTTGCTCTGGGTATTATTA (SEQ ID NO:4).

It will be appreciated that after performing genetical engineering of the cells of the invention, a single successfully modified cell may be isolated and clonally expanded in order to obtain a pure cell line.

The term "isolating" refers to the separation of a single cell from the initial culture dish and its transfer to a new culture vessel, such as for example a different cell culture dish or flask. Methods of isolation of cells are well known in the art and include, without being limiting, mechanical isolation, limited dilution as well as cell sorting approaches. Mechanical isolation relates to the selection and isolation of a cell by e.g. manual picking of the cell, where necessary under a microscope, automated picking by use of a robot or laser-capture micro-dissection. Manual picking of a cell may be performed by methods known in the art, such as for example aspiration of the cell into the tip of a pipette. Cell sorting approaches include, for example, magnetic activated cell sorting (MACS), flow cytometry activated cell sorting (FACS) or panning approaches. Such methods for cell isolation are well known in the art and have been described, e.g. in Dainiak et al., ((2007) Adv Biochem Eng Biotechnol. 2007; 106:1-18), Murray ((2007) Acta Histochemica 109:171-176) or Tung et al. ((2007) Clin Lab Med. 27:453-468).

The term "expanding", in accordance with the present invention, refers to a multiplication of cells, thus resulting in an increase in the total number of cells. For example, cells can be expanded to at least 100 times their original number, such as at least 1.000 times their original number, preferably at least 10.000 times their original number, such as at least 100.000 times their original number etc. Expansion of cells may be achieved by any known method, e.g. by culturing the cells under appropriate conditions to high density or confluence and subsequently splitting (or passaging) of the cells, as described herein above.

The term "clonally expanding" refers to the fact that one single cell is expanded to a plurality of cells, thus resulting in a cell culture of clones of the initial cell.

The present invention further relates to the human taste cells of the invention for use in research.

The parental taste cells of the present invention as well as cells derived thereof, such as e.g. genetically engineered cells as described herein above, can be employed for research into taste perception and the associated signalling responses. For example, the taste cells of the present invention are particularly suitable for testing endogenous responses to taste molecules and hormones modulating taste and satiety. Moreover, the cells can be employed for screening for taste modulators and modulators of satiety hormone function in low-, medium-, or high-throughput screening formats, thereby reducing the need for primary cell cultures and in vivo studies. Experimental setups and methods to identify and/or assess effects of a potential drug including, for example, target-site and -specificity, toxicity or bioavailability are well-known to the person skilled in the art. The proliferating human taste cells of the present invention can further be subject to studies relating to, e.g., differentiation studies or tests for safety and efficacy of drugs.

It is a unique and special feature of the human taste cells of this invention that the cells show the endogenous response of naturally occurring taste cells, as they express a defined portfolio of taste receptors, hormone receptors, ion channels, and signalling transduction components that is normally lost in primary cell cultures or immortalised human taste cells. Preferred methods for using the cells of the invention in research applications are described in more detail below.

Accordingly, the present invention further relates to an in vitro method for analysing the signalling response of taste cells to a molecule involved in taste signalling, the method comprising: (i) contacting the proliferating human taste cells of the invention with a molecule involved in taste signalling; and (ii) determining the signalling response elicited by the molecule involved in taste signalling in the cells.

The term "signalling response of taste cells", as used herein, relates to a response of said cells to a stimulus, such as for example the activation of taste receptors, hormone receptors, ion channels, and signal transduction components involved in taste molecule stimulus reception. Such signalling responses include, without being limiting, changes in intracellular calcium, cellular membrane potential, cellular proliferation rate, gene and/or protein expression patterns, transmitter or hormone release, pH value and/or availability of messengers such as IP3, cGMP or cAMP. Means and methods to detect a signalling response are well known to the skilled person (for review see: Rudolf et al., Investigating second messenger signalling in vivo, Meth. Enzymol. 2012, 505, 363-82; Casey, J. R. et al., Sensors and regulators of intracellular pH, Nat Rev Mol Cell Biol 2010, 11, 50-61). For example, changes in intracellular calcium levels can be detecting by measuring the Fluo4-dependent fluorescence in the cell. Additionally, changes in cellular membrane potential can be determined using voltage-sensitive dyes including FLIPR fluorescent membrane potential dye. Means and methods to determine the cellular proliferation rate and to determine gene and/or protein expression patterns have been described herein above. The release of transmitters or hormones can for example be determined by ATP-sensor cells (Huang & Roper, 2010) and Enzyme-Linked Immunosorbent Assay (ELISA). Moreover, the availability of messengers such as IP3, cGMP or cAMP can for example be determined by reporter assays (Fitzgerald, Mannan, Dytko, Wu, & Nambi, 1999).

Molecules involved in taste signalling include for example taste molecules, hormones as well as signalling molecules/transmitters.

The term "taste molecule", as used herein, relates to a compound that can elicit perception of taste. Preferably, the taste molecule can elicit perception of taste belonging to the basic taste modalities sweet, bitter, umami, fatty, salty and sour. Taste molecules include, without being limiting, sugars, such as e.g. sucrose, fructose, glucose or lactose; artificial sweeteners, such as e.g. saccharin, sucralose or aspartame; salt; bitter tastants, such as e.g. denatonium, saccharin, caffeine, quinine, phenylthiourea, humulone, (iso)humulone or gluconasturtiin; umami tastants, such as e.g. monosodium glutamate-sodium salt, nucleotides or aspartate; acids, such as e.g. citric acid, tartaric acid or acetic acid but also fatty acids or compounds that have covalently attached fatty acids.

Taste molecules may be obtained from any source known in the art, such as e.g. plant extracts or may be produced synthetically or semi-synthetically. Means and methods of obtaining taste molecules are well known to the skilled person and include, without being limiting, fractionating extracts, such as plant extracts, or from an existing compound library which may for example be commercially obtained. As used herein, the term "library" refers to a collection of molecules. A library can contain a small or a large number of different molecules, varying from about ten molecules to several thousand molecules or more. Such molecules can be naturally occurring molecules, recombinant molecules, or synthetic molecules.

The term "signalling molecules/transmitter", as used herein, relates to signalling molecules involved in the intracellular and intercellular transmittal of the signal elicited by a taste or hormone receptor. Non-limiting examples of such signalling molecules/transmitter include adenosine, adenosine monophosphate, adenosine triphosphate, serotonin, norepinephrine, cAMP, cGMP, IP3, DAG.

The term "hormones" includes the non-limiting examples oxytocin, insulin, leptin, ghrelin, serotonin (HTR), melanocortins, melantonin, GLP1, GLP2, glucagon, incretin, adiponectin, melanocortin, opiods, endocannabinoids and peptide YY (PYY).

In accordance with this method of the invention, the human taste cells of the invention are contacted with a molecule involved in taste signalling and the signal response elicited by said molecule in the cells is determined.

For example, where the signal elicited by the molecule involved in taste signalling is an alteration in intracellular $Ca^{2+}$ concentration, said method can comprise the following steps:

(1) culturing the cells of the present invention in the absence of the molecule involved in taste signalling;
(2) staining the cells with an appropriate $Ca^{2+}$ sensitive fluorescent dye;
(3) measuring the fluorescence;
(4) subsequently adding the molecule involved in taste signalling to the cells; and
(5) measuring the relative fluorescence change elicited by addition of the molecule involved in taste signalling as compared to the fluorescence measured in step (3).

Alternatively, where the signal elicited by the taste molecule is an alteration of the cellular membrane potential, said method can comprise the following steps:

(1) culturing the cells of the present invention in the absence of the molecule involved in taste signalling;
(2) staining the cells with an appropriate membrane potential sensitive fluorescent dye;
(3) measuring the fluorescence;
(4) subsequently adding the molecule involved in taste signalling to the cells; and
(5) measuring the fluorescence change elicited by addition of the molecule involved in taste signalling as compared to the fluorescence measured in step (3).

If a change in fluorescence is detected in step (5), it can be concluded that the molecule involved in taste signalling has elicited a signalling response in the cells of the invention. Moreover, by determining the relative amount of change of fluorescence, a quantitative analysis of the strength of the signalling response can be carried out.

In addition, the same method may be carried out in parallel with control cells known to be unresponsive to said molecule involved in taste signalling and the signal elicited may be compared between the cells of the present invention and the control cells, thereby confirming that the elicited signal depends on the taste cell-specific properties of the cells of the invention described above.

Preferably, the cells are cultured on a solid support in a monolayer, such as e.g. a culture dish or a microscope slide. Suitable cell culture media are as defined herein above.

The present invention further relates to an in vitro method of identifying an agent capable of eliciting a taste response in taste cells, the method comprising: (i) adding a test compound to the human taste cells of the invention and measuring the signalling response elicited by the test compound in the cells; and (ii) comparing the signalling response obtained in (i) with the signalling response elicited in the human taste cells of the invention by (a) known molecule(s) involved in taste signalling; wherein an identical or substantially identical signalling response determined in (ii) indicates that the agent is an agent capable of eliciting a taste response.

The term "an agent capable of eliciting a taste response in taste cells", as used herein, relates to a compound able to trigger an intracellular or intercellular signalling cascade in taste cells that mediates a taste perception.

Essentially any compound can be assayed as a test compound in this method according to the present invention. Such compounds include e.g. small molecules, such as organic or inorganic molecules. Organic molecules relate or belong to the class of chemical compounds having a carbon basis, the carbon atoms linked together by carbon-carbon bonds, including biological entities such as e.g. proteins, sugars, nucleic acids, lipids. The original definition of the term organic related to the source of chemical compounds, with organic compounds being those carbon-containing compounds obtained from plant or animal or microbial sources. Organic compounds can be natural or synthetic. Small organic molecules preferably have a molecular weight of about 500 Da or below. Inorganic compounds are derived from mineral sources and include all compounds without carbon atoms (except carbon dioxide, carbon monoxide and carbonates). There are many suppliers of such compounds, including Sigma (St. Louis, Mo.), Aldrich (St. Louis, Mo.), Sigma-Aldrich (St. Louis, Mo.), Fluka Chemika-Biochemica Analytika (Buchs, Switzerland), for example. In addition, compounds to be analysed may be synthesized by methods known in the art. The compounds to be tested as potential agents capable of eliciting a taste response in taste cells can be dissolved in aqueous or organic, such as e.g., DMSO-based, solutions.

Test compounds may be comprised in compound libraries of diverse or structurally similar compounds (e.g, combinatorial chemistry synthesized libraries). In some embodiments, the test substance will include naturally occurring taste compounds (e.g., derived from plant extracts and the like). Test substances can be obtained from fractionating extracts or from a library, as described herein above with regard to taste molecules. A plurality of test compounds in a library can be assayed simultaneously. Optionally, test compounds derived from different libraries can be pooled for simultaneous evaluation. A library can comprise a random collection of molecules. Alternatively, a library can comprise a collection of molecules having a bias for a particular sequence, structure, or conformation. Methods for preparing libraries containing diverse populations of various types of molecules are known in the art (Brenk, R. et al., Lessons Learnt from Assembling Screening Libraries for Drug Discovery for Neglected Diseases, Chem Med Chem 2008, 3, 435-444, Quinn J. R. et al., Developing a Drug-like Natural Product Library, *J. Nat. Prod.* 2008, 71, 464-468). Numerous libraries are also commercially available.

When referring to a "substantially identical signalling response", the type of the response is referred to rather than the strength of the response. Accordingly, where the known taste molecule elicits for example an increase in intracellular calcium levels, a substantially identical response is achieved when the test compound also elicits an increase in intracellular calcium levels, irrespective of whether additional effects are also elicited.

The strength of the signal, such as e.g. the relative increase in intracellular calcium level, does not have to be identical but is nonetheless preferred that the strength of the signal is in the same magnitude, i.e. within 20% of the strength of the signal obtained when employing the known taste molecule, more preferably within 10%, even more preferably within 5% of the strength of the signal obtained when employing the known taste molecule. Where both the type of the signalling response and the strength of the signal is the same as when employing the known taste molecule, the signalling response is considered to be identical.

All other definitions and preferred embodiments provided herein above with regard to the cells of the invention but also the method for analysing the signalling response of taste cells to a molecule involved in taste signalling apply mutatis mutandis also to this method of identifying an agent capable of eliciting a taste response in taste cells.

In accordance with this method of the invention, the (proliferating) human taste cells of the invention are contacted with a test compound and the signalling response elicited by said molecule in the cells is determined and compared to the signalling response elicited by a known taste molecule.

For example, where the signal elicited by the taste molecule is an alteration in intracellular $Ca^{2+}$ concentration, said method can comprise the following steps:

(1) culturing the cells of the present invention in the absence of the test compound;

(2) staining the cells with an appropriate $Ca^{2+}$ sensitive fluorescent dye;

(3) measuring the fluorescence;

(4) subsequently to step (3) adding the test compound to the cells and measuring the relative fluorescence change elicited by addition of the test compound as compared to the fluorescence measured in step (3); and (5) comparing the relative fluorescence change obtained in (4) with the relative fluorescence change elicited by a known taste molecule.

It will be appreciated that the relative fluorescence change elicited by a known taste molecule as referred to in (5) may be obtained in the same way as the relative fluorescence change elicited by addition of the test compound, i.e. by the steps of:

(1-i) culturing the cells of the present invention in the absence of the known taste molecule;

(2-i) staining the cells with an appropriate $Ca^{2+}$ sensitive fluorescent dye;

(3-i) measuring the fluorescence; and (4-i) subsequently to step (3-i) adding the known taste molecule to the cells and measuring the relative fluorescence change elicited by addition of the known taste molecule as compared to the fluorescence measured in step (3-i).

Alternatively, where the signal elicited by the taste molecule is an alteration of the cellular membrane potential, said method can comprise the following steps:

(1) culturing the cells of the present invention in the absence of the test compound;

(2) staining the cells with an appropriate membrane potential sensitive fluorescent dye;

(3) measuring the fluorescence;

(4) subsequently to step (3) adding the test compound to the cells and measuring the relative fluorescence change elicited by addition of the test compound as compared to the fluorescence measured in step (3); and (5) comparing the relative fluorescence change obtained in (4) with the relative fluorescence change elicited by a known taste molecule.

As outlined above, the relative fluorescence change elicited by a known taste molecule as referred to in (5) may be obtained in the same way as the relative fluorescence change elicited by addition of the test compound, i.e. by the steps of:

(1-i) culturing the cells of the present invention in the absence of the known taste molecule;

(2-i) staining the cells with an appropriate membrane potential sensitive fluorescent dye;

(3-i) measuring the fluorescence; and (4-i) subsequently to step (3-i) adding the known taste molecule to the cells and measuring the relative fluorescence change elicited by addition of the known taste molecule as compared to the fluorescence measured in step (3-i).

Determining the relative fluorescence change elicited by a known taste molecule may be carried out in parallel to each screening assay for assaying test compounds or may be carried out prior to screening of test compounds and the determined relative fluorescence change may be used for comparison in all subsequent screening approaches.

If a relative fluorescence change is detected for both the test compound and the known taste molecule, it can be concluded that the test compound has elicited an identical or substantially identical signalling response as compared to the known taste molecule.

To confirm that the test compound is capable of eliciting a taste perception and to additionally analyse which receptors or downstream signalling molecules are involved in elucidating the signalling response referred to above, several approaches can be envisaged. For example, the signalling response elicited may be further analysed in taste cells known to be deficient for one or more components of a signalling pathway. In this regard, cells naturally deficient in said molecule(s) may be employed or, alternatively, genetically engineered cells of the present invention may be employed, where the expression of a particular receptor or signalling molecules has been inhibited, for example by using RNA interference techniques. Similarly, gain-of-function variants of the cells of the present invention may be employed to demonstrate for example an increased signalling response when one (or more) receptor or signalling molecule is more strongly expressed. Finally, the test compound identified as an agent capable of eliciting a taste response in taste cells may also be administered to a human subject in order to verify the taste perception elicited by said compound.

The screening for agents or modulators referred to in the present invention may be carried out by using high throughput screening assays (HTS). High-throughput assays, independently of being biochemical, cellular or other assays, generally may be performed in wells of microtiter plates, wherein each plate may contain, for example 96, 384 or 1536 wells. Handling of the plates, including incubation at temperatures other than ambient temperature, and bringing into contact of test compounds with the assay mixture is preferably effected by one or more computer-controlled robotic systems including pipetting devices. In case large libraries of test compounds are to be screened and/or screening is to be effected within short time, mixtures of, for example 10, 20, 30, 40, 50 or 100 test compounds may be added to each well. In case a well exhibits a signal, said mixture of test compounds may be de-convoluted to identify the one or more test compounds in said mixture giving rise to the observed signal.

Furthermore, the compound identified by any of the methods described herein may be further optimized in its properties. Accordingly, the compounds identified by the present methods may be regarded as "lead compounds", from which further modified and potentially improved compounds can be developed.

The identified lead compounds may for example be optimized by modifying the compound to achieve: (i) modified spectrum of activity, (ii) improved potency, (iii) decreased toxicity (improved therapeutic index), (iv) decreased side effects, (v) modified onset of action, duration of effect, (vi) modified physico-chemical parameters (solubility, hygroscopicity, color, taste, odor, stability, state), and/or (vii) optimised application form and route. Means and methods to achieved such modification include, without being limiting (a) esterification of carboxyl groups, (b) esterification of hydroxyl groups with carboxylic acids, (c) esterification of hydroxyl groups to, e.g. phosphates, pyrophosphates or sulfates or hemi-succinates, (d) formation of pharmaceutically acceptable salts, (e) formation of pharmaceutically acceptable complexes, (f) synthesis of pharmacologically active polymers, (g) introduction of hydrophilic moieties, (h) introduction/exchange of substituents on aromates or side chains, change of substituent pattern, (i) modification by introduction of isosteric or bioisosteric moieties, (j) synthesis of homologous compounds, (k) introduction of branched side chains, (l) conversion of alkyl substituents to cyclic analogues, (m) derivatisation of hydroxyl groups to ketales, acetales, (n) N-acetylation to amides, phenylcarbamates, (o) synthesis of Mannich bases, imines, and/or (p) transformation of ketones or aldehydes to Schiffs bases, oximes, acetales, ketales, enolesters, oxazolidines, thiazolidines or combinations thereof.

The various steps recited above are generally known in the art.

The present invention further relates to an in vitro method of identifying a modulator of taste signalling, comprising the steps of: (i) determining the signalling response elicited in the (proliferating) human taste cells of the invention by a known molecule involved in taste signalling in the presence of a test compound; and (ii) comparing the signalling response elicited in the cells in the presence of the test compound as determined in step (i) with the signalling response elicited in the cells in the absence of the test compound, wherein an alteration in the signalling response determined in (i) as compared to the signalling response in the absence of the test compound indicates that the test compound is a modulator of taste signalling.

In accordance with this embodiment, "a modulator of taste signalling" is a compound capable of altering the signalling response elicited by a known molecule involved in taste signalling, such as the above defined taste molecules, hormones or signalling molecules/transmitter. Thus, the modulator is not necessarily a molecule involved in taste signalling itself, but instead interacts with such a molecule involved in taste signalling, thereby altering its effect on the taste cell. Said interaction may, for example, lead to an inhibition of a particular taste signalling pathway but may also lead to an enhancement (i.e. an increased signalling) of a particular taste signalling pathway. Moreover, said interaction may lead to a delayed onset of the signalling response or to an extended or shortened signalling response, i.e. a response of longer or shorter duration as compared to the signal elucidated by the known molecule involved in taste signalling in the absence of the test compound. The latter effects can for example be measured by an assay determining the time it takes until the effect elicited by the test compound takes effect and/or the duration of the signal, comprising the following steps of: (i) determining the signalling response elicited in the proliferating human taste cells of the invention by a known molecule involved in taste signalling in the presence of a test compound and determination of the time that has passed since addition of the test compounds and/or the duration of said signal; and (ii) comparing the signalling response elicited and the time that has passed since addition of the test compounds and/or the duration of the signal in the cells in the presence of the test compound as determined in step (i) with the signalling response elicited in the cells and the time that has passed since addition of the test compounds and/or the duration of the signal in the absence of the test compound, wherein an alteration in the signalling response and time and/or duration of signal determined in (i) as compared to the signalling response and time and/or duration of signal in the absence of the test compound indicates that the test compound is a modulator of taste signalling. With this assay, in particular a delayed onset of the effect elicited by the test compounds can be discriminated from an accelerated onset of the effect and/or an altered duration of the signalling response can be determined. Such compounds may for example be advantageous in order to lengthen pleasurable taste sensations or to shorten unwanted taste sensations.

A modulator may perform any one or more of the following effects in order to alter the signalling capabilities of the target protein: (i) the transcription of the gene encoding the protein to be modulated is altered, i.e. the level of mRNA is altered, (ii) the translation of the mRNA encoding the protein to be modulated is altered, and (iii) the protein performs its biochemical and/or cellular function with altered efficiency in the presence of the modulator.

Compounds falling in class (i) include compounds interfering with the transcriptional machinery and/or its interaction with the promoter of said gene and/or with expression control elements remote from the promoter such as enhancers. Preferably, said compounds directly alter the transcription of the protein to be modulated, i.e. the mRNA level of said protein is altered as a direct consequence of the presence of the compound. Compounds of class (ii) comprise antisense constructs and constructs for performing RNA interference (e.g. siRNA, shRNA, miRNA) well known in the art (see, e.g. Zamore (2001) Nat. Struct. Biol. 8(9), 746; Tuschl (2001) Chem biochem. 2(4), 239). Preferably, these compounds directly alter the translation of the mRNA encoding the protein to be modulated, e.g. in the case of siRNA by specifically binding to the mRNA of said protein. Compounds of class (iii) interfere with the molecular function of the protein to be modulated, in the present case for example the activation of a taste receptor and its subsequent down-stream signalling activity. Accordingly, active site binding compounds, in particular compounds capable of directly binding the protein to be modulated are preferred. Class (iii) also includes compounds which do not necessarily bind directly to the protein to be modulated, but still interfere with its activity, for example by binding to and/or modulating the function or expression of members of a pathway which comprises the protein to be modulated. Preferably, these members are downstream of the protein to be modulated within said pathway.

Essentially any compound can be assayed as a potential modulator in the method according to the present invention. Such compounds include e.g. small molecules and interfering nucleic acid molecules, as defined herein above.

Modulation of the human taste cell response to molecules involved in taste signalling may be assayed by comparing the response of the cells of the present invention to treatment with a putative modulator to the response of an untreated control sample or a sample containing a known modulator with known properties and activities. The signalling response of the taste cells of the present invention to a known taste molecule is determined in the presence and absence of the test compound.

For example, where the signal elicited by the known molecule involved in taste signalling is an alteration in intracellular $Ca^{2+}$ concentration, said method can comprise the following steps:

(1) culturing the cells of the present invention in the presence of the test compound;
(2) staining the cells with an appropriate $Ca^{2+}$ sensitive fluorescent dye;
(3) measuring the fluorescence; and
(4) subsequently to step (3) adding the known molecule involved in taste signalling to the cells and measuring the relative fluorescence change elicited by addition of the test compound as compared to the fluorescence measured in step (3); and
(5) comparing the relative fluorescence change obtained in (4) with the relative fluorescence change elicited by a known taste molecule in the absence of the test compound.

Again, it will be appreciated that the relative fluorescence change elicited by a known molecule involved in taste signalling in the absence of the test compound as referred to in (5) may be obtained in the same way as the relative fluorescence change elicited in the presence of the test compound, i.e. by the steps of:

(1-i) culturing the cells of the present invention in the absence of the test compound;
(2-i) staining the cells with an appropriate $Ca^{2+}$ sensitive fluorescent dye;
(3-i) measuring the fluorescence; and
(4-i) subsequently to step (3-i) adding the known molecule involved in taste signalling to the cells and measuring the relative fluorescence change elicited by addition of the known molecule involved in taste signalling as compared to the fluorescence measured in step (3-i).

Alternatively, where the signal elicited by the known molecule involved in taste signalling is an alteration of the cellular membrane potential, said method can comprise the following steps:

(1) culturing the cells of the present invention in the presence of the test compound;
(2) staining the cells with an appropriate membrane potential sensitive fluorescent dye;
(3) measuring the fluorescence; and
(4) subsequently to step (3) adding the known molecule involved in taste signalling to the cells and measuring the relative fluorescence change elicited by addition of the test compound as compared to the fluorescence measured in step (3); and
(5) comparing the relative fluorescence change obtained in (4) with the relative fluorescence change elicited by the known molecule involved in taste signalling in the absence of the test compound.

As outlined above, it will be appreciated that the relative fluorescence change elicited by the known molecule involved in taste signalling in the absence of the test compound as referred to in (5) may be obtained in the same way as the relative fluorescence change elicited in the presence of the test compound, i.e. by the steps of:

(1-i) culturing the cells of the present invention in the absence of the test compound;
(2-i) staining the cells with an appropriate membrane potential sensitive fluorescent dye;
(3-i) measuring the fluorescence; and
(4-i) subsequently to step (3-i) adding the known molecule involved in taste signalling to the cells and measuring the relative fluorescence change elicited by addition of the known molecule involved in taste signalling as compared to the fluorescence measured in step (3-i).

In accordance with this embodiment of the present invention, an alteration in the signalling response determined in the presence of the test compound as compared to the signalling response in the absence of the test compound indicates that the test compound is a modulator of taste signalling.

Preferably, the alteration is an inhibition or an enhancement of the signalling response elicited in the proliferating human taste cells of the invention by a known molecule involved in taste signalling.

Where the alteration is an inhibition, it is preferred that the modulator decreases the signalling response of the known molecule involved in taste signalling by at least 10%, such as by at least 25%, such as by at least 50%, preferably by at least 75%, more preferred by at least 90%, even more preferred by at least 95% such as by at least 98% and most preferably by 100%. It will be appreciated that an inhibition by 100% refers to a total inhibition of the signalling response elucidated by the known molecule involved in taste signalling.

Where the alteration is an enhancement, it is preferred that the modulator increases the signalling response to at least 110% of the signalling response of the known molecule involved in taste signalling in the absence of said test compound, preferably to at least 150%, such as at least 200%, such as at least 500%, more preferably at least 1000% and most preferably at least 2000%. It will be appreciated that an enhancement of 200% refers to a 2-times increase of the signalling response elucidated by the known molecule involved in taste signalling, while an enhancement of e.g. 2000% refers to a 20-times increase of the signalling response elucidated by the known molecule involved in taste signalling.

All other definitions and preferred embodiments provided herein above with regard to the cells of the invention but also the methods described above apply mutatis mutandis also to this method of identifying a modulator of taste signalling.

It is understood that all other conditions in the various methods described herein above, such as humidity or temperature of culturing conditions are to be kept as constant as possible, unless indicated otherwise. In accordance with this method of the invention, taste modulators can be identified that may be employed in modifying food or other orally ingested products, such as medicinal products. For example, a compound found to enhance the response of the taste cell to a particular taste molecule can be used to enhance the given taste or flavour of a food product containing said taste molecule. A compound found to decrease the response of the taste cell to a particular taste molecule indicates that the test compound is capable of masking, blocking or suppressing a taste quality. Accordingly, such a compound can be used to reduce a given taste or flavour of a food product containing said taste molecule. This may for example be of particular relevance for medicinal products, such as e.g. cough syrups, which are often associated with an unpleasant taste.

In a preferred embodiment of the methods of the invention, the signalling response is selected from the group consisting of an alteration in (i) intracellular calcium signalling, and (ii) cellular membrane potential.

Candidate molecules identified by any of the assays described above may be further validated by additionally methods, which are well known in the art. These include animal behavioural testing e.g. bottle-preference/aversion tests, sensory testing e.g. in human taste panels, signal transduction testing, and physiological methods such as e.g. analysis of blood parameters including concentrations of glucose, triglycerides, and satiety hormones.

Molecules and stimuli identified by assays employing taste cells described in the invention may be added to food and food products. "Food products" include all nutritional products for uptake via the oral cavity, including human as well as pet food products.

The present invention further relates to a kit comprising the cells of the present invention. The components of the kit may be packaged in one or more containers such as one or more vials. The vials may, in addition to the cells, comprise preservatives or buffers for storage. In addition, the kit may contain instructions for use.

The present invention further relates to the human taste cells of the present invention for use in medicine. These uses include for example the identification of compounds modulating satiety for the treatment of obesity or for the discovery of compounds enhancing taste sensations, thus reducing the uptake of high-caloric food ingredients like fat and sugar. Furthermore, the unpleasant or unwanted taste of a medicament can be covered or eliminated by antagonizing e.g. receptors for bitter, acrid, astringent or sour taste, wherefore the antagonists can be identified by screening assays using the taste cells of the present invention.

Figures 1, 2:
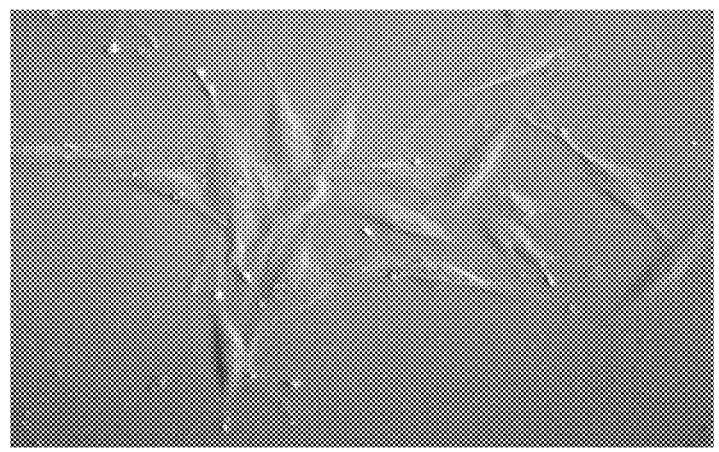

The figures show:

FIG. 1: Microscopic image of BR-HTC8 cells.

FIG. 2: Quantitative detection hTERT mRNA and large T antigen mRNA in the obtained cell lines BR-HTC18 and BR-HTC28 by quantitative RT-PCR. Briefly, the protocol comprised a) Isolation of total RNA from the cells, b) Reverse Transcription of 1 µg total RNA using a mixture of random hexamer and oligo-dT oligonucleotide primer c) Gene expression analysis of hTERT and large T genes by qRT-PCR using Light Cycler 480 II (Roche), SYBR I detection and the cyclophilin A gene (PPIA) as control. RT-PCR analysis revealed that the hTERT encoding gene is strongly expressed in BR-HTC18 and that hTERT and large T are expressed in BR-HTC28. CP values indicate the PCR cycle, at which a given PCR product is significantly amplified compared to the control without template.

FIG. 3: A Map of pLV-Ubic-TAS2R38-puro. B Quantitative detection TAS2R38 mRNA in the obtained cell line BR-HTC38 by qRT-PCR. C Measurement of functional consequences of TAS2R38 expression on responsiveness of BR-HTC38 cells to taste molecules in comparison to the parental BR-HTC8 cell line by Fluo-4 fluorescent calcium imaging assays. Briefly, the protocol comprised a) Isolation of total RNA from the cells, b) Reverse Transcription of 1 µg total RNA using a mixture of random hexamer and oligo-dT oligonucleotide primer c) Gene expression analysis of TAS2R38 by qRT-PCR (forward primer: CTGCTGTTCCT-GAGTGCTATCC (SEQ ID NO:277), reverse primer CAGAGGTTGGCTTGGTTTGC (SEQ ID NO:278)) using Light Cycler 480 II (Roche), SYBR I detection and the topoisomerase I gene (TOP1) (forward primer: CCAGACG-GAAGCTCGGAAAC (SEQ ID NO:279), reverse primer GTCCAGGAGGCTCTATCTTGAA (SEQ ID NO:280)) as control. CP values indicate the PCR cycle, at which a given PCR product is significantly amplified compared to the control without template. RT-PCR analysis revealed that the TASR38 encoding gene is strongly expressed in BR-HTC38.

Response of human taste cells to taste molecules leads to an increase in intracellular calcium, which was measured by the Fluo-4 fluorescent calcium imaging assay. Briefly, human taste cell lines BR-HTC8 and BR-HTC-38 were seeded in 96-well plates and stained with Fluo4-AM. Changes in $Ca^{2+}$-dependent Fluo-4 fluorescence were recorded on a Molecular Devices fluorescence microplate reader. Measurement was started by addition of increasing concentrations of the taste molecules. Addition of phenylthiocarbamide (PTC), saccharin, and salicin led to a dose-dependent increase of Fluo4-fluorescence in BR-HTC8 (dark grey). In BR-HTC38 cells, dose-dependent response to phenylthiocarbamide (PTC), saccharin, and salicin was enhanced (light grey). Calcium signals for each test molecule are depicted as relative fluorescence units (RFU). These data indicate that expression of the TAS2R38 gene in BR-HTC38 cells further improves authentic responsiveness of the BR-HTC8 human taste cells to taste stimuli.

Figure 4:
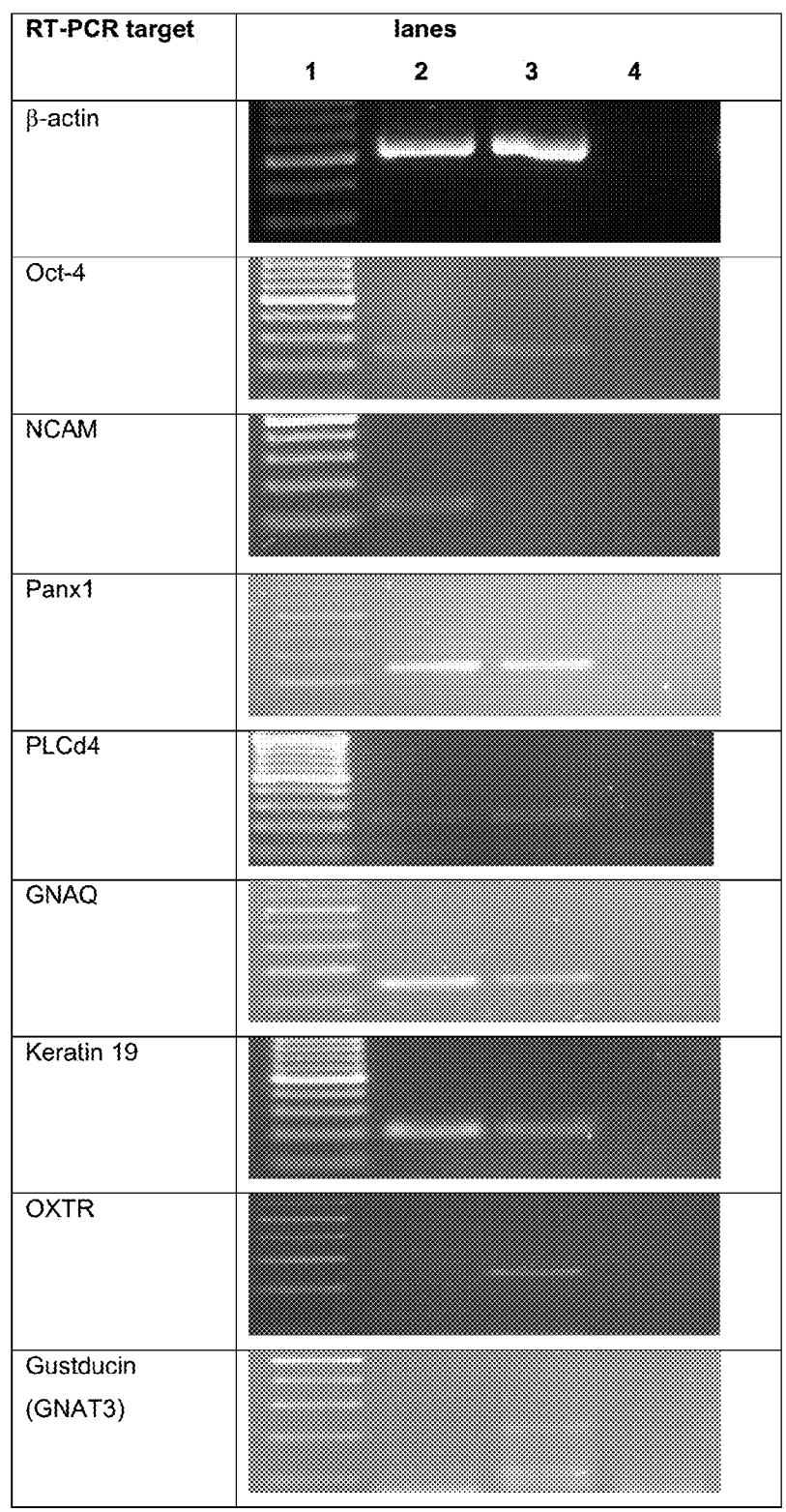
Figure 4:
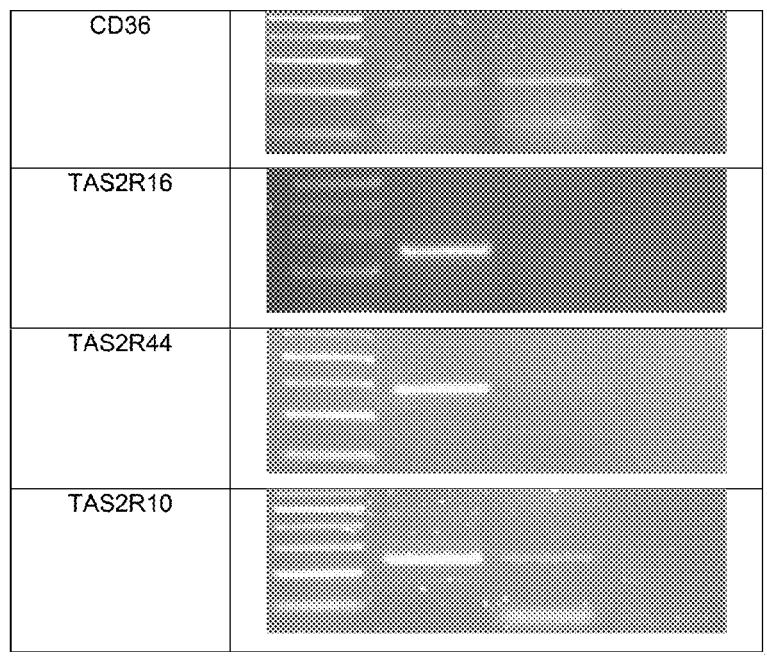

FIG. 4. Gene expression analysis by RT-PCR.

Expression of taste cell-specific genes encoding gustatory receptors, ion channels, signalling components as well as receptors for hormones implicated with satiety modulation and other factors relevant for taste cell identity as shown in Table 1 was determined by RT-PCR in human taste cells including BR-HTC8.

Total RNA was isolated from taste cells and reverse transcribed. As a negative control to check for genomic DNA contamination, RNA samples were treated in parallel in the presence of reverse transcriptase (RT+) and in the absence of reverse transcriptase (RT−). The cDNAs as well as the control samples were then analysed by PCR using gene-specific primer pairs as shown in Table 1.

Figure 5:
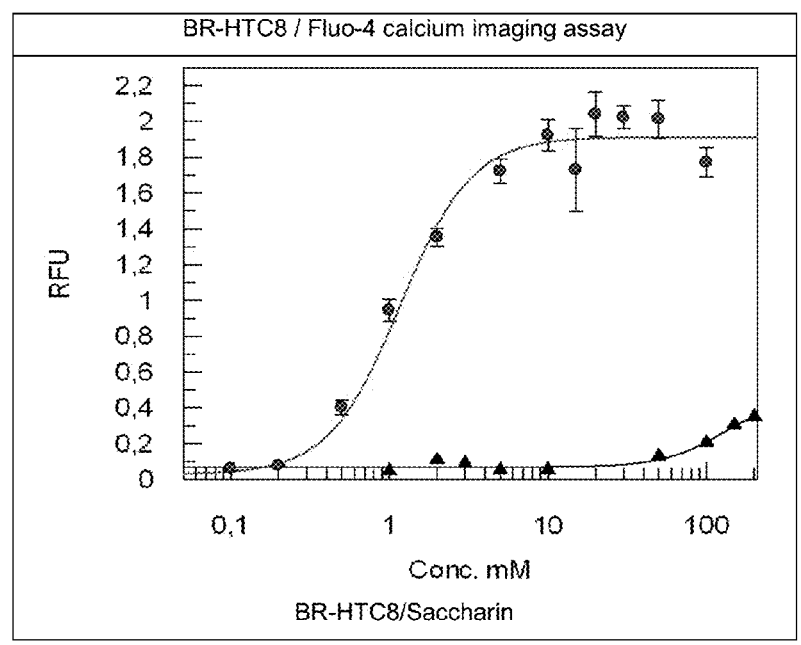
Figure 5:
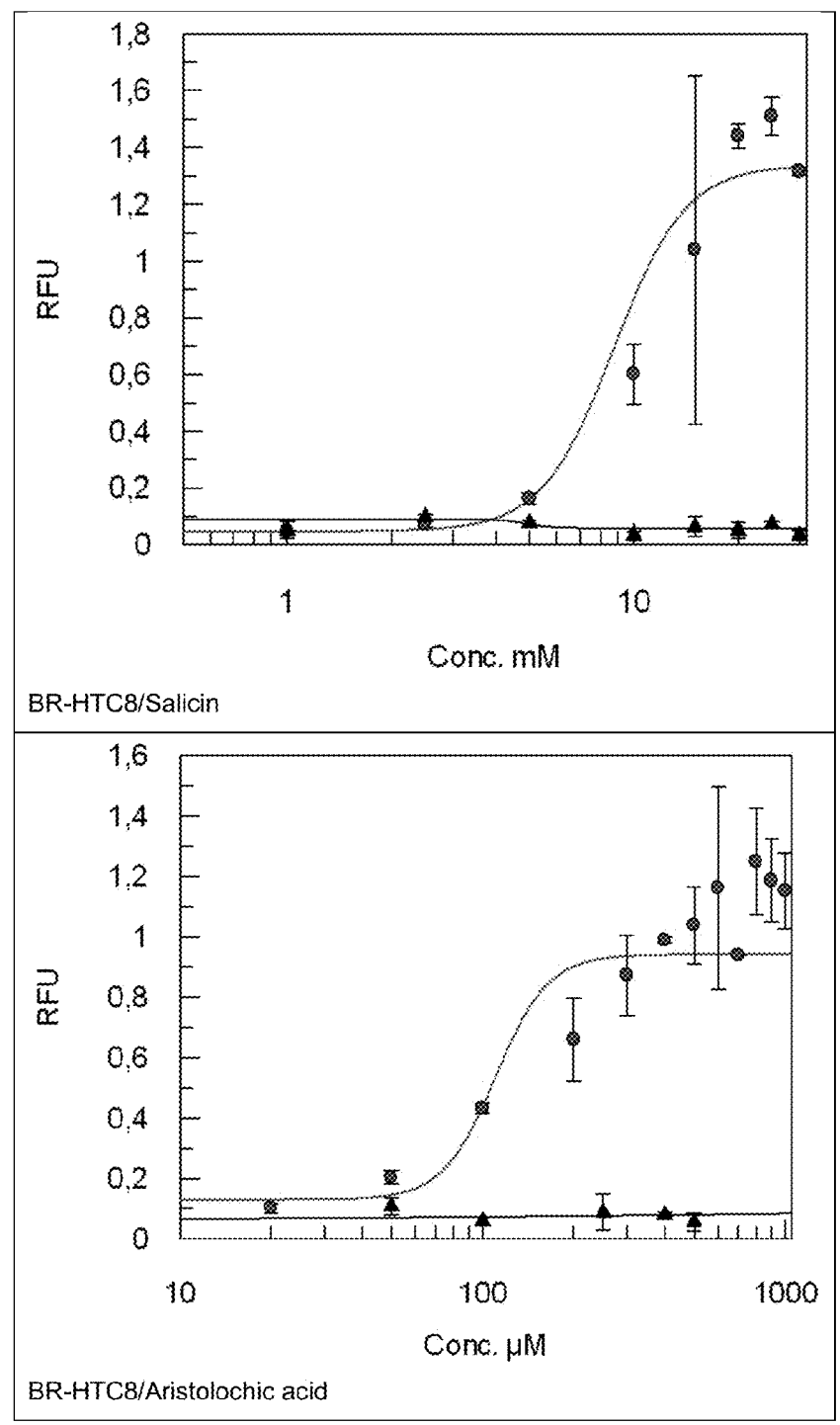
Figure 5:
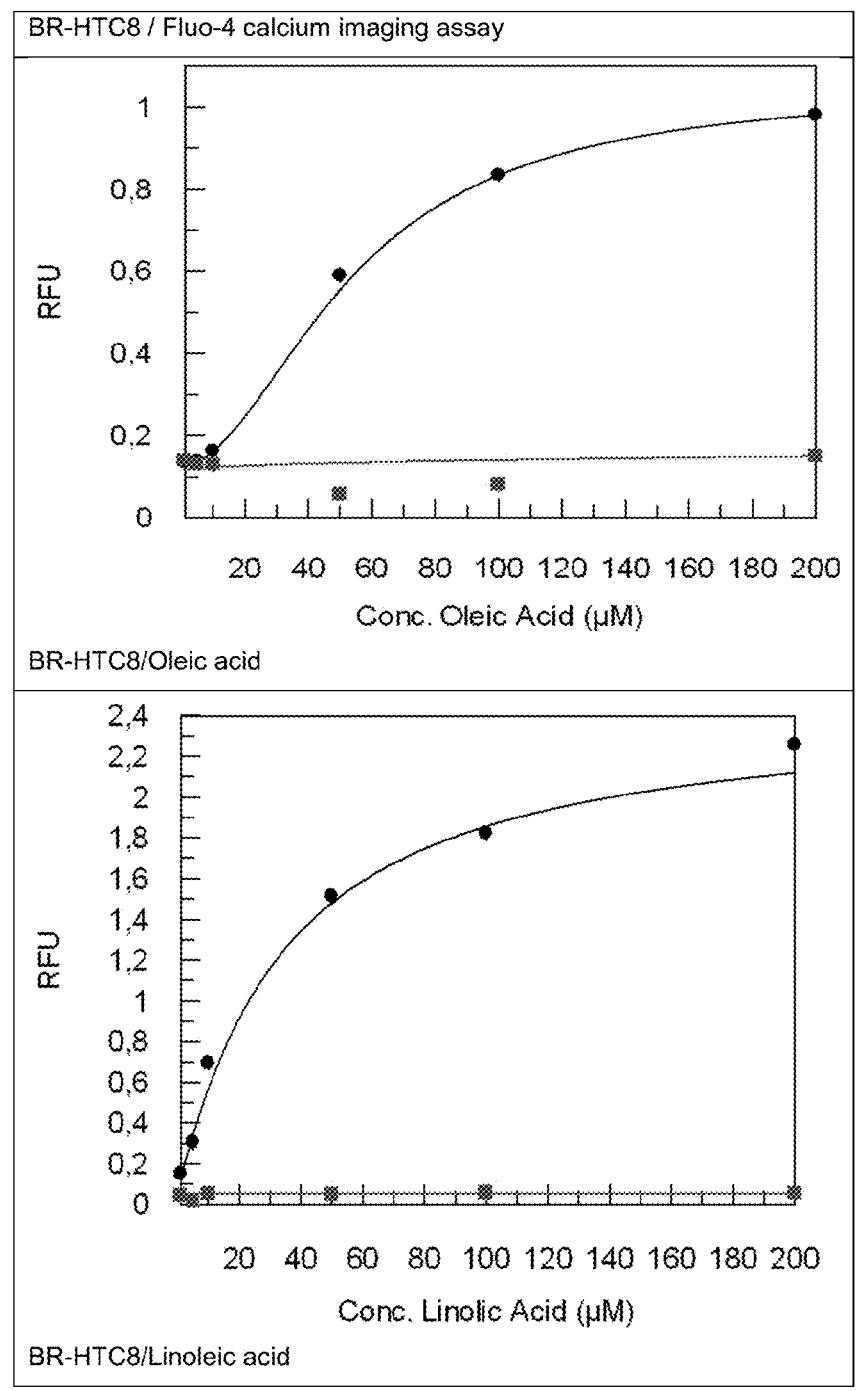
Figure 5:
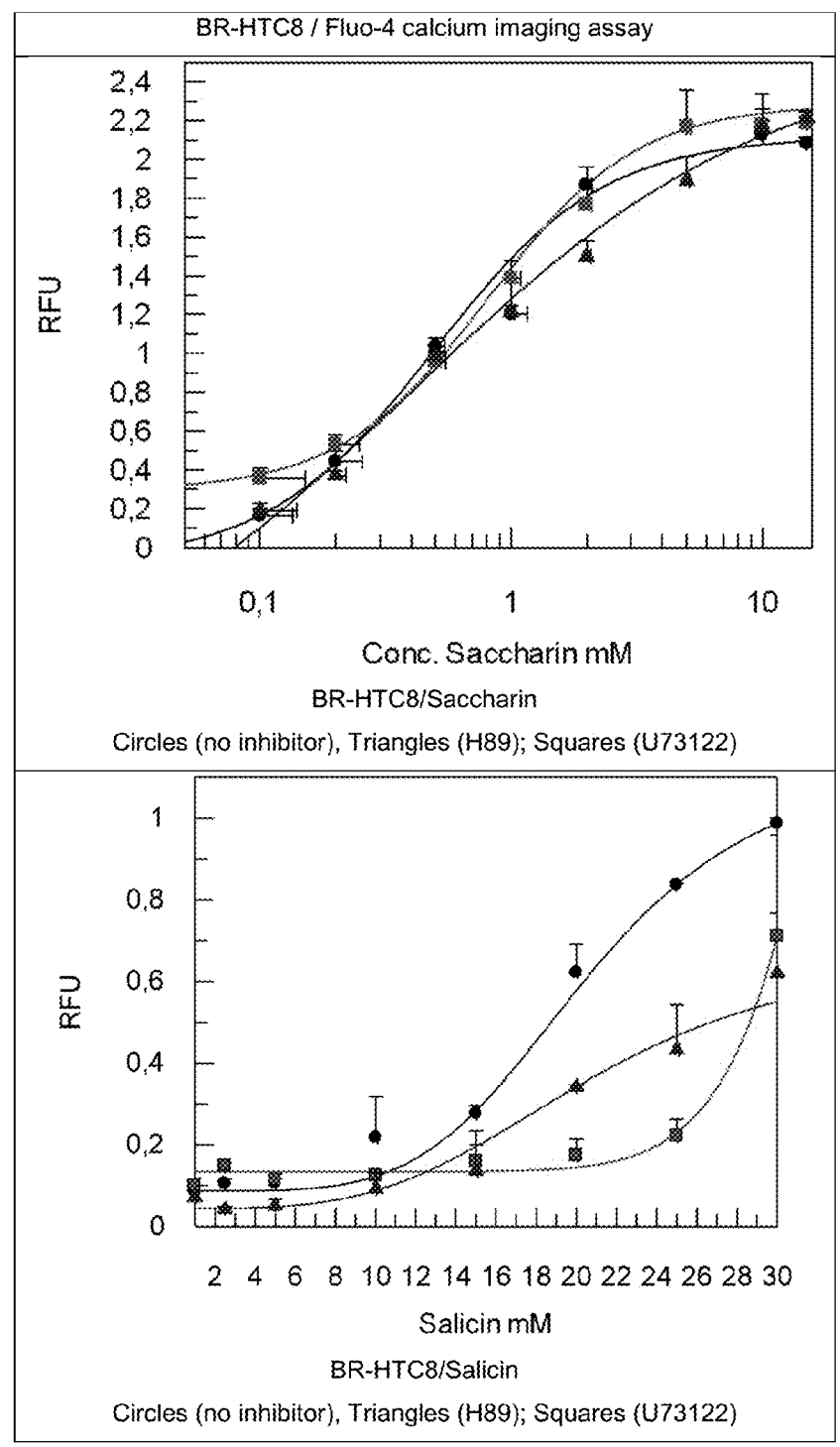
Figure 5:
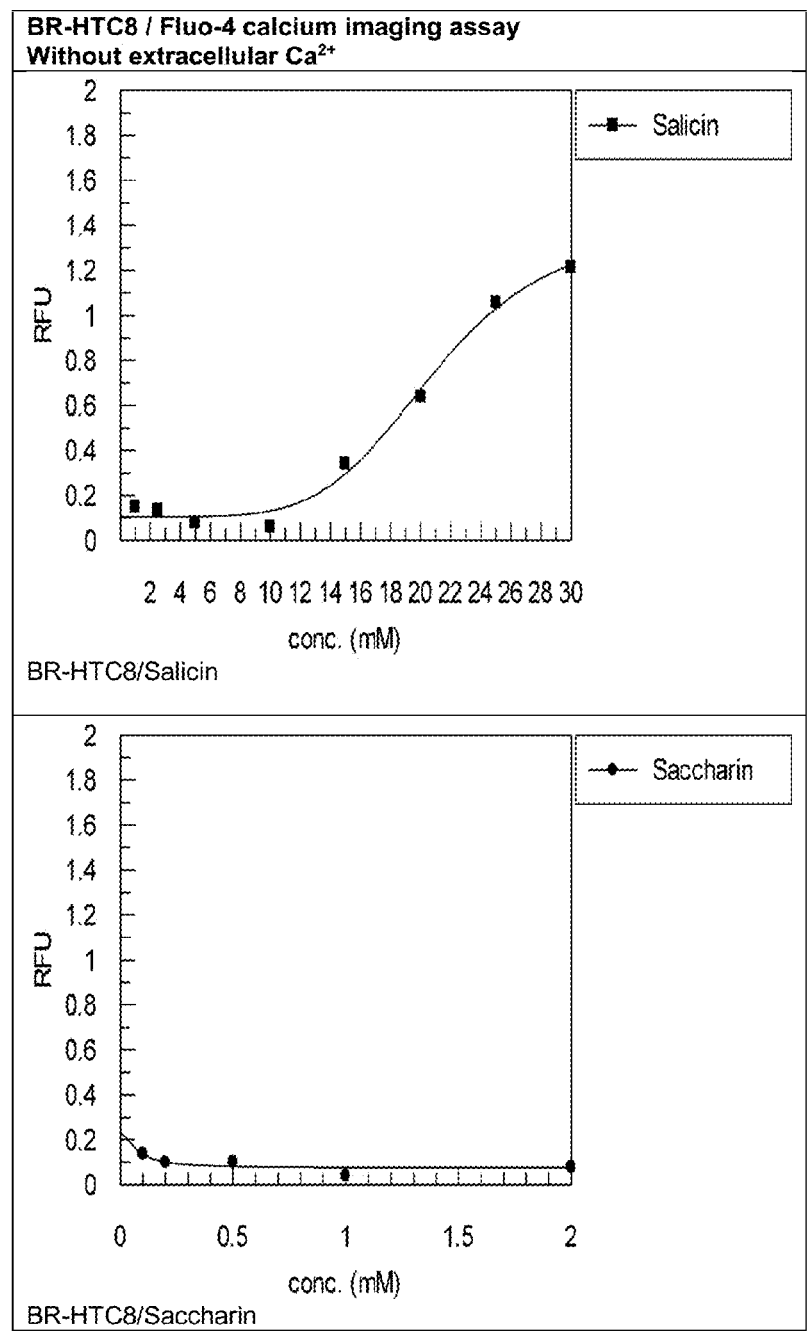
Figure 5:
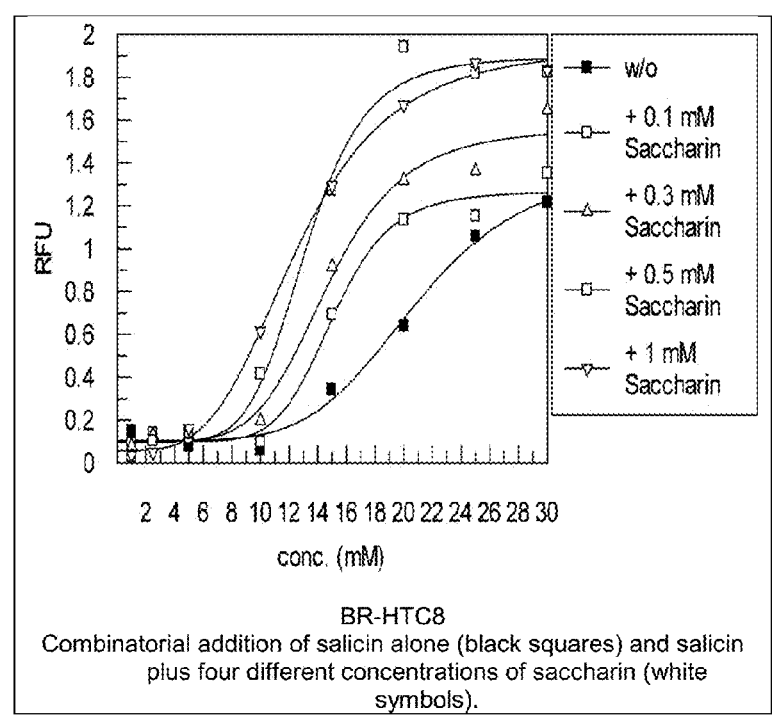

PCR products were separated on 2% agarose gels and stained with ethidium bromide. Analysis of selected target genes and representative agarose gels are shown. A complete list of results is shown in Table 1. Lane 1: DNA standard; Lane 2: control template; Lane 3: cDNA BR-HTC8; Lane 4: BR-HTC8, RT-control;

FIG. 5. Measuring human taste cell response to taste molecules by Fluo-4 fluorescent calcium imaging assay.

A Response of human taste cells to taste molecules leads to an increase in intracellular calcium, which was measured by the Fluo-4 fluorescent calcium imaging assay. Briefly, human taste cells were seeded in 96-well plates and stained with Fluo4-AM. Non-taste cells including HEK293 cells, Cal33 cells, and non-lingual, proliferating primary cells isolated from the oral cavity served as a control. Changes in $Ca^{2+}$-dependent Fluo-4 fluorescence were recorded on a Molecular Devices fluorescence microplate reader. Measurement was started by addition of increasing concentrations of the taste molecules. Addition of salicin, saccharin, and aristolochic acid, oleic acid, and linoleic acid led to a dose-dependent increase of Fluo4-fluorescence in BR-HTC8 (circles) and not in control cells (triangles, squares). Calcium signals for each test molecule are depicted as relative fluorescence units (RFU).

B Stimulation of human taste cells with salicin or saccharin alone (circles) and in the presence of 5 µM U73122 (rectangles), a known inhibitor of phospholipase C2 (Phospolipase Cβ2 (PLCβ2) revealed, that calcium signalling of human taste cells is inhibited by U73122 when BR-HTC8 cells are stimulated with salicin, however, the response to saccharin is not reduced. Stimulation of human taste cells with salicin and saccharin in the presence of 0.5 µM H89 (triangles), a known inhibitor of protein kinase A (PKA) revealed that calcium signalling in BR-HTC8 is slightly inhibited by H89 when cells are stimulated with salicin, however, the response to saccharin is not reduced. These date indicate that human taste cells employ distinct signalling pathways when responding to these stimuli, which is consistent with previously published data (Hacker, K. et al., Evidence for two populations of bitter responsive taste cells in mice. Journal of Neurophysiology, 2008, 99(3): 1503-1514; Ogura, T. et al. Taste receptor cell responses to the bitter stimulus denatonium involve Ca2+ influx via store-operated channels. Journal of Neurophysiology, 2002, 87(6): 3152-3155).

C Stimulation of BR-HTC8 cells with salicin elicits an increase of intracellular calcium from internal calcium stores in the absence of extracellular $Ca^{2+}$. In contrast, addition of other bitter taste stimuli for instance saccharin cannot trigger a $Ca^{2+}$ response in the absence of extracellular $Ca^{2+}$ These results further suggest that gustatory responses to bitter stimuli are not uniform in human taste cells and that bitter taste stimuli may trigger distinct signaling pathways. To test, whether these distinct signaling pathways interact we stimulated HTC-8 cells with increasing concentrations of salicin together with four fixed concentrations of saccharin acid in the absence of extracellular calcium. Even though saccharin alone elicited no response at the concentrations used in the combinatorial test, the increase of intracellular calcium in response to salicin was strongly enhanced. These results suggest that cross-talk between bitter taste receptors and/or signaling pathways may occur in human taste cells.

Figure 6:
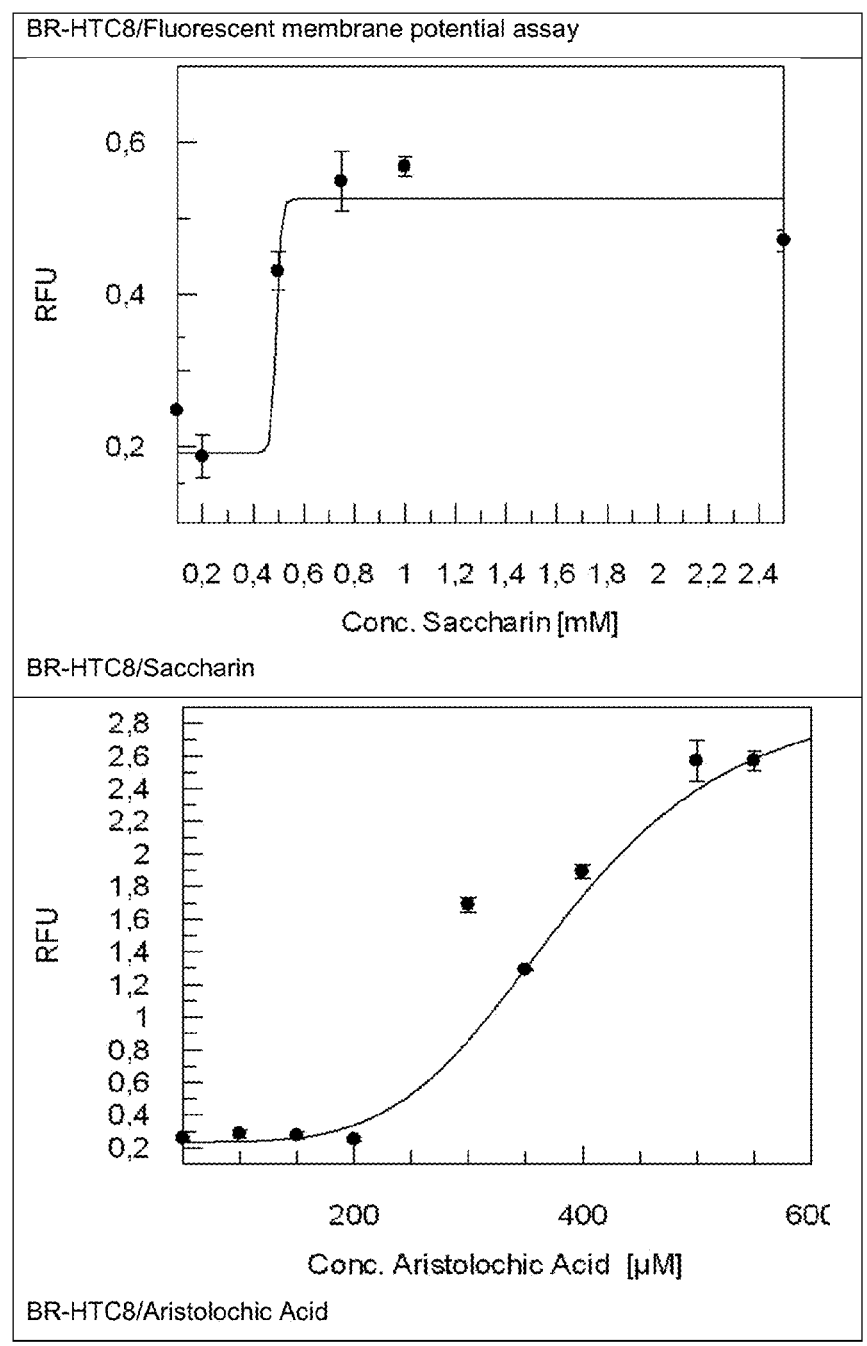
Figure 6:
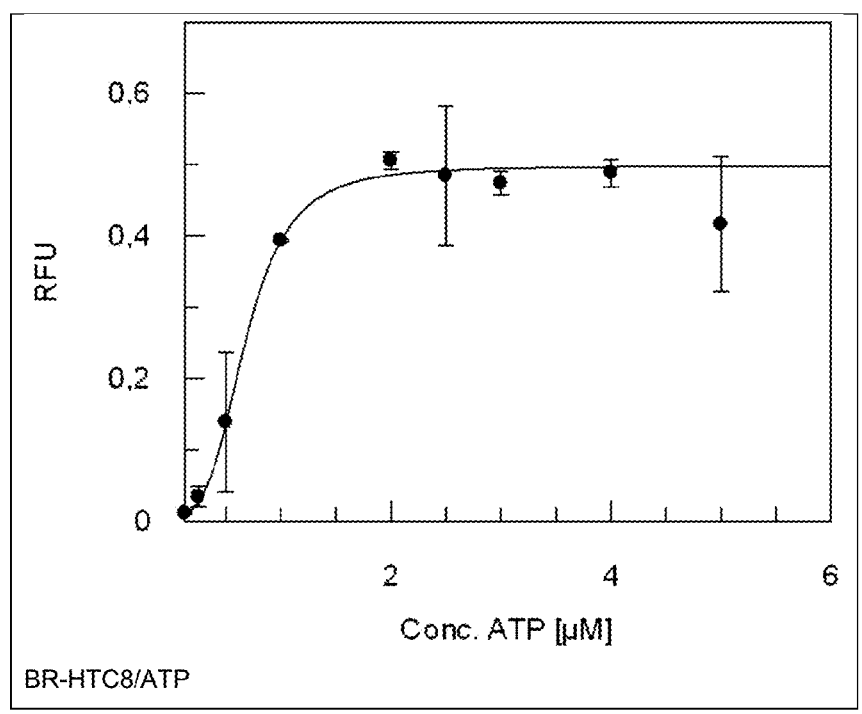

FIG. 6: Measuring human taste cell response to taste molecules and signalling molecules by FLIPR fluorescent membrane potential imaging assay.

Response of human taste cells BR-HTC8 to taste molecules and signalling molecules including ATP lead to a decrease in cellular membrane potential, which was measured by the FLIPR fluorescent membrane potential imaging assay. Human taste cells were seeded in 96-well plates and stained with FLIPR FMP dye. Non-taste cells including HEK293 cells and non-lingual, proliferating primary cells isolated from the oral cavity served as a control. Changes in cellular membrane potential-dependent fluorescence were recorded on a Molecular Devices fluorescence microplate reader. Measurement was started by addition of increasing concentrations of the test molecules. Addition of the taste molecules saccharin and aristolochic acid and of the signalling molecule ATP led to a dose-dependent decrease in cellular membrane potential (indicated by the recorded increase of fluorescence) in BR-HTC8 cells. Changes in membrane potential for each test molecule are depicted as Relative Fluorescence Units (RFU). Addition of salicin did not elicit significant changes in cellular membrane potential (data not shown). Data were obtained from several independent experiments and performed in triplicates. These experiments revealed that human taste cells respond to taste molecules including saccharin and aristolochic acid with a decrease in cellular membrane potential and an increase in intracellular calcium as shown in example 5, FIG. 5A and table 2. However, human taste cells respond to other taste molecules including salicin only with an increase in intracellular calcium and not with a significant change in cellular membrane potential as shown in table 2. Other taste molecules including acesulfame K induce a decrease in cellular membrane potential in said taste cells and do not trigger an increase in intracellular calcium as shown in table 2. These results further indicate that said human taste cells can respond to taste molecules with distinct or overlapping signalling pathways.

Stimulation of human taste cells with ATP triggers a decrease in cellular membrane potential as well as an increase in intracellular calcium, which has been shown by Fluo-4 calcium imaging assay as shown in table 2. These findings further indicate that human taste cell lines described in this study (BR-HTC8) share components for the release of transmitter molecules including PANX1 with taste cells derived from other model organisms including rodents and also share the responsiveness to ATP.

Figure 7:
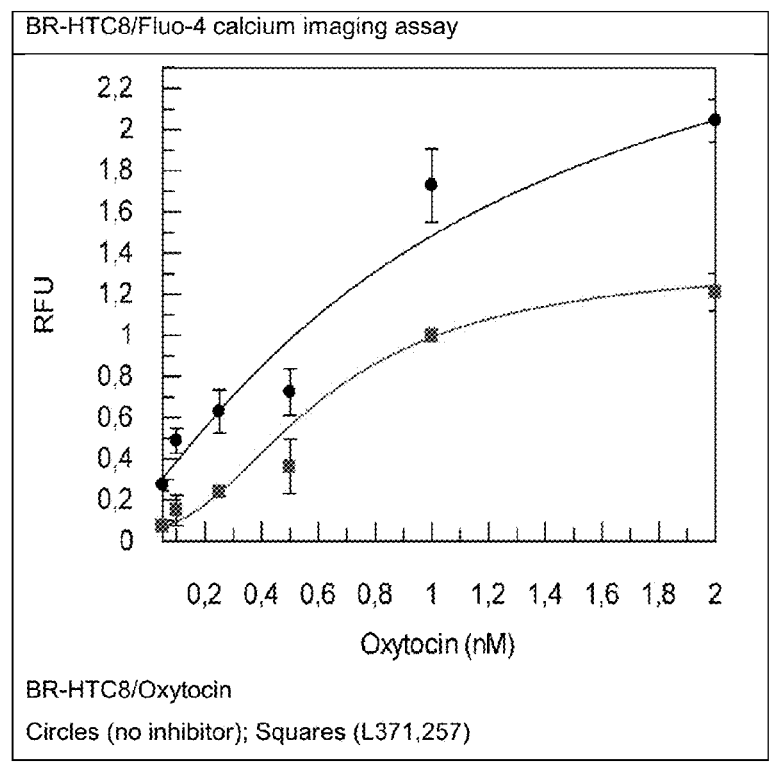

FIG. 7 Measuring human taste cell response to oxytocin by Fluo-4 fluorescent calcium imaging assay.

Stimulation of human taste cells with oxytocin was analysed by the Fluo-4 fluorescent calcium imaging assay performed and leads to an increase in intracellular calcium (circles). Briefly, the human taste cells were seeded in 96-well plates and stained with 2 µM of the calcium-sensitive fluorescence dye Fluo-4. Non-taste cells including HEK293 cells and non-lingual, proliferating primary cells isolated from the oral cavity served as a control and were treated equally throughout the procedure. Changes in $Ca^{2+}$-dependent Fluo-4 fluorescence were recorded on a Molecular Devices Fluorescence microplate reader. Measurement was started by addition of increasing concentrations of oxytocin in KH-buffer to the cells. KH-buffer served as negative control and KH-buffer containing 1 µM ionomycin served as a positive control. Addition of oxytocin led to a dose-dependent increase of Fluo4-fluorescence (circles). Calcium signals for each test molecule are depicted as Relative Fluorescence Units (RFU), which means that calcium mobilization in response to taste molecules was calculated dF/F0, with dF is (peak fluorescence F1−baseline fluorescence F0). Data were obtained from several independent experiments and performed in triplicates.

Stimulation of human taste cells with oxytocin in the presence of 40 nM L371,257, an oxytocin antagonist, revealed that calcium signalling of human taste cell is inhibited by L371,257 (rectangles).

Figure 8:
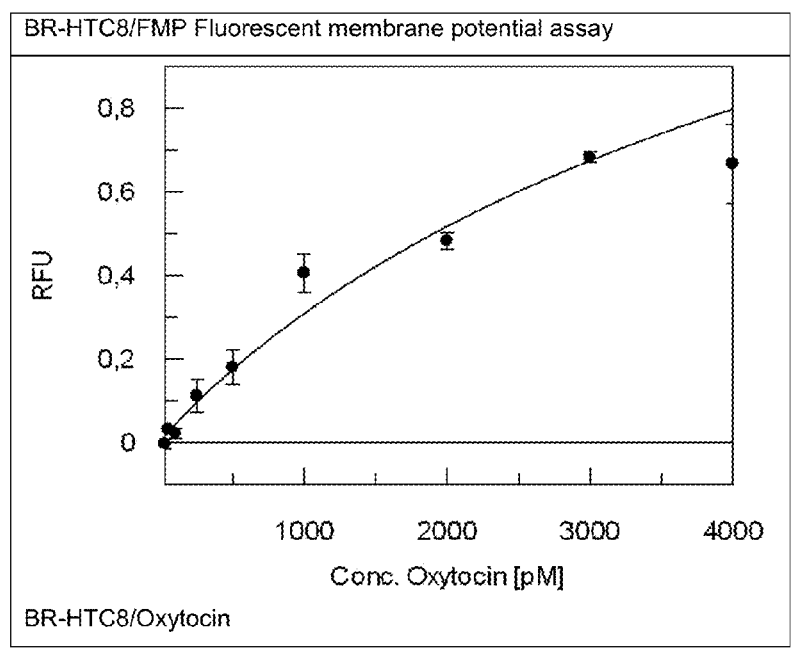

FIG. 8 Measuring human taste cell response to hormones by FLIPR fluorescent membrane potential imaging assay.

In order to test whether stimulation of human taste cells (BR-HTC8) with oxytocin leads to changes in cellular membrane potential, the FLIPR fluorescent membrane potential assay was performed. Briefly, said human taste cells were seeded in 96-well plates and stained with the FLIPR FMP dye. Non-taste cells including HEK293 cells and non-lingual, proliferating primary cells isolated from the oral cavity served as a control and were treated equally throughout the procedure. Changes in membrane potential were recorded on a Molecular Devices Fluorescence microplate reader. Measurement was started by addition of increasing concentrations of oxytocin in KH-buffer to the cells. KH-buffer served as negative control and KH-buffer containing 4 µM FCCP (Sigma, C2920) served as a positive control. Addition of oxytocin led to a dose-dependent decrease of membrane potential (circles), which corresponds to an increase in FLIPR FMP dye fluorescence. Signals for each test molecule are depicted as Relative Fluorescence Units (RFU), which means that a decrease in cellular membrane potential in response to taste molecules was calculated dF/F0, with dF is (peak fluorescence F1−baseline fluorescence F0). Data were obtained from several independent experiments and performed in triplicates. The experiments revealed that human taste cells including BR-HTC8 respond to hormones including oxytocin with a decrease in cellular membrane potential as well as with an increase in intracellular calcium as shown in example 7 and FIG. 7. These results further indicate that said human taste cells can respond to hormones with distinct or overlapping signalling pathways.

EXAMPLES

Example 1

Cultivation of Continuous Human Taste Cell Lines and Re-Cultivation after Thawing Cryo-Conserved Cells Stably proliferating human taste cells described in this invention were preserved using 500,000 to 2,000,000 cells per vial in Cryo-SFM medium (e.g. Promocell, C-29912) and stored in liquid nitrogen. In order to start over cultivation using preserved human taste cells a thawing-and-cultivation procedure was employed comprising the following steps:

1. Remove vial from liquid nitrogen storage container and thaw quickly by submerging and gentle agitation in a water bath pre-warmed to 37° C.
2. Immediately after thawing process has completed transfer the cells into 10 ml of fresh HTC medium described below and mix by inverting the closed vial several times
3. Sediment cells of step (2), by centrifugation at 1500×g for 10 min and discard supernatant.
4. Resuspend cells in 10 ml fresh HTC medium and transfer the cells to a suitable tissue culture dish and start cultivation at 37° C. according to the procedures known to a person skilled in the art.
5. Change medium when appropriate according to the procedures known to a person skilled in the art.
6. When cells have formed an almost confluent monolayer, detach the cells from the bottom of the culture dish using TrypLE (e.g. Gibco, 12563) protease treatment.
7. Dilute cells 1:2, preferably 1:3, more preferably 1:4 with HTC medium and cultivate a suitable tissue culture dish.
8. Expand stably proliferating human cells. Monitor cells by microscopy with regard to shape and morphology. A representative microscopy image of the cells described in this invention is shown in FIG. 1.
9. Cryo-preservation of proliferating taste cell can be done at any time using Cryo-SFM medium (e.g. Promocell, C-29912) as described above.
10. Establish continuous proliferation properties of the thawed and re-cultivated cells described in this invention. This method comprises the following steps: 1) Cultivate cells in HTC medium. HTC medium (500 mL) consists of Basal Iscove Medium (400 mL) (e.g. F0465, Biochrom), MCDB 153 Basal Medium (100 mL) (e.g. F8105, Biochrom AG) containing 10% FCS Gold (e.g. A15-151, PAA Laboratories GmbH), 4 mM L-glutamine (e.g. M11-004, PAA Laboratories GmbH), 1% antibiotic/antimycotic (e.g. A5955, Sigma-Aldrich GmbH), 2.5 µg/mL gentamycin (e.g. A2712, Biochrom) and 10 µg/mL Insulin (e.g. 19278, Sigma-Aldrich GmbH). Cultivate cells at 37° C. until cells have formed a confluent monolayer covering the entire surface of the culture dish, which takes 2-4 days; 2) Detach cells using TrypLE (e.g. Gibco, 12563) protease treatment; 3) Dilute cells 1:2, preferably 1:3, more preferably 1:4 with HTC medium and cultivate in culture dish with identical dimensions as the previous culture dish or larger and cultivate as described in step (1); 4) Repeat step (1) through step (3) 20 times, preferably 30 times, more preferably 40 times.

Example 2

Establishment of Further Immortalized Human Taste Cell Lines

Thawing and cultivation of the human taste cells described in the invention as outlined in Example 1 resulted in stably proliferating human taste cells. The stability and proliferative properties of these cells can be further enforced with additional immortalization gene cassettes that are transduced using retroviral transduction and stable integration of the gene cassettes into the recipient genome.

We therefore used lentiviruses including pCDH-CMV-LTtsA58-G418 and LV-CMV-hTERT-EF1-Puro, which carry the SV40 temperature-sensitive large T tsA58 gene and the human hTERT gene under the control of the CMV promoter, respectively.

Continuously proliferating human taste cell populations including BR-HTC8 were used to stably introduce additional exogenous genes, which have been previously established to delay or offset senescence, including hTERT and SV40 temperature-sensitive large T tsA58.

Cultivation of cells was done in IMEM medium (e.g. Biochrom, F 0465) containing +10% FCS (e.g. PAA, A15-101), 20% MCDB-153 (e.g. Biochrom, F 8115), 2 mM L-glutamine (e.g. PAA, M11-004), 10 ng/ml bovine insulin (e.g. Biochrom, K 3510), 1% PenStrep (e.g. PAA, P11-010), 2.5 µg/ml gentamycin (e.g. Biochrom, A 2712), 0.5 µg/ml amphotericin (e.g. Biochrom, 2612) on cultures dished pre-coated with aqueous 0.02% Collagen R solution (=Collagen I) (e.g. Serva, H47254).

Infection of cells with pCDH-CMV-LTtsA58-G418 comprised the following steps:

1) Seeding of 10.000 cells per 6-well, incubate until cells are adherent
2) Transduction of cells in presence of 8 µg/ml Polybrene (e.g. Santa Cruz, sc-134220) with lentiviruses at a multiplicity of infection (moi) of 30 and cultivation at 33° C. using standard cell cultivation techniques. Untreated cells were cultivated equally and subsequently used as negative control.
3) Selection of stably transduced cells 72 h after transduction by supplementing medium with 0.75 mg/ml G418 (e.g PAA, P11-012).
4) Cultivation of cells for 10-21 days under G-418 selection until proliferating cells are evident and untreated control cells of step (2) are all dead.
5) Maintenance of immortalized in medium containing 0.375 mg/ml G418 on dishes pre-coated with collagen at 33° C. Inactivation of LTtsA58 will occur by shifting the incubation temperature to 37-38° C. Cells can be stably maintained in G418-free medium for up to 2 weeks.
6) Cryo-preservation of G418 resistant, proliferating cell cultures using Cryo-SFM medium (e.g. Promocell, C-29912). Proliferating cell populations with no apparent heterogeneity with regard to morphology, growth and proliferation properties were obtained.
7) Establish continuous proliferation properties of obtained cell lines by long term cultivation of cells as monolayer in cell culture dishes as described above in example 1. G418 resistant, proliferating cell cultures obtained in step (6) were further transduced with LV-CMV-hTERT-EF1-Puro (see protocol below). Selection was performed in the indicated medium containing G418 and puromycin. Obtained cell lines included BR-HTC28. Quantitative detection hTERT and large T mRNA in the obtained cell lines using qRT-PCR was performed using a protocol described below and revealed that hTERT as well as large T tsA58 are strongly expressed as shown in FIG. 2.

Infection of cells with LV-CMV-hTERT-EF1-Puro comprised the following steps:
1) Seeding of 10.000 cells per 6-well including BR-HTC8 as well as cells obtained in step (6) described above, which have received large T tsA58, incubate at 37° C. until cells are adherent
2) Transduction of cells in presence of 8 μg/ml polybrene (e.g. Santa Cruz, sc-134220) with lentiviruses at a multiplicity of infection (moi) of 20 and cultivation at 37° C. using standard cell cultivation techniques. Untreated cells were cultivated equally and subsequently used as negative control.
3) Selection of stably transduced cells 24 h after transduction by supplementing medium with 0.5 μg/ml puromycin. Continue selection for three days.
4) Reduce puromycin concentration to 0.25 μg/ml and continue cultivation of cells for 20 days until proliferating cells are evident and untreated control cells of step (2) are all dead.
5) Cryo-preservation of puromycin-resistant, proliferating cell cultures using Cryo-SFM medium (e.g. Promocell, C-29912). Proliferating cell populations with no apparent heterogeneity with regard to morphology, growth and proliferation properties were obtained including BR-HTC18.
6) Maintenance of immortalized cell lines in medium containing 0.25 μg/ml.
7) Quantitative detection hTERT and large T mRNA in the obtained cell lines using qRT-PCR was performed using a protocol comprising the following steps using standard molecular biology techniques known to a person skilled in the art: a) Isolation of total RNA from the cells, b) Reverse Transcription of 1 μg total RNA using a mixture of random hexamer and oligo-dT oligonucleotide primer ProtoScript M-MuLV First Strand cDNA Synthesis Kit (e.g. NEB, E6300L), c) Determine relative gene expression of hTERT and large T genes by qRT-PCR using oligonucleotide primers (hTERT forward primer: AACCTTCCTCAGCTATGCCC (SEQ ID NO:281), reverse primer: GTTTGCGACGCATGTTC-CTC (SEQ ID NO:282); large T forward primer: CACT-GCAGGCCAGATTTGTA (SEQ ID NO:283), reverse primer: CAAAGCAATGCCACTTTGAA (SEQ ID NO:284)) and using a Light Cycler 480 II (Roche), SYBR I detection and the cyclophilin A gene (PPIA) (forward primer: CAGACAAGGTCCCAAAGACAG (SEQ ID NO:285), reverse primer: TTGCCATCCAAC-CACTCAGTC (SEQ ID NO:286)) as control (FIG. 2). RT-PCR analysis revealed that the hTERT encoding gene is strongly expressed in BR-HTC18 and that the hTERT gene as well as the gene encoding large T tsA58 are strongly expressed in BR-HTC28 as shown in FIG. 2.
8) Establish continuous proliferation properties of cell lines including BR-HTC18 by long term cultivation of cells as monolayer in cell culture dishes as described in Example 1 above.

Example 3

Establishment of Genetically Engineered Human Taste Cell Lines

Genetic manipulation of continuously proliferating taste cell populations (BR-HTC8) was successfully established for lentiviral transduction of exogenous genes encoding factors, which are involved in delaying or offsetting senescence as described in example 2. We therefore set out to introduce genes encoding taste receptors, ion channels, and signalling transduction components known for taste molecule stimulus reception and taste signal transduction and modulation in gustatory processes. The goal was to further enhance and tune the genuine properties and performance of human taste cells.

Cloning of the TAS2R38 gene coding sequence to obtain pLV-Ubic-hTASR38-IRES-Puro as shown in FIG. 3A: A 1030 bp fragment comprising the TAS2R38 coding sequence was cloned EcoRI-XbaI into the lentiviral plasmid pLV-Ubic-MCS-IRES-Puro, which places the TAS2R38 gene downstream of the ubiC gene promoter and upstream of an internal ribosomal entry site (IRES) and the puroR puromycin resistance gene. Transcription is directed by the ubiC gene Promoter will result in one mRNA transcription unit comprising TAS2R38-IRES-PuroR. Only if the full length mRNA is transcribed and the IRES is functional, then the PuroR resistance gene is translated and stably transduced cells resistant to puromycin will be obtained. Self-inactivating transduction particles were then produced by cotransfection of HEK293TN cells with pLV-Ubic-TAS2R38-IRES-Puro and lentiviral packaging plasmids using standard techniques in molecular cell biology known to a person skilled in the art. Viral genomic titers of LV-Ubic-TAS2R38-IRES-Puro were determined using LentiX qRT-PCR (Clontech, 631235).

Infection of cells with LV-Ubiqc-TAS2R38-IRES-Puro comprised the following steps:
1) Seeding of 10.000 BR-HTC8 cells per 6-well, incubate until cells are adherent
2) Transduction of cells in presence of 8 μg/ml Polybrene (e.g. Santa Cruz, sc-134220) with Lentiviruses at a multiplicity of infection (moi) of 5 and cultivation at 37° C. using standard cell cultivation techniques. Untreated cells were cultivated equally and subsequently used as non-transduced control.
3) Selection of stably transduced cells 72 h after transduction by supplementing medium with 1 μg/ml puromycin. Continue selection until cells of non-transduced control of step (2) are dead.
4) Reduce puromycin concentration to 0.5 μg/ml and continue cultivation of cells for 20 days or until proliferating cells are evident.
5) Cryo-preservation of puromycin-resistant, proliferating cell cultures using Cryo-SFM medium (e.g. Promocell, C-29912). Proliferating cell populations with no apparent heterogeneity with regard to morphology, growth and proliferation properties were obtained including BR-HTC38. Maintenance of stably transduced cell lines in medium containing 0.5 μg/ml puromycin.
6) Quantitative detection TAS2R38 mRNA in the obtained cell lines using qRT-PCR was performed using a protocol comprising the following steps using standard molecular biology techniques: a) Isolation of total RNA from the cells, b) Reverse Transcription of 1 μg total RNA using a mixture of random hexamer and oligo-dT oligonucleotide primer ProtoScript M-MuLV First Strand cDNA Synthesis Kit (e.g. NEB, E6300L), c) Determine relative gene expression of TAS2R38 by quantitative RT-PCR using oligonucleotide primers (ff primer: 5'-CTGCTGTTCCTGAGTGCTATCC-3' (SEQ ID NO:277), rev primer: 5'-CAGAGGTTGGCTTG-GTTTGC-3' (SEQ ID NO:278)) using a Light Cycler 480 II (Roche), SYBR I detection and the Topoisomerase 1 gene (TOP1) (ff primer: 5'-CCAGACG-GAAGCTCGGAAAC-3' (SEQ ID NO:279), rev primer: 5'-GTCCAGGAGGCTCTATCTTGAA-3' (SEQ ID NO:280)), as control. RT-PCR analysis revealed that the TASR38 encoding gene is strongly expressed in BR-HTC38 as shown in FIG. 3B.

In an additional step, analysis of the functional consequences of TAS2R38 expression on responsiveness to taste molecules in BR-HTC38 cells in comparison to the parental BR-HTC8 cell line was performed in Fluo-4 fluorescent calcium imaging assays as described below (Example 5). Human taste cell lines BR-HTC8 and BR-HTC-38 were seeded in 96-well plates and stained with Fluo4-AM. Changes in $Ca^{2+}$-dependent Fluo-4 fluorescence were recorded on a Molecular Devices fluorescence microplate reader. Measurement was started by addition of increasing concentrations of the taste molecules in KH-buffer to the cells. KH-buffer served as negative control and KH-buffer containing 1 µM ionomycin served as a positive control. Addition of phenylthiocarbamide (PTC), salicin and saccharin, which have been previously established as bitter taste molecules activating TAS2R38 (Bufe et al., The molecular basis of individual differences in phenylthiocarbamide and propylthiouracil bitterness perception. *Curr Biol* (2005) 15: 322-327), TAS2R16 (Bufe et al., The human TAS2R16 receptor mediates bitter taste in response to beta-glucopyranosides. *Nat Genet* (2002) 32: 397-401) and TAS2R43/TAS2R44 (Kuhn et al., Bitter taste receptors for saccharin and acesulfame K., *J Neurosci* (2004) 24: 10260-10265) led to a dose-dependent increase of Fluo4-fluorescence in BR-HTC8 as shown in FIG. 3C. In BR-HTC38 cells, dose-dependent response to phenylthiocarbamide (PTC), saccharin, and salicin was enhanced as shown in FIG. 3C. Calcium signals for each test molecule are depicted as Relative Fluorescence Units (RFU), which means that calcium mobilization in response to taste molecules was calculated dF/F0, with dF is (peak fluorescence F1–baseline fluorescence F0). Peak fluorescence intensity occurred 20-30 sec after addition of the taste molecules. Data were obtained from several independent experiments and performed in triplicates. These data indicate that expression of the TAS2R38 gene in BR-HTC38 cells further improves authentic responsiveness of BR-HTC38 human taste cells to bitter taste stimuli in comparison to the BR-HTC8 parental cells.

Example 4

Testing Taste Cell Gene Expression by RT-PCR

Expression of taste cell-specific genes encoding gustatory receptors, ion channels, signalling components as well as receptors for hormones implicated with satiety modulation and other factors relevant for taste cell identity as shown in Table 1 was determined by RT-PCR in human taste cells described in this innovation.

Reverse Transcription-Polymerase Chain Reaction (RT-PCR) analysis was performed with human taste cells cultivated as described in Example 1. RT-PCR analysis is also performed with further immortalized and cultivated human taste cells as described in Example 2 and with genetically engineered human taste cells as described in Example 3.

Taste cell genes encoding the following proteins said to be functionally relevant in taste cells are analysed by RT-PCR: TRPV1, SCNN1A, SCNN1B, SCNN1G, SCNN1D, TRPML3, gustducin (GNAT3), TRPM5, Oct-4, T1R1, T1R2, T1R3, TAS2R38, TAS2R44, TAS2R1, TAS2R2, TAS2R3, TAS2R4, TAS2R5, TAS2R7, TAS2R8, TAS2R9, TAS2R10, TAS2R13, TAS2R14, TAS2R16, TAS2R39, TAS2R40, TAS2R41, TAS2R42, TAS2R43, TAS2R45, TAS2R46, TAS2R47, TAS2R48, TAS2R49, TAS2R50, TAS2R60, PLCb2, keratin 5, keratin 8, NCAM, IP3R3, keratin 19, Sox 2, TP63, SHH, Ptc 1, Glast, NTPD, Trf2, Trf3, Tbp, mGlut1, mGlut4, β-actin, PKD2L1, keratin 14, Mash 1, SNAP 25, SNAP 25, PC 1/3, ESPN, GOAT, Oct-11, PLCD4, CXCL14, ADRA1A, ADRB1, ADORA2B, SYN2, SYT1, NRCAM, OXTR, GPR120, GPR40, CD36, KCNC2, KCNQ1, KCNH2, GNG13, GNB3, GNA13, GNA11, GNA14, GNA12, GNB1, GNAL, GNA15, GNAQ, PANX1, ROMK, LEPR, P2RY12, P2RX7, KCNA1, KCNA2, KCNA3, KCNA5, KCNA6, KCNB1, KCNB2, KCNC1, CREB1, PDE1A, SCN2A, SCN3A, SCN9A, ACCN1, ACCN2, ACCN3. β-actin (a housekeeping gene) is used as a positive control. A complete list of target genes and oligonucleotide primers used is shown in Table 1 below.

Total RNA was isolated from taste cells cultivated for 20 generations, 25 generations, and 30 generations, reverse transcribed and amplified by PCR. Amplification product of the expected size is detected for a large number of taste cell genes, which been previously described for mammalian model organisms. Currently, there is no appropriate human taste cell line available, which may serve as a reference.

The protocol Used for RNA-Isolation, Reverse Transcription and Amplification by PCR comprised the following steps:
1) Extraction of total RNA using Nucleospin RNA II (Macherey-Nagel, 740955) according to manufacturer's instructions;
2) Reverse Transcription of 1 µg total RNA using a mixture of random hexamer and oligo-dT oligonucleotide primer ProtoScript M-MuLV First Strand cDNA Synthesis Kit (e.g. NEB, E6300L). As a negative control to check genomic DNA contamination, samples of RNA are treated in parallel in the presence and absence of reverse transcriptase and used for PCR. Later tests for genomic DNA contamination by PCR amplification show that there is no genomic DNA contamination.

PCR amplification of cDNA is performed using Phusion Flash HF Polymerase and reagents (New England Biolabs) in a final volume of 20 µl containing 1.25 µM of each primer shown in Table 1. PCR amplification consists of initial denaturation at 98° C. for 10 sec followed by cycles of denaturation at 98° C. for 1 sec, primer annealing at 55° C. for 7 sec, and extension at 72° C. for 10 sec. After 30 cycles of amplification, a final extension step followed at 72° C. for 10 min. PCR products are separated on 2% agarose gels and stained with ethidium bromide as shown in FIG. 4. All results are summarized in Table 1.

Example 5

Measuring Human Taste Cell Response to Taste Molecules by Fluo-4 Fluorescent Calcium Imaging Assay RT-PCR gene expression analysis of human taste cells was performed with the cells of this invention (BR-HTC8) as shown in Table 1 and revealed that several members of he TAS2R family of G protein-coupled receptors (GPCRs), which are known to detect bitter taste molecules, are expressed in these cells as shown in Table 2. It is known to a person skilled in the art that known bitter taste molecules interact with members of TAS2R GPCR family and trigger taste cell specific signal transduction pathways. Studies using a variety of model organisms revealed that these pathways may involve a large number of signalling factors, which may vary significantly depending on the model taste cell studied. As a consequence, the taste molecule-dependent stimulation of a taste cell may result in various signals, which depends the taste molecule, the combination of taste molecule receptors and signal transduction components present in the cell. These signals include release and synthesis of second messengers including $Ca^{2+}$, IP3, DAG, cGMP, or cAMP, and others. Conventionally, it is assumed by a person skilled in the art that most pathways converge in changes in intracellular calcium, or changes in cellular membrane potential, or changes in intracellular calcium and changes in cellular membrane potential, which can be conveniently measured by the assays described herein. In order to proof 1) that the human taste cells described in this invention respond to stimulation with appropriate taste molecules with any of the established signalling pathways and 2) that the signalling pathway employed may vary depending on the stimulus and the cognate taste receptor involved, we measured the endogenous response of human taste cells to select taste molecules, including salicin and saccharin, which have been previously shown in recombinant cell-based assays to act via TAS2R16 (Bufe, Hofmann, Krautwurst, Raguse, & Meyerhof, 2002, The human TAS2R16 receptor mediates bitter taste in response to beta-glucopyranosides. *Nat Genet* 32: 397-401) and TAS2R43/TAS2R44 (Kuhn et al., 2004, Bitter taste receptors for saccharin and acesulfame K. *J Neurosci* 24: 10260-10265), respectively.

Stimulation of human taste cells described in this invention, which harbor endogenous taste receptors, hormone receptors, ion channels, and signalling transduction components known for taste stimulus reception and taste signal transduction and modulation, can trigger signalling cascades and, as one of several possible outcomes, an increase of intracellular calcium, which can be measured by the Fluo-4 assay. Before the assay, cells are maintained in HTC medium for at least 48 hours as described in Example 1. Cells are then trypsinized with accutase (e.g. PAA, L11-007) or TrypLE (e.g. Gibco, 12563) and seeded into poly-D-lysine coated 96-well assay plates (e.g. Corning) at a density of 15,000 cells/well in 100 µl HTC medium.

After 24 hours, the cells (still in 100 µl medium) are stained by addition of 100 µl of Fluo-4 staining solution, which consists of KH buffer (10 mM HEPES pH7.4 containing 118 mM NaCl, 4.7 mM KCl, 4.2 mM $NaHCO_3$, 1.2 mM $KH_2PO_4$, 1.2 mM $MgSO_4$, 1.3 mM $CaCl_2$) containing 4 µM Fluo-4 (Molecular Probes) and incubation for 1 hour at 37° C. Final Fluo-4 concentration in the staining solution/medium mixture is 2 µM. Staining solution is then replaced by 80 µl KH-buffer per well and plates are transferred into a fluorescence microplate reader to monitor changes in $Ca^{2+}$-dependent fluorescence (excitation 488 nm, emission 530 nm) after the addition of 20 µl KH-buffer supplemented with the test molecule under investigation. The test molecule was added 16 seconds after starting the scan and baseline recording, mixed twice, and then recording continued for additional 44 seconds. Data points of a total of 18 reads were collected. Data analysis/Data recording—Calcium mobilization was measured as the change of peak fluorescence (ΔF) over the baseline level (F). Data were expressed as the mean S.E. of the ΔF/F value of replicated independent samples. Data analysis was done with software provided by the manufacturer of the microplate reader (e.g. Molecular Devices).

To test, whether stimulation of human taste cells with these taste molecules leads to changes in intracellular calcium the Fluo-4 fluorescent calcium imaging assay was performed as described above. Non-taste cells including HEK293 cells and non-lingual, proliferating primary cells isolated from the oral cavity served as a control and were treated equally throughout the procedure. Changes in $Ca^{2+}$-dependent Fluo-4 fluorescence were recorded on a Molecular Devices Fluorescence microplate reader. Measurement was started by addition of increasing concentrations of the taste molecules in KH-buffer to the cells. KH-buffer served as negative control and KH-buffer containing 1 µM ionomycin served as a positive control. Addition of salicin, saccharin, and aristolochic acid, which is has been previously established as a bitter taste molecule activating TAS2R16 (Bufe et al., The human TAS2R16 receptor mediates bitter taste in response to beta-glucopyranosides. *Nat Genet* (2002) 32: 397-401) and TAS2R43/TAS2R44 (Kuhn et al., Bitter taste receptors for saccharin and acesulfame K., *J Neurosci* (2004) 24: 10260-10265) led to a dose-dependent increase of Fluo4-fluorescence as shown in FIG. 5A and Table 2. Calcium signals for each test molecule are depicted as Relative Fluorescence Units (RFU), which means that calcium mobilization in response to taste molecules was calculated dF/F0, with dF is (peak fluorescence F1−baseline fluorescence F0). Peak fluorescence intensity occurred 20-30 sec after addition of the taste molecules. Data were obtained from several independent experiments and performed in triplicates.

Stimulation of human taste cells with salicin and saccharin in the presence of 5 µM U73122, a known inhibitor of Phospolipase Cβ2 (PLCβ2) revealed that calcium signalling of human taste cell is inhibited by U73122 when cells are stimulated with salicin, however, the response to saccharin is not reduced. Stimulation of human taste cells with salicin and saccharin in the presence of 0.5 µM H89, a known inhibitor of Protein Kinase A (PKA) revealed that calcium signalling of human taste cell was slightly inhibited by H89 when cells are stimulated with salicin, however, the response to saccharin is not reduced as shown in FIG. 5B. These data indicate that human taste cells employ distinct signalling pathways when responding to these stimuli, which is consistent with previously published data (Hacker et al., Evidence for two populations of bitter responsive taste cells in mice. *Journal of neurophysiology* (2008) 99: 1503-1514; Ogura et al., Taste receptor cell responses to the bitter stimulus denatonium involve $Ca^{2+}$ influx via store-operated channels. *Journal of neurophysiology* (2002) 87: 3152-3155).

The finding that stimulation with salicin led to a PLCb2-dependent calcium response, which is assumed to rely on internal $Ca^{2+}$ stores (Clapp et al., Immunocytochemical evidence for co-expression of Type III IP3 receptor with signalling components of bitter taste transduction. *BMC Neurosci*, 2001, 2: 6; Miyoshi et al., IP(3) receptor type 3 and PLCbeta2 are co-expressed with taste receptors T1R and T2R in rat taste bud cells. *Chem Senses,* 2001, 26: 259-265) whereas addition of saccharin triggered a PLCb2-independent increase of intracellular calcium, prompted us to test whether the saccharin response of BR-HTC8 cells depends on extracellular calcium. In order to perform to the Fluo-4 fluorescent calcium imaging experiment in the absence of extracellular $Ca^{2+}$ the procedure was conducted as described above, however, the KH-buffer was prepared without addition of $Ca^{2+}$. Measurement was started by addition of increasing concentrations of the taste molecules in KH-buffer without $Ca^{2+}$ to the cells. KH-buffer without $Ca^{2+}$ served as negative control and KH-buffer without $Ca^{2+}$ containing 1 µM ionomycin served as a positive control. Addition of salicin led to a dose-dependent increase of Fluo4-fluorescence in the absence of extracellular $Ca^{2+}$ as shown in FIG. 5C. In contrast, addition of increasing concentrations of saccharin did not trigger increase of intracellular $Ca^{2+}$ and Fluo4-fluorescence as shown in FIG. 5C.

These data confirm that the PLCb2-dependent $Ca^{2+}$ response to salicin relies on internal $Ca^{2+}$ stores, whereas the PLCb2-independent $Ca^{2+}$ response to saccharin depends on extracellular $Ca^{2+}$, which further suggests that the gustatory response of human taste cells to bitter taste stimuli is not uniform but employs distinct signaling pathways.

To test whether the described distinct signaling pathways interact, BR-HTC8 cells were stimulated with salicin alone and salicin in combination with saccharin in the absence of extracellular calcium. Measurement was started by addition of increasing concentrations of salicin in KH-buffer without $Ca^{2+}$, which also contained four different concentrations of saccharin. Surprisingly, even though saccharin elicited no response when applied alone, the PLCb2-dependent increase of intracellular calcium in response to salicin was strongly enhanced as shown in FIG. 5C. These results suggest that crosstalk between bitter taste receptors and/or signaling pathways may occur in human taste cells, which can lead to modulation of taste response.

RT-PCR gene expression analysis of human taste cell lines described in this study (BR-HTC8) further revealed that CD36 is expressed in said cells as shown in Example 4, FIG. 4, and Table 1, which indicates to a person skilled in the art, that the cells may be responsive to fatty acids and fat. Addition of oleic acid and linoleic acid led to a dose-dependent increase of Fluo4-fluorescence in human taste cells including BR-HTC8 as shown in FIG. 5A.

Example 6

Measuring Human Taste Cell Response to Taste Molecules by FLIPR Fluorescent Membrane Potential Imaging Assay RT-PCR gene expression analysis of human taste cell lines described in this invention (BR-HTC8) as shown in Table 1 revealed that several members of the TAS2R family of G protein-coupled receptors (GPCRs), which are known to detect bitter taste molecules, are expressed in said cells as shown in in Example 4 and Table 2.

Fluo-4 fluorescent calcium imaging assays further revealed that stimulation of said human taste cells with taste molecules leads to a in intracellular calcium. Addition of salicin, saccharin, and aristolochic Acid, which is have been previously established as a bitter taste molecules activating TAS2R16 (Bufe et al., The human TAS2R16 receptor mediates bitter taste in response to beta-glucopyranosides. *Nat Genet* (2002) 32: 397-401) and TAS2R43/TAS2R44 (Kuhn et al., Bitter taste receptors for saccharin and acesulfame K., *J Neurosci* (2004) 24: 10260-10265) led to a dose-dependent increase of Fluo4-fluorescence as shown in Example 5, FIG. 5A, and Table 2.

Moreover, stimulation of human taste cells with salicin and saccharin in the presence of 5 µM U73122, a known inhibitor of Phospholipase Cβ2 (PLCβ2) revealed, that calcium signalling of human taste cell is inhibited by U73122 when cells are stimulated with salicin, however, the response to saccharin is not reduced as shown in Example 5 and FIG. 5B. Stimulation of human taste cells with salicin and saccharin in the presence of 0.5 µM H89, a known inhibitor of Protein Kinase A (PKA) revealed, that calcium signalling of human taste cell was slightly inhibited by H89 when cells are stimulated with salicin, however, the response to saccharin is not reduced as shown in Example 5 and FIG. 5B.

In addition to an increase of intracellular calcium, a second possible outcome was that signalling pathways trigger ion fluxes inducing a decrease of the cellular membrane potential. This cell depolarization was measured by using voltage-sensitive dyes including FLIPR fluorescent membrane potential (FMP) dye (Molecular Devices R8123). Before the assay, cells were maintained in HTC medium for at least 48 hours as described above in Example 1. Cells were then trypsinized with accutase (e.g. PAA, L11-007) or TrypLE (e.g. Gibco, 12563) and seeded into poly-D-lysine coated 96-well assay plates (Corning) at a density of 15,000 cells/well in 1000 HTC medium.

After 24 hours, medium was removed and the cells are washed once with 100 µl KH buffer (10 mM HEPES pH7.4 containing 118 mM NaCl, 4.7 mM KCl, 4.2 mM $NaHCO_3$, 1.2 mM $KH_2PO_4$, 1.2 mM $MgSO_4$, 1.3 mM $CaCl_2$) and then stained with 200 µl KH buffer containing FLIPR FMP dye according instructions of the manufacturer (Molecular Probes) and incubation for 2 hours at 37° C. The plates were then transferred into a fluorescence microplate reader to monitor changes in membrane potential-dependent fluorescence (excitation 530 nm, emission 565 nm) after the addition of 50 µl KH-buffer supplemented with the test molecule under investigation. The test molecule was added 16 seconds after starting the scan and baseline recording, mixed twice, and then recording continued for additional 74 seconds. Data points of a total of 35 reads were collected.

Data analysis/Data recording—Changes of the membrane potential was measured as the change of peak fluorescence (ΔF) over the baseline level (F). Data were expressed as the mean S.E. of the ΔF/F value of replicated independent samples. Data analysis was done with software provided by the manufacturer of the microplate reader (Molecular Devices).

To test, whether stimulation of human taste cells with taste molecules leads to changes in cellular membrane potential the FLIPR fluorescent membrane potential assay was performed as described above. Non-taste cells including HEK293 cells and non-lingual, proliferating primary cells isolated from the oral cavity served as a control and were treated equally throughout the procedure. Changes in membrane potential were recorded on a Molecular Devices Fluorescence microplate reader. Measurement was started by addition of increasing concentrations of the taste molecules in KH-buffer to the cells. KH-buffer served as negative control and KH-buffer containing 4 µM FCCP (e.g. Sigma, C2920) served as a positive control. Addition of saccharin and aristolochic acid, which is has been previously established as a bitter taste molecule activating TAS2R43/TAS2R44 Kuhn et al., Bitter taste receptors for saccharin and acesulfame K., *J Neurosci* (2004) 24: 10260-10265) and of ATP led to a dose-dependent decrease of membrane potential, which corresponds to an increase in FLIPR FMP dye fluorescence as shown in FIG. 6. Addition of salicin did not elicit significant changes in cellular membrane potential as shown in Table 2. Signals for each test molecule are depicted as Relative Fluorescence Units (RFU), which means that a decrease in cellular membrane potential in response to taste molecules was calculated dF/F0, with dF is (peak fluorescence F1–baseline fluorescence F0). Data were obtained from several independent experiments and performed in triplicates. These experiments revealed that said human taste cells respond to taste molecules including saccharin and aristolochic Acid with a decrease in cellular membrane potential as shown in FIG. 6 and an increase in intracellular calcium as shown in Example 5, FIG. 5A, and Table 2. However, said human taste cells respond to other taste molecules including salicin only with an increase in intracellular calcium and not with a significant change in cellular membrane potential as summarized in Table 2. Other taste molecules including acesulfame K induce a decrease in cellular membrane potential in said taste cells and do not trigger an increase in intracellular calcium as shown in Table 2. These results further indicate that said human taste cells can respond to taste molecules with distinct or overlapping signalling pathways.

It is known to a person skilled in the art that some taste cells release ATP upon stimulation by taste molecules through hemichannels including PANX1, which is also expressed in said human taste cells presented in this invention as shown in Example 4, FIG. 4, and Table 1 and is released from taste cells and activates ionotropic ATP receptors (P2X2/P2X3) on taste nerves (Bo, X. et al., Localization of ATP-gated P2X2 and P2X3 receptor immunoreactive nerves in rat taste buds. *Neuroreport*, 1999, 10(5): 1107-1111; Kataoka, S. et al., Expression of ATP-gated P2X3 receptors in rat gustatory papillae and taste buds. *Archives of Histology and Cytology*, 2006, 69(4): 281-288) as well as metabotropic (P2Y) receptors on taste cells (Baryshnikov, S. G. et al., Calcium signalling mediated by P2Y receptors in mouse taste cells. *Journal of Neurophysiology*, 2003, 90(5): 3283-3294; Huang, Y. A. et al., Autocrine and paracrine roles for ATP and serotonin in mouse taste buds. *J Neurosci*, 2009, 29(44): 13909-13918). Stimulation of said human taste cells with ATP triggered a decrease in cellular membrane potential as shown in FIG. 6 as well as an increase in intracellular calcium, which has bee shown by Fluo-4 calcium imaging assay as summarized in Table 2. These findings further indicate that human taste cell lines described in this innovation including BR-HTC8 share components for the release of transmitter molecules including PANX1 with taste cells derived from other model organisms including rodents and also share the responsiveness to ATP.

Example 7

Measuring Human Taste Cell Response to Hormones by Fluo-4 Fluorescent Calcium Imaging Assay RT-PCR gene expression analysis of human taste cell lines described in this invention (BR-HTC8) revealed that the gene encoding the oxytocin receptor OXTR is expressed in said cells as shown in example 4, FIG. 4, and table 1.

It is known to a person skilled in the art that the anorectic peptide oxytocin leads to calcium signalling in a population of rodent taste bud cells expressing the oxytocin-receptor gene OXTR (Sinclair et al., 2010) and that oxytocin knockout mice showed an overconsumption of salty and sweet solutions in preference tests (Billings, L. B. et al., Oxytocin null mice ingest enhanced amounts of sweet solutions during light and dark cycles and during repeated shaker stress. *Behavioural brain research*, 2006, 171(1): 134-141; Sclafani, A. et al., Oxytocin knockout mice demonstrate enhanced intake of sweet and nonsweet carbohydrate solutions. *American journal of physiology. Regulatory, integrative and comparative physiology*, 2007, 292(5): R1828-1833; Vollmer, R. R. et al., Sodium ingestion in oxytocin knockout mice. *Experimental Neurology*, 2006, 202(2): 441-448).

However, human taste cell lines, which express genes encoding gustatory receptors, ion channels and signalling components as well as genes encoding hormone receptors including leptin receptor (LEPR) and oxytocin receptor (OXTR) were not yet available to test endogenous responses of human taste cells to taste molecules as well as peptide hormones.

Conventionally, it can be assumed by a person skilled in the art that the consequences of stimulating a human taste cell expressing OXTR with oxytocin most likely results in changes in intracellular calcium, or changes in cellular membrane potential, or changes in intracellular calcium and changes in cellular membrane potential, which can be conveniently measured by the assays described herein. In order to proof that the human taste cells described in this invention respond to stimulation with oxytocin with any of the established signalling, we measured the endogenous response of human taste cells to oxytocin To test, whether stimulation of human taste cells with oxytocin leads to changes in intracellular calcium the Fluo-4 fluorescent calcium imaging assay was performed as described above in Example 5. Briefly, the human taste cells were seeded in 96-well plates and stained with 2 µM of the calcium-sensitive fluorescence dye Fluo4 in HTC/KH buffer medium for one hour at 37° C. with subsequent replacement of the staining solution with KH-buffer. Non-taste cells including HEK293 cells and non-lingual, proliferating primary cells isolated from the oral cavity served as a control and were treated equally throughout the procedure. Changes in $Ca^{2+}$-dependent Fluo-4 fluorescence were recorded on a Molecular Devices Fluorescence microplate reader. Measurement was started by addition of increasing concentrations of oxytocin in KH-buffer to the cells. KH-buffer served as negative control and KH-buffer containing 1 µM ionomycin served as a positive control. Addition of oxytocin led to a dose-dependent increase of Fluo4-fluorescence as shown in FIG. 7. Calcium signals for each test molecule are depicted as Relative Fluorescence Units (RFU), which means that calcium mobilization in response to taste molecules was calculated dF/F0, with dF is (peak fluorescence F1–baseline fluorescence F0). Data were obtained from several independent experiments and performed in triplicates.

Stimulation of human taste cells with oxytocin in the presence of 40 nM L371,257, an oxytocin antagonist, revealed that calcium signalling of human taste cell is inhibited by L371,257 as shown in FIG. 7.

Example 8

Measuring Human Taste Cell Response to Hormones by FLIPR Fluorescent Membrane Potential Imaging Assay RT-PCR gene expression analysis of human taste cell lines described in this study (BR-HTC8) revealed that the gene encoding the oxytocin receptor OXTR is expressed in said cells as shown in Example 4, FIG. 5, and Table 1.

Stimulation of said human taste cells with oxytocin was further analysed by the Fluo-4 fluorescent calcium imaging assay performed as described above in example 7 and leads to an increase in intracellular calcium. Said stimulation of human taste cells with oxytocin in the presence of 40 nM L371,257, an oxytocin antagonist, further revealed that calcium signalling of human taste cell was inhibited by L371,257 as described in Example 7.

In addition to an increase of intracellular calcium, a second possible outcome is that signalling pathways trigger ion fluxes inducing a decrease of the cellular membrane potential. This cell depolarization can be measured by using voltage-sensitive dyes including FLIPR fluorescent membrane potential (FMP) dye (Molecular Devices R8123) as described above in Example 6. To test, whether stimulation of human taste cells with oxytocin leads to changes in cellular membrane potential the FLIPR fluorescent membrane potential assay was performed as described above. Non-taste cells including HEK293 cells and non-lingual, proliferating primary cells isolated from the oral cavity served as a control and were treated equally throughout the procedure. Changes in membrane potential were recorded on a Molecular Devices Fluorescence microplate reader. Measurement was started by addition of increasing concentrations of oxytocin in KH-buffer to the cells. KH-buffer served as negative control and KH-buffer containing 4 μM FCCP (e.g. Sigma, C2920) served as a positive control. Addition of oxytocin led to a dose-dependent decrease of membrane potential, which corresponds to an increase in FLIPR FMP dye fluorescence as shown in FIG. 8. Signals for each test molecule are depicted as Relative Fluorescence Units (RFU), which means that a decrease in cellular membrane potential in response to taste molecules was calculated dF/F0, with dF is (peak fluorescence F1−baseline fluorescence F0). Data were obtained from several independent experiments and performed in triplicates. These experiments revealed that said human taste cells respond to hormones including oxytocin with decrease in cellular membrane potential as shown in FIG. 8 as well as with an increase in intracellular calcium as shown in Example 7 and FIG. 7. These results further indicate that said human taste cells can respond to hormones with distinct or overlapping signalling pathways.

TABLE 1

Gene expression analysis in human taste cells described herein by RT-PCR. Target genes, PCR oligonucleotide primers, PCR amplicon (bp) are given and detection of the corresponding mRNA in BR-HTC8 by RT-PCR is indicated.

| RT-PCR target | NCBI Gene ID | Primer (forward, reverse) | bp | SEQ ID NO: | BR-HTC8 |
|---|---|---|---|---|---|
| TRPV1 | 7442 | TCCAGCAGATGGGCATCTATG | 165 | 5 | present |
|  |  | AGGACAAGTGGGACAGATTCG |  | 6 | — |
| TRPML3 | 55283 | GCAGACAGTTCGTCATCAAG | 250 | 7 | present |
|  |  | CTCCTGCTGAAGCTGAAGTC |  | 8 | — |
| Gustducin | 346562 | GCTGCACTTAGTGCCTATGAC | 205 | 9 | — |
|  |  | GCCCAGTGTATTCTGGAAAGC |  | 10 | — |
| TRPM5 | 29850 | ACGAGATTGATGAAGCCCGTG | 143 | 11 | — |
|  |  | CATGAGCAGCACATTGGTGAC |  | 12 | — |
| Oct-4 | 5460 | CTGGGTTGATCCTCGGACCT | 243 | 13 | present |
|  |  | CCATCGGAGTTGCTCTCCA |  | 14 | — |
| T1R1 | 80835 | CGGAGTCTTCTCCTGACTTCA | 195 | 15 | — |
|  |  | CCGTGGAGTTGTTTATCTCCTC |  | 16 | — |
| T1R2 | 80834 | CGTCGTGGTCGTGTTCTCG | 213 | 17 | — |
|  |  | CACTCGCGGAACTCACTGAAG |  | 18 | — |
| T1R3 | 83756 | CCGCCTACTGCAACTACACG | 133 | 19 | present |
|  |  | CTAGCACCGTAGCTGACCTG |  | 20 | — |
| PLCb2 | 5330 | GACTCCCGGCTTAACTCCCT | 250 | 21 | — |
|  |  | CGGCTGTCAGGTAGGTGTT |  | 22 | — |

TABLE 1-continued

Gene expression analysis in human taste cells described herein by RT-PCR. Target genes, PCR oligonucleotide primers, PCR amplicon (bp) are given and detection of the corresponding mRNA in BR-HTC8 by RT-PCR is indicated.

| RT-PCR target | NCBI Gene ID | Primer (forward, reverse) | bp | SEQ ID NO: | BR-HTC8 |
|---|---|---|---|---|---|
| Keratin 5 | 3852 | ATGTCTCGCCAGTCAAGTGTG | 245 | 23 | present |
|  |  | CTGCCTCCTCTAGTGCTGA |  | 24 | — |
| Keratin 8 | 3856 | GGAGGCATCACCGCAGTTAC | 150 | 25 | present |
|  |  | GGTTGGCAATATCCTCGTACTGT |  | 26 | — |
| NCAM | 4684 | ACATCACCTGCTACTTCCTGA | 137 | 27 | — |
|  |  | CTTGGACTCATCTTTCGAGAAGG |  | 28 | — |
| IP3R3 | 3710 | GACTGCCTCTTCAAGGTGTG | 203 | 29 | present |
|  |  | ACACTGCCATACTTCACGACA |  | 30 | — |
| Keratin 19 | 3880 | AACGGCGAGCTAGAGGTGA | 204 | 31 | present |
|  |  | TTCCGTCTCAAACTTGGTTCG |  | 32 | — |
| Sox 2 | 6657 | TGGACAGTTACGCGCACAT | 215 | 33 | — |
|  |  | CGAGTAGGACATGCTGTAGGT |  | 34 | — |
| TP63 | 8626 | GAGCCGTGAGTTCAACGAGG | 254 | 35 | — |
|  |  | CTTGCCCATCTCTGGTTTCCA |  | 36 | — |
| SHH | 6469 | ACTCCGAGCGATTTAAGGAACT | 249 | 37 | — |
|  |  | CAGACGTGGTGATGTCCACTG |  | 38 | — |
| Ptc 1 | 5727 | GACCGGGACTATCTGCACC | 183 | 39 | present |
|  |  | GAGGCCCACAACCAAGAACTT |  | 40 | — |
| Glast | 6507 | ATCCTTGGATTTACCCTCCGA | 141 | 41 | present |
|  |  | CGCCATTCCTGTGACAAGAC |  | 42 | — |
| NTPD | 953 | CAACTATCTGCTGGGCAAATTCA | 295 | 43 | present |
|  |  | GGCAGGTCTGGATTGAGTTATAC |  | 44 | — |
| Trf2 | 9519 | AAGGAAGATTGCTTTGGAAGGAG | 182 | 45 | present |
|  |  | GCAGACTACGGGCTAAGCG |  | 46 | — |
| Trf3 | 387332 | CACCCTGGTGATACTGACTC | 166 | 47 | — |
|  |  | TACAGGCCAGGTTACAGTG |  | 48 | — |
| Tbp | 6908 | CCACTCACAGACTCTCACAAC | 127 | 49 | present |
|  |  | CTGCGGTACAATCCAGAACT |  | 50 | — |

TABLE 1-continued

Gene expression analysis in human taste cells described herein by RT-PCR. Target genes, PCR oligonucleotide primers, PCR amplicon (bp) are given and detection of the corresponding mRNA in BR-HTC8 by RT-PCR is indicated.

| RT-PCR target | NCBI Gene ID | Primer (forward, reverse) | bp | SEQ ID NO: | BR-HTC8 |
|---|---|---|---|---|---|
| mGlu1 | 2911 | CCAGCGATCTTTTT GGAGGTG | 168 | 51 | — |
| | | CCTCTCGGGCACTT TCTCG | | 52 | — |
| mGlu4 | 2914 | AAGGAAGATTGCTT TGGAAGGAG | 150 | 53 | — |
| | | GCAGACTACGGGCT AAGCG | | 54 | — |
| beta actin | 60 | GTGGGGCGCCCCAG GCACCA | 539 | 55 | present |
| | | CTCCTTAATGTCAC GCACGATTTC | | 56 | — |
| PKD2L1 | 9033 | CCACCTTCACCAAG TTTGAC | 271 | 57 | — |
| | | GCATCAATCTGGGA CACTAC | | 58 | — |
| Keratin 14 | 3861 | CATGAGTGTGGAAG CCGACAT | 154 | 59 | — |
| | | GCCTCTCAGGGCAT TCATCTC | | 60 | — |
| Mash1 | 429 | CGCGGCCAACAAGA AGATG | 199 | 61 | — |
| | | CGACGAGTAGGATG AGACCG | | 62 | — |
| SCNN1A | 6337 | TCGAGTTCCACCGC TCCTA | 156 | 63 | — |
| | | GCCAGTACATCATG CCAAAGG | | 64 | — |
| SCNN1B | 6338 | CAGGACCTACTTGA GCTGGGA | 170 | 65 | present |
| | | CCAGGATTCTCTCC AGGACAG | | 66 | — |
| SCNN1G | 6340 | CCGACCATTAAAGA GCTGATGC | 120 | 67 | — |
| | | AGTCAGTGTGAACC CGATCCA | | 68 | — |
| SCNN1D | 6339 | GGCATCAGGGTCAT GGTTCAC | 267 | 69 | present |
| | | GTGGAGGTAGTAGC CACAGG | | 70 | — |
| SNAP 25 | 6616 | CTTCATCCGCAGGG TAACAAA | 116 | 71 | present |
| | | TCTCATTGCCCATA TCCAGGG | | 72 | — |
| PC 1/3 | 5122 | TTTGGGTCAGATTG GTTCACTTG | 126 | 73 | present |
| | | GCCCATATCACACG ATCATCAT | | 74 | — |
| ESPN | 83715 | CAGAGTGCAGGACA AAGACAA | 153 | 75 | — |
| | | CAGAGTGCAGGACA AAGACAA | | 76 | — |
| GOAT | 619373 | GCTGGCAGACCTTG TGTCA | 233 | 77 | — |
| | | CAAGTAGCTGAAAT AGGGCAGTG | | 78 | — |
| Oct-11 | 25833 | TTCCCGGCCACTTA CAGTCT | 194 | 79 | — |
| | | CAGGTGGGGTTCTA AAGAGGAT | | 80 | — |
| PLCD4 | 84812 | TCAGAATGACGGCA TGACAGT | 235 | 81 | present |
| | | CCCTCGCATCCATA TCTGGG | | 82 | — |
| CXCL14 | 9547 | CGTGTGGACGGGTC CAAATG | 239 | 83 | — |
| | | TCGTAGACCCTGCG CTTCTC | | 84 | — |
| ADRA1A | 146 | CTCCAGCCTGTCGC ACAAG | 152 | 85 | — |
| | | TGTAGTCGGCCAAT TCGTAGG | | 86 | — |
| ADRB1 | 153 | ATCGAGACCCTGTG TGTCATT | 267 | 87 | — |
| | | GTAGAAGGAGACTA CGGACGAG | | 88 | — |
| ADORA2B | 136 | TGCACTGACTTCTA CGGCTG | 147 | 89 | present |
| | | GGTCCCCGTGACCA AACTT | | 90 | — |
| SYN 2 | 6584 | CTGTCCCAAGCGGT AAAGCA | 186 | 91 | — |
| | | TTCTGCCTGTTCCA CCTTGAT | | 92 | — |
| SYT 1 | 83849 | TAGGACCCAACTGA GCAGG | 237 | 93 | — |
| | | GGGAAGTCGGTCTC ACTTTTG | | 94 | — |
| NRCAM | 4897 | TGACCCTCGGGAGA ATATTG | 272 | 95 | — |
| | | TGGTCCACAATGGT GATCTG | | 96 | — |
| OXTR | 5021 | CTGCTACGGCCTTA TCAGCTT | 242 | 97 | present |
| | | CGCTCCACATCTGC ACGAA | | 98 | — |
| GPR 120 | 338557 | CGATTTGCACACTG ATTTGGC | 405 | 99 | — |
| | | TGCACAGTGTCATG TTGTAGA | | 100 | — |
| GPR 40 | 2864 | GGGTCTGGTCTTTG GGTTGG | 201 | 101 | — |
| | | CAGCCCACGTAGCA GAAGG | | 102 | — |
| CD36 | 948 | AAGCCAGGTATTGC AGTTCTTT | 220 | 103 | present |
| | | GCATTTGCTGATGT CTAGCACA | | 104 | — |
| KCNC2 | 3747 | ACCCTACTCGTCC AGAG | 151 | 105 | — |
| | | ACAAACACTTGTGCC ATTGATGA | | 106 | — |

TABLE 1-continued

Gene expression analysis in human taste cells described herein by RT-PCR. Target genes, PCR oligonucleotide primers, PCR amplicon (bp) are given and detection of the corresponding mRNA in BR-HTC8 by RT-PCR is indicated.

| RT-PCR target | NCBI Gene ID | Primer (forward, reverse) | bp | SEQ ID NO: | BR-HTC8 |
|---|---|---|---|---|---|
| KCNQ1 | 3784 | GGAGCCACACTCTG CTGTC | 196 | 107 | — |
| | | CTTACAGAACTGTC ATAGCCGTC | | 108 | — |
| KCNH2 | 3757 | CAACCTGGGCGACC AGATAG | 142 | 109 | — |
| | | GGTGTTGGGAGAGA CGTTGC | | 110 | — |
| GNG13 | 51764 | GGAGTGGGACGTGC CACAG | 191 | 111 | — |
| | | TGGTGCATTTGCCC TTTTCC | | 112 | — |
| GNB3 | 2784 | AAGTGCCTCGCAAG ATGGG | 232 | 113 | present |
| | | GCAGGAGAGATAAC CTGTGTGAG | | 114 | — |
| GNA13 | 10672 | CAGCAACGCAAGTC CAAGGA | 220 | 115 | present |
| | | CCAGCACCCTCATA CCTTTGA | | 116 | — |
| GNA11 | 2767 | GGCTTCACCAAGCT CGTCTAC | 172 | 117 | present |
| | | CACTGACGTACTGA TGCTCG | | 118 | — |
| GNA14 | 9630 | GAGCGATGGACACG CTAAGG | 168 | 119 | present |
| | | TCCTGTCGTAACAC TCCTGGA | | 120 | — |
| GNA12 | 2768 | CCGCGAGTTCGACC AGAAG | 245 | 121 | — |
| | | TGATGCCAGAATCC CTCCAGA | | 122 | — |
| GNB1 | 2782 | ATGCAACTCTCTCT CAGATCACA | 143 | 123 | present |
| | | CGAGGCACTGACGA GAAGC | | 124 | — |
| GNAL | 2774 | CACGTCAATGGGTT TAATCCCG | 187 | 125 | — |
| | | CAAAGTCAGTGATA GGGGCTATG | | 126 | — |
| GNA15 | 2769 | GCTCGATTCAGCCG TGTACTA | 190 | 127 | — |
| | | CCATTTCTTACGCT CTGACTTCT | | 128 | — |
| GNAQ | 2776 | TGGGTCAGGATACT CTGATGAAG | 144 | 128 | present |
| | | TGTGCATGAGCCTT ATTGTGC | | 130 | — |
| PANX1 | 24145 | CCACGGAGTACGTG TTCTCG | 240 | 131 | present |
| | | CCGCCCAGCAATAT GAATCC | | 132 | — |
| ROMK | 3758 | ATCTGGACAACGGT ACTTGACC | 104 | 133 | — |
| | | TGCATACCACAGGA GACCAAA | | 134 | — |
| LEPR | 3953 | CTTGGTCCAGCCCA CCATTG | 182 | 135 | present |
| | | ATTCCTGGGCCATC CAGTC | | 136 | — |
| P2RY12 | 64805 | CACTGCTCTACACT GTCCTGT | 190 | 137 | present |
| | | AGTGGTCCTGTTCC CAGTTTG | | 138 | — |
| P2RX7 | 5027 | ACACCGCAGACTAC ACCTTC | 107 | 139 | present |
| | | GGTGGGATACTCGG GACAC | | 140 | — |
| KCNA1 | 3736 | CATCGTGGAAACGC TGTGTAT | 232 | 141 | — |
| | | AACCCTTACCAAGC GGATGAC | | 142 | — |
| KCNA2 | 3737 | TAGTGGGGTGACCT TCCACA | 147 | 143 | — |
| | | CTGGGACAGGCAAA GAACC | | 144 | — |
| KCNA3 | 3738 | TTTTCTCCAGCGCG GTCTAC | 119 | 145 | — |
| | | CATATCGCCGTAAC CCACTGT | | 146 | — |
| KCNA5 | 3741 | CGCGTCCACATCAA CATCTC | 250 | 147 | — |
| | | GGTAGAAGCGTATC TCGTCCG | | 148 | — |
| KCNA6 | 3742 | AGGATGAAGACGAT TCCTACACA | 243 | 149 | — |
| | | AGGGGAAGATAGCC ACCAAGT | | 150 | — |
| KCNB1 | 3745 | CCATTCTGCCATAC TATGTCACC | 196 | 151 | — |
| | | AGCAAGCCCAACTC ATTGTAG | | 152 | — |
| KCNB2 | 9312 | GCCAAGAACTTGAT TACTGGGG | 125 | 153 | — |
| | | CTCTCGCATAGTCT CTGCCT | | 154 | — |
| KCNC1 | 3746 | GCCCCAACAAGGTA GAGTTCA | 181 | 155 | — |
| | | TGGCGGGTCAGCTT AAAGATG | | 156 | — |
| CREB1 | 1385 | CCACTGTAACGGTG CCAACT | 142 | 157 | present |
| | | GCTGCATTGGTCAT GGTTAATGT | | 158 | — |
| PDE1A | 5136 | TTGGCTTCTACCTT TACACGGA | 212 | 159 | present |
| | | AGGGCAAATACATC GAAAGACC | | 160 | — |
| SCN2A | 6326 | TCTAAGCGTGTTTG CGCTAAT | 139 | 161 | — |
| | | ACCATTCCCATCCA ATGAATTGT | | 162 | — |

TABLE 1-continued

Gene expression analysis in human taste cells described herein by RT-PCR. Target genes, PCR oligonucleotide primers, PCR amplicon (bp) are given and detection of the corresponding mRNA in BR-HTC8 by RT-PCR is indicated.

| RT-PCR target | NCBI Gene ID | Primer (forward, reverse) | bp | SEQ ID NO: | BR-HTC8 |
|---|---|---|---|---|---|
| SCN3A | 6328 | CTGAGCGTGTTTGCTCTCATT | 237 | 163 | present |
| | | GAGTAAAGGGTCTTTTTGCCCAT | | 164 | — |
| SCN9A | 6335 | ATTCGTGGCTCCTTGTTTTCTG | 209 | 165 | present |
| | | CTACTGGCTTGGCTGATGTTAC | | 166 | — |
| ACCN1 | 40 | GGAAACGACATTTGAAGCAGGA | 170 | 167 | — |
| | | CTGAGGATCGGCACTCACC | | 168 | — |
| ACCN2 | 41 | ACATGCGTGAGTTCTACGACC | 136 | 169 | — |
| | | TTGAACGTGTAGCACTTTCCAT | | 170 | — |
| ACCN3 | 9311 | GAGAAAGCCACCGGCTCATC | 292 | 171 | — |
| | | AAGTTCTCAGGCCCACAAGG | | 172 | — |
| HTR1A | 3350 | ACCTGCGACCTGTTCATCG | 176 | 173 | — |
| | | AGGAAGCCAATAAGCCAAGTG | | 174 | — |
| HTR1B | 3351 | AACTACCTGATGCGCCTCTCTG | 114 | 175 | — |
| | | ACAAGTGATGTCCGACGACAG | | 176 | — |
| HTR1D | 3352 | CTCCAACAGATCCCTGAATGC | 157 | 177 | — |
| | | CCTGGTGAGTAAGATGGTGGT | | 178 | — |
| HTR1E | 3354 | CTGGGCTCAACGTACTCCCAG | 182 | 179 | — |
| | | GCCACAGCATTTCTTCTGAG | | 180 | — |
| HTR2A | 3356 | CTTTGTGCAGTCTGGATTTACCT | 173 | 181 | — |
| | | ACTGATATGGTCCAAACAGCAAT | | 182 | — |
| HTR2B | 3357 | CTTGACGTTCTCTTTTCAACCGC | 108 | 183 | present |
| | | CCGTGAGTTATATTGATTGGCCT | | 184 | — |
| HTR2C | 3358 | TCTTAATGTCCCTAGCCATTGCT | 180 | 185 | — |
| | | CCAGCGATATAGCGCAGAGG | | 186 | — |
| HTR3A | 3359 | GAAGCCAACCACCGTATCCAT | 218 | 187 | — |
| | | CCACATCCACGAACTCATTGAT | | 188 | — |
| HTR3B | 9177 | GGTCTCTGCGTGCAGTTTAGA | 188 | 189 | — |
| | | AGGACACAGATAGAAGTTCCCAC | | 190 | — |
| HTR3C | 170572 | TTCCGGTCTCACTGCCTATATC | 129 | 191 | — |
| | | AAGGTGAAGGTACAAGTTCTGTTG | | 192 | — |
| HTR3D | 200909 | CCCTACGTGGTAAACTTTCTGG | 179 | 193 | — |
| | | TGTGATGAAGTGCTAGTGGCT | | 194 | — |
| HTR3E | 285242 | AGACGCATCCCGGAACATC | 165 | 195 | — |
| | | GGCACGAGAAGGTTTATGACA | | 196 | — |
| HTR4 | 3360 | TGCCCTTTGGTGCAATTGA | 188 | 197 | — |
| | | CAGAGGGGTCATCTTGTTCCTA | | 198 | — |
| HTR5A | 3361 | TAAGCCGCGAGCCTTCCTA | 143 | 199 | — |
| | | GGGTGAGACGCTATTGGTCTT | | 200 | — |
| HTR6 | 3362 | CAGGCGTCTAGCCACGAAG | 166 | 201 | — |
| | | CCATGTGAGGACATCGAAGAGG | | 202 | — |
| HTR7 | 3363 | CACCTCCGCTCTTTCCTTCTG | 187 | 203 | — |
| | | CGTAGTTGATCTGTTCCCCAC | | 204 | — |
| TRPM8 | 79054 | GCAAGTGTGGCTATGCCCA | 109 | 205 | — |
| | | CCAAAGGCGTCGGTCGGAA | | 206 | — |
| TRPA1 | 8989 | TGTGACGATATGGACACCTTCT | 215 | 207 | present |
| | | TTGAAGTTTCGGAGATTTGGGTT | | 208 | — |
| CD73 | 4907 | GCCTGGGAGCTTACGATTTTG | 207 | 209 | — |
| | | GGTGAACCAGATAGTGCCCT | | 210 | — |
| ACPP | 55 | CCCCATAAAGGAATCCTCATGGC | 173 | 211 | — |
| | | TCAAAGTCCGGTCAACGTCTG | | 212 | — |
| P2RX2 | 22953 | CTGCCTCGTCAGGCTACAAC | 142 | 213 | — |
| | | GTGGGAATCAGGCTGAACTTC | | 214 | — |
| P2RX3 | 5024 | ATGCGCCTTGACCAAGACG | 166 | 215 | — |
| | | GGCCAGAGCCAAATTGAACA | | 216 | — |
| FAM38A | 9780 | ATGTTGCTCTACACCCTGACC | 203 | 217 | — |
| | | CCAGCACACACATAGATCCAGT | | 218 | — |

TABLE 1-continued

Gene expression analysis in human taste cells described herein by RT-PCR. Target genes, PCR oligonucleotide primers, PCR amplicon (bp) are given and detection of the corresponding mRNA in BR-HTC8 by RT-PCR is indicated.

| RT-PCR target | NCBI Gene ID | Primer (forward, reverse) | bp | SEQ ID NO: | BR-HTC8 |
|---|---|---|---|---|---|
| FAM38B | 63895 | CACGTTGGTGAGCCTTGAAG | 243 | 219 | — |
| | | TCAAACTCCGGGTTACTCTGT | | 220 | — |
| HTR1F | 3355 | TGTCTGGGCTGGCACTGATG | 157 | 221 | — |
| | | ACAATGCTGAAGGGCATCAC | | 222 | — |
| Tbp | 6908 | CCACTCACAGACTCTCACAAC | 127 | 223 | present |
| | | CTGCGGTACAATCCCAGAACT | | 224 | — |
| T2R1 | 50834 | ATCATGTGTTCTGCGAATTGTGC | 230 | 225 | — |
| | | ACCATAAACCCTGCATATTTGCT | | 226 | — |
| T2R2 | 338396 | CAGCCTATGGTTTGCCACTTG | 202 | 227 | — |
| | | CTGAGGGCATCCTCTTCCAC | | 228 | — |
| T2R3 | 50831 | TATCCTGTGGTAGTACCGCATC | 171 | 229 | — |
| | | GGGACACAATTAAGGGAGGCA | | 230 | — |
| T2R4 | 50832 | TTCCTGAACTTGTGACTACGAGA | 146 | 231 | present |
| | | CCTCAAGGAGTGTATTAGCAAGG | | 232 | — |
| T2R5 | 54429 | GCCGTTGGCTTCGCTATCTTA | 157 | 233 | present |
| | | AGACTCAGGTTATAGGCCCTCT | | 234 | — |
| T2R7 | 50837 | TGAAGTGGAGAATTGACAGGGT | 203 | 235 | — |
| | | TGCCAGGTTGAGAAATAACTTGG | | 236 | — |
| T2R8 | 50836 | CTTGTTGGTCAGCCTTATAGCA | 244 | 237 | — |
| | | ACTGCCGGTAGCATAGAGTTTT | | 238 | — |
| T2R9 | 50835 | CAAGGTCATGCTTGCGATTCT | 250 | 239 | — |
| | | CTTGGTGTGTCTAACTAGGGAGA | | 240 | — |
| T2R10 | 50839 | CTACGTGTAGTGGAAGGCATCT | 242 | 241 | present |
| | | TCAATTAGGTTACCGGAGGCAT | | 242 | — |
| T2R13 | 50838 | TTGGCAATCTCCAGAATTGGG | 200 | 243 | — |
| | | GGGCTAGAGAAACTCGCTATTTT | | 244 | — |
| T2R14 | 50840 | ATGGGTGGTGTCATAAAGAGCA | 173 | 245 | present |
| | | AGGCTAATTCGAGAGATTGCCA | | 246 | — |
| T2R16 | 50833 | TGTGCAGAGCAGCCTAATTG | 153 | 247 | present |
| | | TGCAGTAGAACACGGTAAGC | | 248 | — |
| TAS2R38 | 5726 | TCCCTGGGAAGGCACATGAG | 347 | 249 | present |
| | | CAGCACAGTGTCCGGGAATC | | 250 | — |
| T2R39 | 259285 | TCCTCCAGACACCAAAGAGAA | 201 | 251 | present |
| | | CCACTTGTGGAAACTGCCTTAT | | 252 | — |
| T2R40 | 259286 | TGAATAGCTCCATTCCTATCCCC | 229 | 253 | — |
| | | GCCCCTATGTGAGCCTTCAT | | 254 | — |
| T2R41 | 25928 | CACAACTTCTACTACTCTGCCCA | 248 | 255 | — |
| | | AGCAGGGTTATGATGAAGGAGAT | | 256 | — |
| T2R42 | 353164 | TTCTGTCCTTGGTGAGACATACT | 227 | 257 | — |
| | | GCACGAGGGAAAGGCATTTAAG | | 258 | — |
| T2R43 | 259289 | TGGCTTGCTACTACCCTCAG | 347 | 259 | present |
| | | TGGAGCTGCATCTTCTTGAG | | 260 | — |
| TAS2R44 | 259290 | CAGATGCGACTGTAACCACG | 375 | 261 | present |
| | | AGTACCTCACTTGCCGCAAAA | | 262 | — |
| T2R45 | 259291 | ATTCCACCGAGTGGGTGAAG | 306 | 263 | present |
| | | GCACCACCAGAATGACACTC | | 264 | — |
| T2R46 | 259292 | ACAACGGTAACCATCCTAGCA | 280 | 265 | — |
| | | TGAATGCAATAGCTTCGCAGA | | 266 | — |
| T2R47 | 259293 | ACATGGATGAGACTGTATGGACA | 276 | 267 | present |
| | | TGGCACATAACAGAAGAAAGGAG | | 268 | — |
| T2R48 | 259294 | GAAGATGCGGCTCCATAGCAA | 174 | 269 | present |
| | | TGGCAAAGCAGGAGTACAAGT | | 270 | — |
| T2R49 | 259295 | AAGGCTAAGAGTGTAGTTCTGGT | 160 | 271 | present |
| | | AGTTGGAAAGGTGCATTGCAT | | 272 | — |
| T2R50 | 259296 | TCTGGCGGTCTCCAGAATTG | 317 | 273 | — |
| | | CTGCCCACATACTCTCATCC | | 274 | — |

TABLE 1-continued

Gene expression analysis in human taste cells described herein by RT-PCR. Target genes, PCR oligonucleotide primers, PCR amplicon (bp) are given and detection of the corresponding mRNA in BR-HTC8 by RT-PCR is indicated.

| RT-PCR target | NCBI Gene ID | Primer (forward, reverse) | bp | SEQ ID NO: | BR-HTC8 |
|---|---|---|---|---|---|
| T2R60 | 338398 | GGGTGCTACGGAGAATGTTGT | 198 | 275 | — |
| | | TAGAGGACCATAAGGTGGCAG | | 276 | — |

TABLE 2

TAS2R gene expression analysis in human taste cells BR-HTC8 described in this innovation by RT-PCR and taste cell response to cognate bitter molecules in Fluo-4 calcium imaging assays (Fluo-4) and FLIPR fluorescent membrane potential (FMP) assay are given. + indicates that the analysis was successful and that the mRNA was detected by RT-PCR or that stimulation of human taste cells with the respective taste molecule resulted in a dose-dependent increase in intracellular calcium or decrease in cellular membrane potential.

| | RT-PCR | Fluo-4 assay | | FMP assay | |
|---|---|---|---|---|---|
| | BR-HTC8 | BR-HTC8 | | BR-HTC8 | |
| TAS2R1 | — | Thiamine, Isocohumulon (humulone isomers) | — | | |
| TAS2R2 | — | | | | |
| TAS2R3 | — | Chloroquine | — | Chloroquine | + |
| TAS2R4 | present | Colchicine | — | | |
| TAS2R5 | present | | | | |
| TAS2R7 | — | | | | |
| TAS2R8 | — | Chloramphenicole | + | | |
| TAS2R9 | — | Ofloxacine | + | | |
| TAS2R10 | present | | | | |
| TAS2R13 | — | Denatonium benzoat | + | | |
| TAS2R14 | present | Aristolochic acid | + | Aristolochic acid | + |
| TAS2R16 | present | Salicin | + | Salicin | — |
| TAS2R38 | present | PTC | + | PTC | + |
| TAS2R39 | present | EGCG | + | | |
| TAS2R40 | — | | | | |
| TAS2R41 | — | | | | |
| TAS2R42 | — | | | | |
| TAS2R43 | present | Acesulfame K | — | | |
| TAS2R44 | present | Acesulfame K Saccharin | + | Acesulfame K Saccharin | + + |
| TAS2R45 | present | | | | |
| TAS2R46 | — | Orphenadrine | + | | |
| TAS2R47 | present | | | | |
| TAS2R48 | present | | | | |
| TAS2R49 | present | | | | |
| TAS2R50 | — | Andrographolide | — | | |
| TAS2R60 | — | | | | |

The invention claimed is:

1. Human taste cells, wherein the cells are the cells deposited under the DSMZ deposit accession number DSM ACC3169.

2. Human taste cells, wherein the cells are the cells deposited under the DSMZ deposit accession number DSM ACC3169, and wherein the cells
   a) further comprise at least one nucleic acid molecule selected from the group consisting of a nucleic acid molecule encoding a protein taste receptor, a nucleic acid molecule encoding a hormone receptor, a nucleic acid molecule encoding a molecule involved in taste signalling, a nucleic acid molecule encoding an anti-senescence and immortalization promoting compound and an shRNA that targets receptors or downstream signalling molecules involved in taste signalling; or
   b) further comprise at least one deletion in a gene selected from the group consisting of taste receptor genes and downstream signalling molecules involved in taste signalling.

3. The human taste cells of claim 2, wherein the taste receptor is selected from the group consisting of TRPV1, TRPA1, SCNN1A, SCNN1B, SCNN1G, SCNN1D, TRPML3, TRPM5, T1R1, T1R2, T1R3, TAS2R38, TAS2R44, TAS2R1, TAS2R2, TAS2R3, TAS2R4, TAS2R5, TAS2R7, TAS2R8, TAS2R9, TAS2R10, TAS2R13, TAS2R14, TAS2R16, TAS2R39, TAS2R40, TAS2R41, TAS2R42, TAS2R43, TAS2R45, TAS2R46, TAS2R47, TAS2R48, TAS2R49, TAS2R50, TAS2R60, mGlut1, mGlut4, PKD2L1, GPR120, GPR40, CD36, and ROMK.

4. The human taste cells of claim 2, wherein the hormone receptor is selected from the group consisting of OXTR, LEPR, Melanocortin receptors (MCRs) and Serotonin receptors (HTRs).

5. The human taste cells of claim 2, wherein the molecule involved in taste signalling is selected from the group consisting of gustducin, TRPM5, PLCb2, IP3R3, PLCD4, CXCL14, ADRA1A, ADRB1, ADORA2B, KCNC2, KCNQ1, KCNH2, GNG13, GNB3, GNA13, GNA11, GNA14, GNA12, GNB1, GNAL, GNA15, GNAQ, PANX1, P2RY12, P2RX7, KCNA1, KCNA2, KCNA3, KCNA5, KCNA6, KCNB1, KCNB2, KCNC1, PDE1A, SCN2A, SCN3A, SCN9A, ACCN1, ACCN2, and ACCN3.

6. The human taste cells according to claim 2, wherein the shRNA is an shRNA that targets TAS2R16 or TAS2R44.

7. The human taste cells of claim 1 or 2, exhibiting a specific marker expression profile comprising the presence of at least two markers selected from the group consisting of Oct-4, Ptc1, PLCD4, gustducin, PANX1, keratin 19, keratin 5, keratin 8, GLAST, NTPD, OXTR, LEPR, HTR2B, IP3R3, ADORA2B, PDE1A, CD36, TAS2R4, TAS2R5, TAS2R10, TAS2R14, TAS2R16, TAS2R38, TAS2R39, TAS2R43, TAS2R44, TAS2R45, TAS2R47, TAS2R48, TAS2R49, GNAQ, GNA14, GNA14, GNA13, GNB3, GNB1, P2RY12, P2RX7, SCN3A, SCN9A, ENAC beta, ENAC delta, TRPV1, and TRPA1 and/or the lack of expression of at least 1 marker selected from the group consisting of NCAM, PLCb2, PKD2L1, mGLU1, mGLU4, T1R1, T1R2, TRPM8, TRPM5, P2RX2, P2RX3, GPR120, GPR40, Sox2, and keratin 14.

8. The human taste cells of claim 7, wherein the cells maintain the specific marker expression profile comprising the presence of at least two markers in culture for at least 10 generations.

9. An in vitro method for analysing the signalling response of taste cells to a molecule involved in taste signalling, the method comprising:
   (i) contacting the human taste cells of claim 1 or claim 2 with a molecule involved in taste signalling; and
   (ii) determining the signalling response elicited by the molecule involved in taste signalling in the cells.

10. An in vitro method of identifying an agent capable of eliciting a taste response in taste cells, the method comprising:
    (i) adding a test compound to the human taste cells of claim 1 or claim 2 and measuring the signalling response elicited by the test compound in the cells; and
    (ii) comparing the signalling response obtained in (i) with the signalling response elicited in the human taste cells of claim 1 by (a) known molecule(s) involved in taste signalling;
    wherein an identical or substantially identical signalling response determined in (ii) indicates that the agent is an agent capable of eliciting a taste response.

11. An in vitro method of identifying a modulator of taste signalling, comprising the steps of:
    (i) determining the signalling response elicited in the human taste cells of claim 1 or claim 2 by a known taste molecule in the presence of a test compound; and
    (ii) comparing the signalling response elicited in the cells in the presence of the test compound as determined in step (i) with the signalling response elicited in the cells in the absence of the test compound,
    wherein an alteration in the signalling response determined in (i) as compared to the signalling response in the absence of the test compound indicates that the test compound is a modulator of taste signalling.

12. The method of claim 9, wherein the signalling response is selected from the group consisting of an alteration in
    (i) intracellular calcium signalling, and
    (ii) cellular membrane potential.

13. A kit comprising the cells of claim 1 or claim 2.

14. The method of claim 10, wherein the signaling response is selected from the group consisting of an alteration in
    (i) intracellular calcium signalling, and
    (ii) cellular membrane potential.

15. The method of claim 11, wherein the signaling response is selected from the group consisting of an alteration in
    (i) intracellular calcium signalling, and
    (ii) cellular membrane potential.

* * * * *